(12) United States Patent
Nakagawa et al.

(10) Patent No.: US 6,812,231 B2
(45) Date of Patent: Nov. 2, 2004

(54) BENZAMIDINE DERIVATIVE

(75) Inventors: Tadakiyo Nakagawa, Kanagawa (JP);
Kazuyuki Sagi, Kanagawa (JP); Kaoru Yoshida, Kanagawa (JP); Yumiko Fukuda, Kanagawa (JP); Masataka Shoji, Kanagawa (JP); Shunji Takehana, Kanagawa (JP); Takashi Kayahara, Kanagawa (JP); Akira Takahara, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 55 days.

(21) Appl. No.: 10/073,985

(22) Filed: Feb. 14, 2002

(65) Prior Publication Data

US 2002/0107290 A1 Aug. 8, 2002

Related U.S. Application Data

(63) Continuation of application No. 09/731,729, filed on Dec. 8, 2000, which is a continuation of application No. PCT/JP99/03055, filed on Jun. 8, 1999.

(30) Foreign Application Priority Data

Jun. 8, 1998 (JP) ........................................... 10-159627
Jun. 8, 1998 (JP) ........................................... 10-159628

(51) Int. Cl.$^7$ ..................... A61K 31/501; C07F 9/02; C07D 42/00; C07C 257/00; C01B 25/16
(52) U.S. Cl. .................. 514/256; 514/252.01; 514/148; 514/317; 514/619; 514/639; 544/232; 544/238; 544/243; 546/192; 564/245; 564/244; 564/163; 423/316
(58) Field of Search ................................. 514/148, 256, 514/317, 252.01, 619, 639; 544/232, 238, 243; 546/192; 564/163, 244, 245; 423/316

(56) References Cited

U.S. PATENT DOCUMENTS 6,037,365 A * 3/2000 Bovy et al. ................. 514/471
2002/0055522 A1 * 5/2002 Liebeschuetz et al. ...... 514/330

FOREIGN PATENT DOCUMENTS

| JP | 7-330695 | | 12/1995 |
|---|---|---|---|
| WO | 93/07867 | * | 4/1993 |
| WO | WO 95/23609 | | 9/1995 |
| WO | 97/24118 | | 7/1997 |
| WO | WO 98 06740 A | | 2/1998 |
| WO | WO 98/31661 | | 7/1998 |
| WO | 99/64392 | | 12/1999 |

OTHER PUBLICATIONS

XP002214471, Database WPI, Section Ch, Week 199608, Derwent Publications Ltd., London, GB, Class B05, AN 1996–074829, Dec. 19, 1995 (Abstract), Green Cross Corp.
XP002214472, Database WPI, Section Ch, Week 199811, Derwent Publications Ltd., London, GB, Class B02, An 1998–114794, Jan. 6, 1998 (Abstract), Banyu Pharm Co. Ltd.
David J. Robison et al, "Active site of bovine factor Xa", Journal of Biological Chemistry, vol. 255, No. 5, 1980, pp. 2014–2021, XP002214470.
Joerg Stuerzebecher et al, "Structure–activity relationships of inhibitors derived from 3–amidinophenylalanine", Journal of Enzyme Inhibition, New York, NY, vol., 9, No. 9, 1995, pp. 87–99.

* cited by examiner

*Primary Examiner*—Richard L. Raymond
*Assistant Examiner*—Tamthom N. Troung
(74) *Attorney, Agent, or Firm*—Oblon, Spivak, McClelland, Maier & Neustadt, P.C.

(57) ABSTRACT

Benzamidine derivatives of the following formula, analogs thereof and pharmaceutically acceptable salts thereof are provided. These compounds have an effect of inhibiting activated blood-coagulation factor X, and they are useful as agents for preventing or treating various diseases caused by thrombi or emboli.

2 CF$_3$CO$_2$H

17 Claims, No Drawings

BENZAMIDINE DERIVATIVE

The present application is a Continuation Application of U.S. Ser. No. 09/731,729, filed Dec. 8, 2000, allowed, which in turn is a Continuation Application of PCT/JP99/03055, filed Jun. 8, 1999.

BACKGROUND OF THE INVENTION

The present invention relates to new benzamidine derivatives which can be orally administered to exhibit a strong anticoagulant effect by reversibly inhibiting activated blood-coagulation factor X; anticoagulants containing them as active ingredients; and agents for preventing or treating diseases caused by thrombi or emboli. These diseases include, for example, cerebrovascular disorders such as cerebral infarction, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral obliteration; deep vein thrombosis; disseminated intravascular coagulation syndrome; thrombus formation after an artificial blood vessel-forming operation or artificial valve substitution; re-occlusion and re-stenosis after a coronary bypass-forming operation; re-occlusion and re-stenosis after reconstructive operation for the blood circulation such as percutaneous transluminal coronary angioplasty (PTCA) or percutaneous transluminal coronary recanalization (PTCR); and thrombus formation in the course of the extracorporeal circulation.

As the habit of life is being westernized and people of advanced ages are increasing in Japan, thrombotic and embolismic patients such as those suffering from myocardial infarction, cerebral thrombosis and peripheral thrombosis are increasing in number year by year, and the treatment of patients with these diseases is becoming more and more important in the society. Anticoagulation treatment is included in the internal treatments for the remedy and prevention of thrombosis, like radiotherapy and antithrombocytic therapy.

Antithrombins were developed as thrombus-formation inhibitors in the prior art. However, it has been known that since thrombin not only controls the activation of fibrinogen to form fibrin, which is the last step of the coagulation reaction, but also deeply relates to the activation and coagulation of blood platelets, the inhibition of the action of thrombin causes a danger of causing hemorrhage. In addition, when antithrombins are orally administered, the bioavailability thereof is low. At present, no antithrombin which can be orally administered is available on the market.

Since the activated blood coagulation factor X is positioned at the juncture of an exogenous coagulation cascade reaction and an endogenous coagulation cascade reaction and in the upstream of thrombin, it is possible to inhibit the coagulation system more efficiently and specifically, than the thrombin inhibition, by inhibiting the factor X (THROMBOSIS RESEARCH, Vol. 19, pages 339 to 349; 1980).

DISCLOSURE OF THE INVENTION

The object of the present invention is to provide compounds having an excellent effect of inhibiting the effect of activated blood coagulation factor X.

Another object of the present invention is to provide compounds having an effect of specifically inhibiting the effect of activated blood coagulation factor X, which can be orally administered.

Still another object of the present invention is to provide a blood-coagulation inhibitor or an agent for preventing or treating thrombosis of embolism, which contains one of the above-described compounds.

After intensive investigations made under these circumstances, the inventors have found that specified new benzamidine derivatives have an excellent effect of inhibiting activated blood coagulation factor X and are usable for preventing and treating various diseases caused by thrombi and emboli. The present invention has been completed on the basis of this finding.

Namely, the present invention provides benzamidine derivatives of following general formula (1-1), (1-2), (1-3) or (1-4) or pharmaceutically acceptable salts thereof, and blood coagulation inhibitors containing them as the active ingredients:

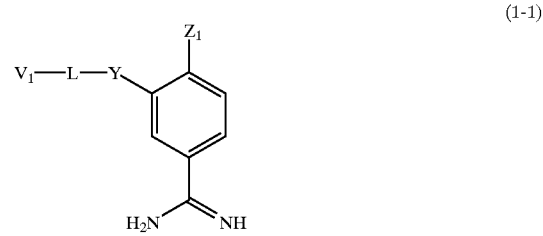

(1-1)

In general formula (1-1), L represents an organic group of following formulae (2) to (5):

(2)

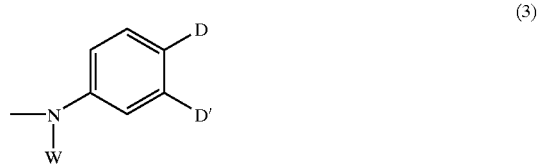

(3)

(4)

(5)

In formulae (2), (3) and (5), W represents hydrogen atom, an alkyl group having 1 to 6 carbon atoms, an aryl group having 4 to 10 carbon atoms or an aralkyl group having 5 to 12 carbon atoms, one of D and D' in formula (3) represents a bond to Y in general formula (1-1) and the other represents hydrogen atom.

In formula (2), X represents hydrogen atom, carboxyl group, an alkoxycarbonyl group having 1 to 3 carbon atoms, an alkyl group having 1 to 3 carbon atoms which may have a substituent(s) or benzimidoyl group which may have a substituent(s). The substituent(s) is (are) selected from among carboxyl group, alkoxycarbonyl groups having 2 to 8 carbon atoms, alkylsulfonyloxy groups having 1 to 6 carbon atoms, piperidyloxy group, iminoalkylpiperidyloxy groups having 6 to 10 carbon atoms, alkoxycarbonylpiperidyloxy groups having 7 to 14 carbon atoms, piperidylalkyl groups having 6 to 8 carbon atoms, iminoalkylpiperidylalkyl groups having 7 to 11 carbon atoms, alkoxycarbonylpiperidylalkyl groups having 8 to 15 carbon atoms, pyrrolidinyloxy group, iminoallcylpyrrolidinyloxy groups having 5 to 9 carbon atoms, alkoxycarbonylpyrrolidinyloxy groups having 7 to 13 carbon atoms, amidino group, mono- or dialkylamidino groups having 2 to 7 carbon atoms, hydroxyl group, halogeno groups, indolyl group and alkyl groups having 1 to 3 carbon atoms. In formula (2), X and W may be bonded together to form a ring and, in this case, —W—X— represents ethylene group, trimethylene group or tetramethylene group.

When L is an organic group of any of formulae (2) to (4), $V_1$ represents hydrogen atom, benzoyl, benzenesulfonyl, 2-naphthalenesulfonyl, piperazinecarbonyl, cinnamoyl, piperidinecarbonyl, 4-methylthiazole-5-carbonyl, phenylacetyl, phenylthiocarbonyl or benzimidoyl group which may have a substituent(s) or an alkanesulfonyl group having 1 to 6 carbon atoms, which may have a substituent(s). When L is an organic group of formula (5), $V_1$ represents an aryl group having 4 to 10 carbon atoms, which may have a substituent(s).

When L is an organic group of any of formulae (2) to (5) and $V_1$ has a substituent, the substituent is selected from among carboxyl group, alkoxycarbonyl groups having 2 to 7 carbon atoms, carbamoyl group, mono- or dialkylcarbamoyl groups having 2 to 7 carbon atoms, amidino group, mono- or dialkylamidino groups having 2 to 7 carbon atoms, acyl groups having 1 to 8 carbon atoms, halogeno groups, amino group, mono- or dialkylamino groups having 1 to 6 carbon atoms, arylamino groups having 4 to 6 carbon atoms, alkoxycarbonylamino groups having 2 to 7 carbon atoms, aminoalkyl groups having 1 to 3 carbon atoms, mono- or dialkylaminoalkyl groups having 2 to 7 carbon atoms, N-alkyl-N-alkoxycarbonylaminoalkyl groups having 4 to 10 carbon atoms, piperidyloxy group, iminoalkylpiperidyloxy groups having 6 to 10 carbon atoms, alkoxycarbonylpiperidyloxy groups having 8 to 14 carbon atoms, pyrrolidinyloxy group, iminoalkylpyrrolidinyloxy groups having 5 to 9 carbon atoms, alkoxycarbonylpyrrolidinyloxy groups having 7 to 13 carbon atoms, hydroxycarbonylalkyl groups having 2 to 7 carbon atoms, alkoxycarbonylalkyl groups having 3 to 8 carbon atoms, hydroxycarbonylalkenyl groups having 3 to 7 carbon atoms, alkoxycarbonylalkenyl groups having 4 to 8 carbon atoms, aryl groups having 4 to 10 carbon atoms, arylalkenyl groups having 6 to 12 carbon atoms, alkoxyl groups having 1 to 10 carbon atoms, nitro group, trifluoromethyl group, alkyl groups having 3 to 8 carbon atoms, arylsulfonyl groups having 4 to 10 carbon atoms, arylalkyl groups having 5 to 12 carbon atoms, piperazinecarbonyl group, iminoalkylpiperazinecarbonyl groups having 7 to 10 carbon atoms, piperazinesulfonyl group, iminoalkylpiperazinesulfonyl groups having 6 to 9 carbon atoms, piperidylalkyl groups having 6 to 9 carbon atoms, iminoalkylpiperidylalkyl groups having 8 to 12 carbon atoms, piperidylidenealkyl groups having 6 to 9 carbon atoms, iminoalkylpiperidylinealkyl groups having 8 to 12 carbon atoms, guanidino group, dialkylguanidino groups having 3 to 5 carbon atoms, phosphono group, dialkoxyphosphoryl groups having 2 to 9 carbon atoms, monoalkoxyhydroxyphosphoryl groups having 1 to 4 carbon atoms, trialkylamidino groups having 4 to 7 carbon atoms, dialkoxybenzoyl groups having 9 to 13 carbon atoms, 1-alkylpyridinio groups having 6 to 9 carbon atoms and groups of the following formulae:

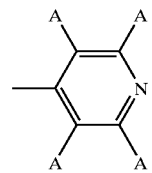
(6)

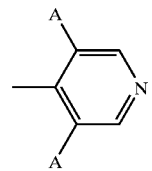
(7)

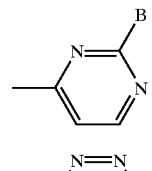
(8)

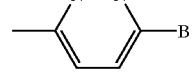
(9)

In formulae (6) and (7), A represents a halogeno group, and in formulae (8) and (9), B represents hydrogen atom, an alkyl group having 1 to 6 carbon atoms, a halogeno group or amino group.

Y represents any of following formulae (10) to (16):

(10)

(11)

(12)

(13)

(14)

(15)

(16)

In formulae (10) and (11), n represents an integer of 0 to 2. In formula (16), $R^1$ represents a hydrogen atom, a hydroxycarbonylalkyl group having 2 to 7 carbon atoms, an alkoxycarbonylalkyl group having 3 to 8 carbon atoms or a hydroxycarbonylalkenyl group having 3 to 7 carbon atoms.

$Z_1$ represents a group of any of following formulae (17) to (24):

(17)

(18)

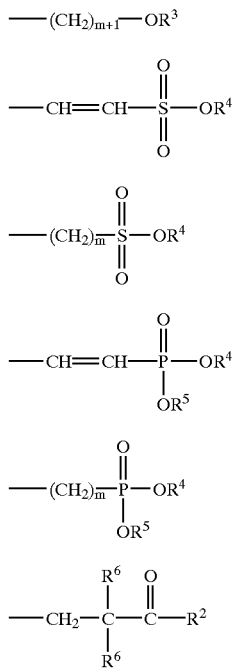

(19) —(CH₂)ₘ₊₁—OR³

(20) —CH=CH—S(=O)(=O)—OR⁴

(21) —(CH₂)ₘ—S(=O)(=O)—OR⁴

(22) —CH=CH—P(=O)(OR⁴)—OR⁵

(23) —(CH₂)ₘ—P(=O)(OR⁴)—OR⁵

(24) —CH₂—C(R⁶)(R⁶)—C(=O)—R²

In formulae (17), (19), (21) and (23), m represents an integer of 0 to 3. In formulae (17), (18) and (24), R² represents hydroxyl group, an alkoxyl group having 1 to 5 carbon atoms, trifluoromethyl group, amino group or a mono- or dialkylamino group having 1 to 6 carbon atoms. In formula (19), R³ represents hydrogen atom, an alkyl group having 1 to 6 carbon atoms or acetyl group. In formulae (20) to (230), R⁴ represents hydrogen atom or an alkyl group having 1 to 6 carbon atoms. In formulae (22) and (23), R⁵ represents hydrogen atom or an alkyl group having 1 to 6 carbon atoms. In formula (24), R⁶ represents a halogeno group:

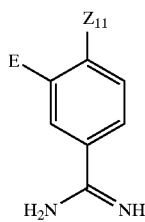

(1-2)

wherein $Z_{11}$ represents carboxyethyl group, ethoxycarbonylethyl group, hydroxymethyl group or hydroxypropyl group, and E represents an oil-soluble organic group

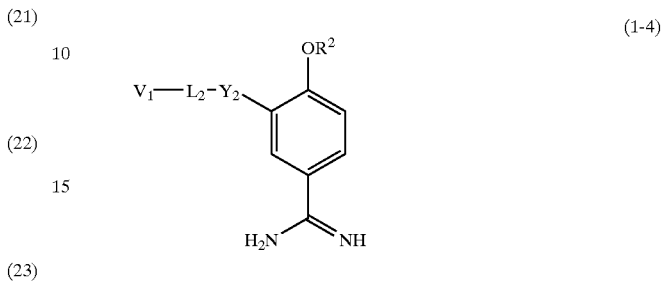

(1-3)

In general formula (1-3), L represents an organic group of any of formulae (2) to (5) in above general formula (1-1). In formulae (2), (3) and (5), W is as defined in above general formula (1-1). In general formula (2), X is as defined in above general formula (1-1), When L represents an organic group of formulae (2) to (4), $V_2$ represents benzoyl, benzenesulfonyl, 2-naphthalenesulfonyl, cinnamoyl, piperidinecarbonyl, phenylacetyl, phenylthiocarbonyl or benzimidoyl

(1-4)

In general formula (1-4), $L_2$ represents an organic group represented by formulae (2) to (4) in general formula (1-1), and W in formulae (2) and (3) and X in formula (2) are each as defined in above general formula (1-1), when $L_2$ represents an organic group of formulae (2) to (4), $V_1$ is as defined in above general formula (1-1), and when $V_1$ has a substituent(s), the substituent is as defined in above general formula (1-1), and $Y_2$ is any of formulae (10) and (11) in above general formula (1-1), and $R^8$ represents hydrogen atom, an alkyl group having 1 to 6 carbon atoms or acetyl group.

BEST MODE FOR CARRYING OUT THE INVENTION

The alkyl groups in the present invention may be branched or have a ring. For example, the alkyl groups include cyclohexylmethyl group or the like. The term "aryl" herein involves not only aromatic cyclic hydrocarbon groups but also aromatic heterocyclic groups having 1 to 3 heteroatoms selected from among O, N and S. Examples of the aryl groups include phenyl, pyridyl, imidazolyl and pyrrolyl groups. An group having a substituent. When L is an organic group of formula (5), $V_2$ represents an aryl group having 4 to 10 carbon atoms, which may have a substituent.

When L represents an organic group of formulae (2) to (5), the substituents of $V_2$ include trialkylamidino groups having 4 to 7 carbon atoms, dialkoxybenzoyl groups having 9 to 13 carbon atoms and 1-alkylpyridinio groups having 6 to 9 carbon atoms.

Y is represented by any of formulae (10) to (16) in above general formula (1-1), wherein n represents an integer of 1 or 2, and $R^1$ is as defined above.

$Z_2$ represents hydrogen atom, an alkyl group having 1 to 6 carbon atoms, a halogeno group or a group of following formula (13-2):

(13-2) —CH₂—C(=O)—R²²

In formula (13-2), $R_{22}$ represents carboxyl group or an alkoxycarbonyl group having 2 to 5 carbon atoms. example of the arylalkenyl groups is 2-(4-pyridyl)vinyl group. Dialkylamidino groups include N,N-dialkylamidino groups and N,N'-dialkylamidino groups. The two alkyl groups in the dialkylcarbamoyl groups, dialkylamidino groups, dialkylamino groups, dialkylaminoalkyl groups, dialkylaminosulfonyl groups and dialkylguanidino groups may be bonded together to form a ring. In those groups, one of $CH_2$'s may be replaced with O, NH or S. For example, dialkylcarbamoyl groups include, for example, 1-pyrrolidinecarbonyl group; dialkylamidino groups include, for example, 2-imidazoline-2-yl group and (pyrrolidine-1-yl)(imino)methyl group; and dialkylguanidino groups include, for example, imidazoline-2-amino group. The acyl groups include not only alkylcarbonyl groups but also arylcarbonyl groups. For example, the acyl groups having 1 to 8 carbon atoms include benzoyl group. The alkoxyl groups include, for example, cyclohexyloxy group and phenoxyl group. The alkoxycarbonyl groups include benzyloxycarbonyl group, etc. Preferred 1-alkylpyridinio groups having 6 to 9 carbon atoms are all of those having 6 carbon atoms or 7 to 9 carbon atoms.

The compounds of the present invention may have an asymmetric carbon atom. These compounds include mixtures of various stereoisomers such as geometrical isomers, tautomers and optical isomers, and those isolated therefrom. The amidino group in the compounds of the present invention may be replaced with a suitable substituent which can be changed into the amidino group in vivo. For example, hydrogen atom bonded to nitrogen atom having double bond in amidino group bonded to the benzene ring in general formulae (1-1) to (1-4) is replaced with hydroxyl group, an alkoxyl group such as ethoxyl group, amino group, carboxyl group, an alkoxycarbonyl group such as ethoxycarbonyl group, an alkylsulfonyl group such as ethylsulfonyl group, carbamoyl group, carbamoyl group in which one or two hydrogen atoms are replaced with an alkyl group such as diethoxycarbamoyl group, formyl group, an acyl group such as acetyl group or an alkylcarboxyl group such as acetoxyl group.

L in general formula (1-1) is preferably that represented by formulae (2) to (4), more preferably formulae (2) and (4), and particularly formula (2).

W is preferably hydrogen atom or an alkyl group having 1 to 6 carbon atoms. W is particularly preferably hydrogen atom. X is preferably hydrogen atom, a carboxyalkyl group having 2 or 3 carbon atoms or an alkoxycarbonylalkyl group having 3 to 10 carbon atoms. W is particularly preferably hydrogen atom, carboxymethyl group or ethoxycarbonylmethyl group. X is preferably hydrogen atom, carboxyl group, an alkyl group having 1 to 3 carbon atoms, which may have a substituent(s), or benzyl group which may have a substituent(s). X is particularly preferably hydrogen atom or an alkyl group having one carbon atom and a substituent.

When X has a substituent, the substituent is, for example, benzyloxycarbonyl group, carboxyl group, methoxycarbonyl group, ethoxycarbonyl group, ethanesulfonyloxy group, butanesulfonyloxy group, 4-piperidyloxy group, 1-acetimidoyl-4-piperidyloxy group, (1-acetimidoyl-4-piperidyl)methyl group, 1-acetimidoyl-3-pyrrolidyloxy group, isopropyl group, 3-indolyl group or iodine atom. In these substituents, carboxyl group is particularly preferred.

$V_1$ is preferably benzoyl group which may have a substituent(s), piperidinecarbonyl group which may have a substituent(s) or pyridinecarbonyl group which may have a substituent(s). $V_1$ is more preferably benzoyl group having a substituent(s) or piperidinecarbonyl group having a substituent(s).

When $V_1$ has a substituent, the substituent is preferably 4-piperydyloxy group, 1-acetimidoyl-4-piperidyloxy group, 4-pyridyl group, tetrafluoropyridyl group, 3,5-dichloropyridyl group, 6-chloropyridazyl group, pyridazyl group, 2-chloropyrimidyl group, pyrimidyl group, 4-pyridine-4-ylmethyl group or 4-pyridylcarbonyl group. The substituent is more preferably 1-acetimidoyl-4-piperidyloxy group or 4-pyridyl group. $V_1$ is particularly preferably either 1-acetimidoyl-4-piperidyloxybenzoyl group or 1-(4-pyridyl)-piperizine-4-carbonyl group.

It is more preferred that Y represents an organic group of formula (10) wherein n is an integer of 1.

$Z_1$ is preferably a group represented by formula (17), (19), (21) or (23). $Z_1$ is more preferably carboxyethyl group, ethoxycarbonylethyl group, sulfoethyl group, phosphonoethyl group, diethoxyphosphorylethyl group, monoethoxyhydroxyphosphorylethyl group, hydroxymethyl group or hydroxypropyl group. $Z_1$ is particularly preferably carboxyethyl group, ethoxycarbonylethyl group, hydroxymethyl group or hydroxypropyl group.

In the compounds of general formula (1-1), benzamidine derivatives of general formula (1-1) wherein L represents an organic group of formula (2), W represents hydrogen atom and X represents any of hydrogen atom, carboxymethyl group and ethoxycarbonylmethyl group, or pharmaceutically acceptable salts thereof are preferred.

Benzamidine derivatives of general formula (1-1) wherein Y represents an organic group of formula (10), and n represents an integer of 1 or 2 or pharmaceutically acceptable salts thereof are preferred.

Preferred compounds are benzamidine derivatives of general formula (1-1) wherein $V_1$ represents 1-acetimidoyl-4-piperidyloxybenzoyl group, 1-(4-pyridyl)-piperidine-4-carbonyl group, 1-(2,3,5,6-tetrafluoropyridine-4-yl)-piperidine-4-carbonyl group, 1-(3,5-dichloropyridine-4-yl)-piperidine-4-carbonyl group, 1-(6-chloropyridazine-3-yl)-piperidine-4-carbonyl group, 1-(pyridazine-3-yl)-piperidine-4-carbonyl group, 1-(2-chloropyrimidine-4-yl)-piperidine-4-carbonyl group, 1-(pyrimidine-4-yl)-piperidine-4-carbonyl group, 1-(4-pyridine-4-ylmethyl)-piperidine-4-carbonyl group, 1-(4-pyridine-4-carbonyl)-piperidine-4-carbonyl group or 4-methyl-2-pyridyl-4-ylthiazole-5-carbonyl group, or pharmaceutically acceptable salts thereof.

Preferred compounds are benzamidine derivatives of general formula (1-1) wherein $Z_1$ represents carboxyethyl group, ethoxycarbonylethyl group, carboxyvinyl group, ethoxycarbonylvinyl group, carbamoylethyl group, carbamoylvinyl group, carboxyl group, ethoxycarbonyl group, methoxycarbonyl group, sulfoethyl group, sulfovinyl group, phosphonovinyl group, diethoxyphosphorylvinyl group, monoethoxyhydroxyphosphorylvinyl group, phosphonoethyl group, diethoxyphosphorylethyl group, monoethoxyhydroxyphosphorylethyl group, hydroxymethyl group, hydroxypropyl group or acetoxymethyl group, or pharmaceutically acceptable salts thereof.

Preferred compounds are benzamidine derivatives of general formula (1-1) wherein Y represents an organic group of formula (10), $V_1$ represents 1-acetimidoyl-4-piperidyloxybenzoyl group or 1-(4-pyridyl)piperidine-4-carbonyl group and $Z_1$ represents carboxyethyl group, ethoxycarbonylethyl group, sulfoethyl group, hydroxymethyl group or hydroxypropyl group, or pharmaceutically acceptable salts thereof.

Preferred compounds are benzamidine derivatives of general formula (1-1) wherein L represents an organic group of formulae (2) to (4) and Y represents an organic group of formulae (10) to (13), or pharmaceutically acceptable salts thereof.

Preferred benzamidine derivatives are those of general formula (1-1) wherein, when L represents an organic group of formulae (2) to (4), $V_1$ represents hydrogen atom, benzoyl, benzenesulfonyl, 2-naphthalenesulfonyl, cinnamoyl, piperidinecarbonyl, phenylacetyl, phenylthiocarbonyl or benzimidoyl group which may have a substituent(s) or an alkanesulfonyl group having 1 to 6 carbon group, which may have a substituent(s); when L represents an organic group of formula (5), $V_1$ represents an aryl group having 4 to 10 carbon atoms, which may have a substituent(s);

when L represents an organic group of formulae (2) to (5), the substituents of $V_1$ are carboxyl group, alkoxycarbonyl groups having 2 to 7 carbon atoms, carbamoyl group, mono- or dialkylcarbamoyl groups having 2 to 7 carbon atoms, trialkylamidino groups having 4 to 7 carbon atoms, amidino group, mono- or dialkylamidino groups having 2 to 7 carbon atoms, acyl groups having 1 to 8 carbon atoms, halogeno groups, amino group, mono- or dialkylamino groups having 1 to 6 carbon atoms, arylamino groups having 4 to 6 carbon atoms, alkoxycarbonylamino groups having 2 to 7 carbon atoms, aminoalkyl groups having 1 to 3 carbon atoms, mono- or dialkylaminoalkyl groups having 2 to 7 carbon atoms, N-alkyl-N-alkoxycarbonylaminoalkyl groups having 4 to 10 carbon atoms, piperidyloxy group, iminoalkylpiperidyloxy groups having 6 to 10 carbon atoms, alkoxycarbonylpiperidyloxy groups having 8 to 14 carbon atoms, pyrrolidinyloxy group, iminoalkylpyrrolidinyloxy groups having 5 to 9 carbon atoms, alkoxycarbonylpyrrolidinyloxy groups having 7 to 13 carbon atoms, hydroxycarbonylalkyl groups having 2 to 7 carbon atoms, alkoxycarbonylalkyl groups having 3 to 8 carbon atoms, hydroxycarbonylalkenyl groups having 3 to 7 carbon atoms, alkoxycarbonylalkenyl groups having 4 to 8 carbon atoms, aryl groups having 4 to 10 carbon atoms, arylalkenyl groups having 6 to 12 carbon atoms, alkoxyl groups having 1 to 10 carbon atoms, nitro group, trifluoromethyl group, alkyl groups having 3 to 8 carbon atoms, arylsulfonyl groups having 4 to 10 carbon atoms, arylalkyl groups having 5 to 12 carbon atoms, piperazinecarbonyl group, iminoalkylpiperazinecarbonyl groups having 7 to 10 carbon atoms, piperazinesulfonyl group, iminoalkylpiperazinesulfonyl groups having 6 to 9 carbon atoms, piperidylalkyl groups having 6 to 9 carbon atoms, iminoalkylpiperidylalkyl groups having 8 to 12 carbon atoms, piperidylidenealkyl groups having 6 to 9 carbon atoms, iminoalkylpiperidylidenealkyl groups having 8 to 12 carbon atoms, guanidino groups, dialkylguanidino groups having 3 to 5 carbon atoms, phosphono group, dialkoxyphosphoryl groups having 2 to 9 carbon atoms and monoalkoxyhydroxyphosphoryl groups having 1 to 4 carbon atoms, Y represents a group of formulae (10) to (16), and n in formulae (10) and (11) represents an integer of 1 or 2, $Z_1$ represents a group of formulae (17) and (18) wherein m represents an integer of 1 to 3, and $R^2$ represents hydroxyl group, an alkoxyl group having 1 to 5 carbon atoms, amino group or a mono- or dialkylamino group having 1 to 6 carbon atoms, and pharmaceutically acceptable salts thereof.

Preferably, L represents an organic group of formula (2), W represents hydrogen atom and X represents hydrogen atom, carboxymethyl group or ethoxycarbonylmethyl group.

Preferably, Y represents an organic group of formula (10) and n represents an integer of 1.

Preferably, $V_1$ represents 1-acetimidoyl-4-piperidyloxybenzoyl group or 1-(4-pyridyl)-piperizine-4-carbonyl group.

Preferably, $Z_1$ represents carboxyethyl group, ethoxycarbonylethyl group, carboxyvinyl group, ethoxycarbonylvinyl group, carbamoylethyl group or carbamoylvinyl group.

Preferably, L represents an organic group of formula (2), Y represents an organic group of formula (10), $V_1$ represents 1-acetimidoyl-4-piperidyloxybenzoyl group or 1-(4-pyridyl)-piperizine-4-carbonyl group, and $Z_1$ represents carboxyethyl group, ethoxycarbonylethyl group or carbamoylethyl group.

Benzamidine derivatives of general formula (1-2) and pharmaceutically acceptable salts thereof have an effect of inhibiting the activated blood coagulation factor X. In general formula (1-2), $Z_{11}$ is as defined above, and E represents an oil-soluble organic group which, together with other groups in general formula (1-2), imparts an effect of inhibiting the activated blood coagulation factor X to the compounds of general formula (1-2). The effect on the activated blood coagulation factor X can be determined by a method described in Examples in this specification. Groups E are those having a bonding group capable of bonding to the benzene ring, a terminal aromatic group and/or a heterocyclic group. They are organic groups which are, as a whole, soluble in an oil. The bonding groups herein include aliphatic organic groups, which may contain an oxygen atom or nitrogen atom, such as alkylene groups and hydroxyalkylene groups. The terminal aromatic groups and/or heterocyclic groups include phenyl group, naphthyl group, piperidine group, pyridine group, etc. The oil-soluble organic groups are preferably the same as —Y—L—$V_1$ in above formula (1-1) wherein L represents an organic group of formula (2), Y represents an organic group of formula (10) and $V_1$ represents 1-acetimidoyl-4-piperidyloxybenzoyl group or 1-(4-pyridyl)-piperidine-4-carbonyl group.

Preferred groups L and more preferred groups L in general formula (1-3) are the same as those described above with reference to general formula (1-1). When L is an organic group of above formulae (2) to (5), $V_2$ and substituents thereof are as described above. Particularly preferred $V_2$ is benzoyl group having a substituent which is selected from among trialkylamidino groups having 4 to 7 carbon atoms, dialkoxybenzoyl groups having 9 to 13 carbon atoms and 1-alkylpyridinio groups having 6 to 9 carbon atoms.

$V_2$ is preferably 4-(3,4-dimethoxybenzoyl)benzoyl group, 1-(1-methylpyridinium-4-yl)piperizine-4-carbonyl group or 4-(1-methyl-2-imidazoline-2-yl)benzoyl group.

Y is any of above formulae (10) to (16) in general formula (1-1), and $Z_2$ is hydrogen atom, an alkyl group having 1 to 6 carbon atoms, a halogeno group or a group of formula (13-2). Preferred groups Y are the same as those in general formula (1-1). A preferred group $Z_2$ is that of formula (13-2) wherein $R_{22}$ is carboxyl group.

Preferably L in general formula (1-3) represents an organic group of formula (2), W represents hydrogen atom, X represents hydrogen atom, $V_2$ represents 4-(3,4-dimethoxybenzoyl)benzoyl group, 1-(1-methylpyridinium-4-yl)piperidine-4-carbonyl group or 4-(1-methyl-2-imidazoline-2-yl)benzoyl group and $Z_2$ represents hydrogen atom or 2-carboxy-2-oxoethyl group.

Preferably L in general formula (1-3) represents an organic group of formula (2), W represents hydrogen atom, X represents hydrogen atom, $V_2$ represents. 4-(1-methyl-2-imidazoline-2-yl)benzoyl group and $Z_2$ represents 2-carboxy-2-oxoethyl group.

Preferred groups W, X and $V_1$ and more preferred groups W, X and $V_1$ in general formula (1-4) are the same as those described above with reference to general formula (1-1). $L_2$ is preferably that represented by formula (2) or (4). More preferably, $L_2$ is that represented by formula (2).

$Y_2$ is preferably that represented by formula (10), and $R^3$ is preferably hydrogen atom, an alkyl group having 1 to 3 carbon atoms or acetyl group. $R^3$ is more preferably hydrogen atom.

In general formula (1-4), preferably, $L_2$ represents an organic group of formula (2), W represents hydrogen atom and X represents any of hydrogen atom, carboxymethyl group and ethoxycarbonylmethyl group.

In general formula (1-4), preferably $Y_2$ represents an organic group of formula (10), and n represents an integer of 1 or 2. Particularly preferably, n represents an integer of 1.

In general formula (1-4), $V_1$ is preferably 1-acetimidoyl-4-piperidyloxybenzoyl group, 1-(4-pyridyl)-piperidine-4-carbonyl group, 1-(2,3,5,6-tetrafluoropyridine-4-yl)-piperidine-4-carbonyl group, 1-(3,5-dichloropyridine-4-yl)-piperidine-4-carbonyl group, 1-(6-chloropyridazine-3-yl)-piperidine-4-carbonyl group, 1-(pyridazine-3-yl)-piperidine-4-carbonyl group, 1-(2-chloropyrimidine-4-yl)-piperidine-4-carbonyl group, 1-(pyrimidine-4-yl)-piperizine-4-carbonyl group, 1-(4-pyridine-4-ylmethyl)-piperidine-4-carbonyl group, 1-(4-pyridine-4-carbonyl)-piperidine-4-carbonyl group or 4-methyl-2-pyridyl-4-ylthiazole-5-carbonyl group.

In general formula (1-4), preferably $L_2$ represents an organic group, Y represents an organic group of formula (10), $V_1$ represents 1-acetimidoyl-4-piperidyloxybenzoyl group or 1-(4-pyridyl)piperizine-4-carbonyl group and $R^3$ represents hydrogen atom.

Typical processes for producing compounds of the present invention are as follows:

A compound (27) can be obtained by reacting an aminoalkyl halide (25), in which nitrogen is protected with benzyloxycarbonyl group, t-butoxycarbonyl group base, with 3-hydroxy-4-iodobenzonitrile (26) in the presence of a base such as potassium carbonate in a solvent such as dimethylformamide. An acrylic acid derivative (28) can be derived from the obtained compound (27) by, for example, condensing it with ethyl acrylate or the like by, for example, Heck reaction in dimethylformamide or the like as the solvent. The protecting group on the nitrogen of the obtained compound (28) can be removed in, for example, an acidic solution such as 4 N solution of hydrogen chloride in dioxane to obtain a corresponding amine (29).

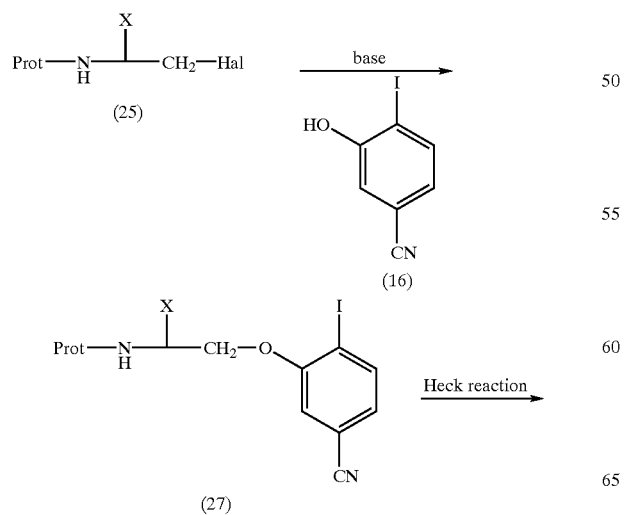

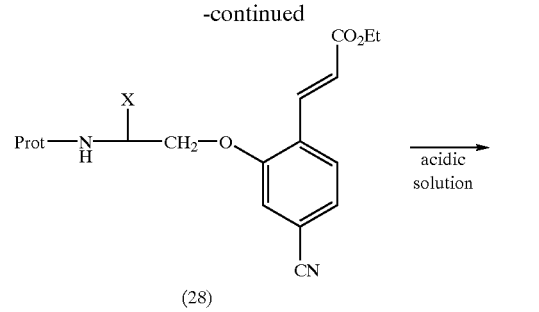

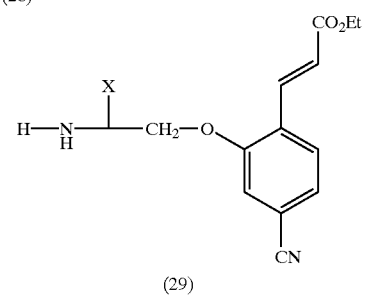

Prot in the above formulae represents a protecting group such as Boc group or Z group, and Hal represents a halogen atom.

Then, the amine (29) is reacted with a condensing agent in the presence of a base such as triethylamine in a solvent such as dimethylformamide. The amine is thus condensed with a carboxylic acid to obtain an amide (30).

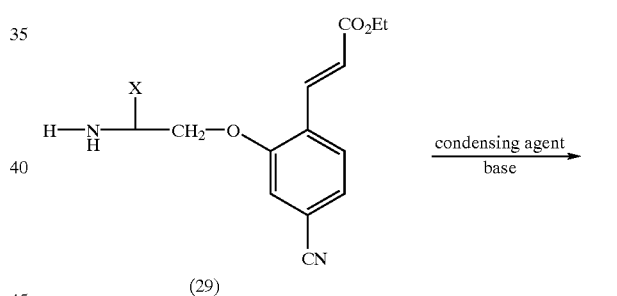

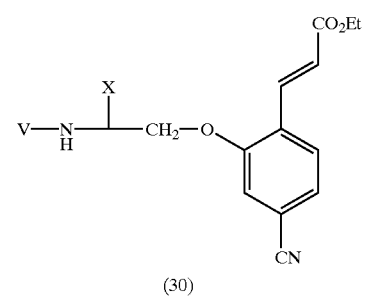

Cyano group in the amide (30) obtained as described above can be converted into amidino group by reacting amide (30) with an alcohol such as ethanol containing a hydrogen halide such as hydrogen chloride and then reacting the reaction product with an ammonium salt such as ammonium carbonate. By these reaction steps, benzamidine derivative (31) of general formula (1-1) wherein L is represented by formula (2), Y is represented by formula (10) and Z is represented by formula (18) can be produced.

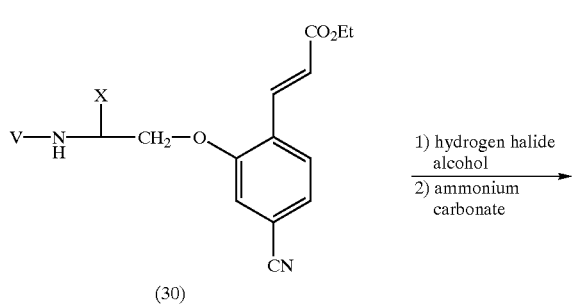

(30)

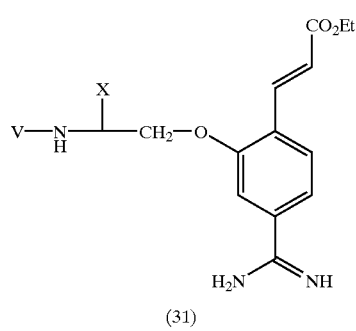

(31)

Benzamidine derivative (32) of general formula (1-1) wherein L is represented by formula (2), Y is represented by formula (10) and Z is represented by formula (17) can be produced by reacting benzamidine derivative (31) in the presence of a catalyst such as palladium/carbon in an alcohol such as methanol as the solvent in hydrogen atmosphere and then hydrolyzing the reaction product in an acidic aqueous solution such as concentrated hydrochloric acid.

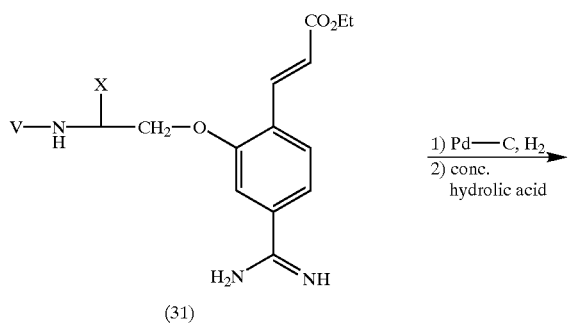

(31)

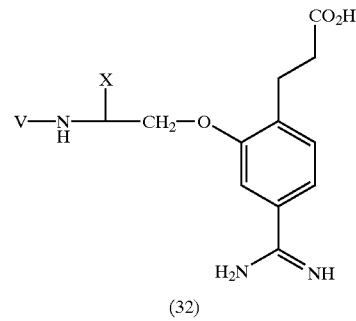

(32)

The compounds produced as described above and salts thereof can be isolated by the purification by a well-known method such as extraction, concentration, concentration under reduced pressure, extraction with a solvent, crystallization, recrystallization, redissolution or various chromatographic techniques.

The salts of the benzamidine derivatives of the present invention are pharmaceutically acceptable ones such as salts of them with mineral acids, e. g. hydrochloric acid, hydrobromic acid, sulfuric acid, nitric acid and phosphoric acid; and organic acids, e. g. formic acid, acetic acid, trifluoroacetic aid, lactic acid, salicylic acid, mandelic acid, citric acid, oxalic acid, maleic acid, fumaric acid, tartaric acid, tannic acid, malic acid, toluenesulfonic acid, methanesulfonic acid and benzenesulfonic acid.

The compounds and salts thereof of the present invention are administered as they are or in the form of various medicinal compositions to patients. The dosage forms of the medicinal compositions are, for example, tablets, powders, pills, granules, capsules, suppositories, solutions, sugar-coated tablets and depots. They can be prepared with ordinary preparation assistants by an ordinary method. For example, the tablets are prepared by mixing the benzamidine derivative, the active ingredient of the present invention, with any of known adjuvants such as inert diluents, e. g. lactose, calcium carbonate and calcium phosphate, binders, e. g. acacia, corn starch and gelatin, extending agents, e. g. alginic acid, corn starch and pre-gelatinized starch, sweetening agents, e. g. sucrose, lactose and saccharin, corrigents, e. g. peppermint and cherry, and lubricants, e. g. magnesium stearate, talc and carboxymethyl cellulose.

When the benzamidine derivatives and salts thereof of the present invention are used as the anticoagulants, they can be administered either orally or parenterally. The dose which varies depending on the age, body weight and conditions of the patient and the administration method is usually 0.01 to 1,000 mg, preferably 0.1 to 50 mg, a day for adults in the oral administration, and 1 $\mu$g to 100 mg, preferably 0.01 to 10 mg, in the parenteral administration.

The following Examples will further illustrate the present invention, which are only preferred embodiments of the invention and which by no means limit the invention.

EXAMPLE 1

Synthesis of ethyl 3-[4-amidino-2-(2-(4-(1-(1-acetimidoyl)-4-piperidyloxy)benzoylamino)ethoxy)phenyl]acrylate bistrifluoroacetate Step 1: Synthesis of ethyl 4-(1-t-butoxycarbonyl-4-piperidyloxy)benzoate 1.7 g (10.2 mmol) of ethyl 4-hydroxybenzoate, 1.76 g (9.3 mmol) of 1-t-butoxycarbonyl-4-hydroxypiperidine, obtained by t-butoxycarbonylating 4-hydroxypiperidine with di-t-butyl dicarbonate in an ordinary manner, and 2.44 g (9.3 mmol) of triphenylphosphine were dissolved in 40 ml of tetrahydrofuran. 1.62 g (9.3 mmol) of diethyl azodicarboxylate was added to the obtained solution at room temperature, and they were stirred overnight. After the treatment with ethyl acetate as the extraction solvent in an ordinary manner, the crude product was obtained. It was purified by the silica gel column chromatography to obtain the title compound.

Yield: 1.57 g (4.5 mmol) (44%)

H-NMR (CDCl3) d δ 1.38 (3H, t), 1.50 (9H, s) 1.70–1.80 (2H, m), 1.90–2.00 (2H, m), 3.30–3.41 (2H, m), 3.63–3.75 (2H, m), 4.35 (2H, q), 4.55 (1H, m), 6.90 (2H, d), 8.00 (2H, d)

Step 2: Synthesis of 4-(1-t-butoxycarbonyl-4-piperidyloxy)benzoic acid 847 mg (2.43 mmol) of ethyl 4-(1-t-butoxycarbonyl-4-piperidyloxy)benzoate was dissolved in 50 ml of ethanol. 5 ml of 1 N sodium hydroxide solution was added to the obtained solution, and they were stirred at room temperature for 3 days. The reaction solution was concentrated and then treated with ethyl acetate as the extraction solvent in an ordinary manner to obtain the title compound.

Yield: 697 mg (2.2 mmol) (92%)

H-NMR (CDCl3) d δ 1.50 (9H, s), 1.70–2.00 (4H, m), 3.30–3.40 (2H, m), 3.65–3.75 (2H, m), 4.60 (1H, s), 6.95 (2H, d), 8.05 (2H, d)

Step 3: Synthesis of 3-hydroxy-4-iodobenzoic acid 30.0 g (217 mmol) of 3-hydroxybenzoic acid was dissolved in 200 ml of acetic acid. 53.0 g (326 mmol) of iodine monochloride was added to the obtained solution at room temperature. After stirring at 45° C. for 15 hours, the solvent was evaporated under reduced pressure. The residue thus obtained was washed with 500 ml of 1% aqueous sodium thiosulfate solution twice and with 500 ml of water twice and then dried to solid at 80° C. under reduced pressure to obtain the title compound.

Yield: 17.2 g (65.2 mmol) (30%)

MS (FAB, m/z) 265 (MH+)

H-NMR (DMSO-d6) δ 7.13 (1H, dd), 7.43 (1H, d), 7.80 (1H, d)

Step 4: Synthesis of 3-hydroxy-4-iodobenzonitrile 22.3 g (89.7 mmol) of 3-hydroxy-4-iodobenzoic acid was dissolved in 300 ml of tetrahydrofuran. 19.7 ml (206 mmol) of ethyl chloroformate and 28.7 ml (206 mmol) of triethylamine were added to the obtained solution at 0° C. After stirring for 15 minutes, triethylamine hydrochloride thus formed was separated by the filtration. The filtrate was added to 300 ml of tetrahydrofuran solution, obtained by bubbling ammonia, at 0° C. After stirring at room temperature for 10 hours, the solvent was evaporated under reduced pressure. The obtained residue was dissolved in 450 ml of dioxane. 17.4 ml (117 mmol) of anhydrous trifluoroacetic anhydride and 21.8 ml (269 mmol) of pyridine were added to the obtained solution at 0° C. After stirring at room temperature for 18 hours, the solvent was evaporated under reduced pressure, and the residue was treated with chloroform as the extraction solvent in an ordinary manner to obtain an oily residue. The residue was dissolved in 180 ml of tetrahydrofuran/methanol (1:1). 90 ml (90.0 mmol) of 1 N aqueous sodium hydroxide solution was added to the obtained solution at room temperature. After stirring them for 4 hours, the solvent was evaporated under reduced pressure. The obtained residue was washed with dichloromethane. After acidifying with 1 N hydrogen chloride, the product was treated with ethyl acetate as the extraction solvent in an ordinary manner to obtain the crude product, which was then purified by the silica gel column chromatography to obtain the title compound.

Yield: 9.29 g (37.9 mmol) (42%)

MS (FAB, m/z) 246 (MH+)

H-NMR (CDCl3) δ 5.63 (1H, br), 6.96 (1H, dd), 7.23 (1H, d), 7.79 (1H, d)

Step 5 Synthesis of t-butyl (2-bromoethyl)carbamate 9.22 g (45 mmol) of 2-bromoethylamine hydrobromide was dissolved in 100 ml of dichloromethane. 7.64 ml (35 mmol) of di-t-butyl dicarbonate, 10.0 g (99 mmol) of triethylamine and 100 mg (0.82 mmol) of 4-(dimethylamino)pyridine were added to the obtained solution, and they were stirred overnight. The obtained mixture was treated with dichloromethane as the extraction solvent in an ordinary manner to obtain the title compound.

Yield: 5.99 g (26.7 mmol) (76%)

H-NMR (CDCl3) δ 1.45 (9H, s), 3.46 (2H, dt), 3.51 (2H, t), 4.95 (1H, br)

Step 6: Synthesis of 3-[2-(t-butoxycarbonylamino)ethoxy]-4-iodobenzonitrile 18.5 g (82.6 mmol) of t-butyl (2-bromoethyl)carbamate was dissolved in 200 ml of DMF. 10.1 g (41.3 mmol) of 3-hydroxy-4-iodobenzonitrile and 5.7 g (41.3 mmol) of potassium carbonate were added to the obtained solution, and they were stirred at 75° C. for 3 hours. After the treatment with ethyl acetate as the extraction solvent in an ordinary manner, the title compound was obtained.

Yield: 11.0 g (28.4 mmol) (69%).

H-NMR (CDCl3) δ 1.46 (9H, s), 3.62 (2H, dt), 4.12 (2H, t), 7.02 (2H, d), 7.88 (2H, d).

Step 7: Synthesis of ethyl 3-[2-(2-(t-butoxycarbonylamino)ethoxy)-4-cyanophenyl]acrylate 11.0 g (28.4 mmol) of 3-[2-(t-butoxycarbonylamino)ethoxy]-4-iodobenzonitrile was dissolved in 200 ml of DMF. 15.4 ml (142 mmol) of ethyl acrylate, 20 ml (142 mmol) of triethylamine and 127 mg (0.567 mmol) of palladium acetate were added to the obtained solution. They were stirred at 100° C. overnight and then treated with ethyl acetate as the extraction solvent in an ordinary manner to obtain the crude product. After the purification by the silica gel column chromatography, the title compound was obtained.

Yield: 9.6 g (26.7 mmol) (94%)

H-NMR (CDCl3) δ 1.38 (3H, t), 1.46 (9H, s), 3.62 (2H, dt), 4.16 (2H, t), 4.28 (2H, q), 6.56 (1H, d), 7.16 (1H, d), 7.27 (1H, d), 7.60 (1H, d), 7.96 (1H, d)

Step 8: Synthesis of ethyl 3-[4-cyano-2-(2-(4-(1-t-butoxycarbonyl-4-piperidyloxy)benzoylamino)ethoxy)phenyl]acrylate 2.72 g (7.56 mmol) of ethyl 3-[2-(2-(t-butoxycarbonylamino)ethoxy)-4-cyanophenyl]acrylate was dissolved in a mixture of 10 ml of dioxane and 20 ml of 4 N solution of hydrogen chloride in dioxane, and the obtained solution was stirred at room temperature for 4 hours.

The solvent was evaporated under reduced pressure, and the obtained crude product was dissolved in 50 ml of dichloromethane. 2.67 g (8.32 mmol) of 4-(1-t-butoxycarbonyl-4-piperidyloxy)benzoic acid, 1.59 g (8.32 mmol) of 1-(3-dimethylaminopropyl)-3-ethylcarbodiimide hydrochloride, 1.12 g (8.32 mmol) of 1-hydroxybenzotriazole and 3.16 ml (22.7 mmol) of triethylamine were added to the obtained solution, and they were stirred at room temperature overnight. After the treatment with dichloromethane as the extraction solvent in an ordinary manner, the obtained crude product was purified by the silica gel column chromatography to obtain the title compound.

Yield: 3.0 g (5.33 mmol) (71%)

H-NMR (CDCl3) δ 1.33 (3H, t), 1.47 (9H, s), 1.64–1.79 (2H, m), 1.86–1.98 (2H, m), 3.24–3.42 (2H, m), 3.60–3.73 (2H, m), 3.92 (2H, dt), 4.24 (2H, q), 4.28 (2H, t), 4.45–4.53 (1H, m), 6.57 (1H, d), 6.77 (1H, t), 6.88 (2H, d), 7.18 (1H, d), 7.23 (1H, d), 7.58 (1H, d), 7.77 (2H, d), 7.97 (1H, d)

Step 9: Synthesis of ethyl 3-[4-amidino-2-(2-(4-(1-(1-acetimidoyl)-4-piperidyloxy)benzoylamino)ethoxy)phenyl] acrylate bistrifluoroacetate 3.0 g (5.33 mmol) of ethyl 3-[4-cyano-2-(2-(4-(1-t-butoxycarbonyl-4-piperidyloxy)benzoylamino)ethoxy) phenyl]acrylate was dissolved in a mixture of 4 ml of ethanol and 20 ml of 4 N solution of hydrogen chloride in dioxane, and the obtained solution was stirred at room temperature for 3 days. The solvent was evaporated, and the obtained residue was dissolved in 20 ml of ethanol. 906 mg of ammonium carbonate was added to the obtained solution, and they were stirred at room temperature overnight. The solvent was evaporated, and the obtained residue was dissolved in 20 ml of ethanol. 3.28 g (26.7 mmol) of ethyl acetimidate and 7.42 ml (53.3 mmol) of triethylamine were added to the solution, and they were stirred at room temperature overnight. The solvent was evaporated, and the obtained crude product was subjected to reversed phase high-performance liquid chromatography with silica gel chemically bonded with octadodecyl group as the filler. After the elution with a mixed solution of water and acetonitrile containing 0.1% (v/v) of trifluoroacetic acid, the intended fraction was freeze-dried to obtain the title compound.

Yield: 2.3 g (3.07 mmol) (37%)

MS (ESI, m/z) 522 (MH+)

H-NMR (DMSO-d6) δ 1.23 (3H, t), 1.67–1.87 (2H, m), 2.00–2.25 (2H, m), 2.29 (3H, s), 3.45–3.60 (2H, m), 3.66–3.77 (4H, m), 4.17 (2H, q), 4.34 (2H, t), 4.73–4.76 (1H, m), 6.79 (1H, d), 7.05 (2H, t), 7.43 (1H, d), 7.56 (1H, d), 7.84 (2H, d), 7.92 (1H, br), 7.97 (1H, d), 8.64 (2H, br), 9.19 (1H, br), 9.37 (4H, br)

EXAMPLE 2

Synthesis of 3-[4-amidino-2-(2-(4-(1-(1-acetimidoyl)-4-piperidyloxy)benzoylamino)ethoxy) phenyl]acrylic acid bistrifluoroacetate 550 mg (0.734 mmol) of ethyl 3-[4-amidino-2-(2-(4-(1-(1-acetimidoyl)-4-piperidyloxy)benzoylamino)ethoxy) phenyl]acrylate bistrifluoroacetate was dissolved in 10 ml of concentrated hydrochloric acid, and the obtained solution was stirred at 50° C. for 6 hours. The solvent was evaporated and the obtained crude product was treated in the same manner as that in step 9 in Example 1 to obtain the title compound.

Yield: 440 mg (0.610 mol) (83%)

MS (ESI, m/z) 494 (MH+)

H-NMR (DMSO-d6) δ 1.67–1.87 (2H, m), 2.00–2.17 (2H, m), 2.29 (3H, s), 3.45–3.59 (2H, m), 3.64–3.76 (4H, m), 4.33 (2H, t), 4.73–4.87 (1H, m), 6.70 (1H, d), 7.06 (2H, d), 7.43 (1H, d), 7.54 (1H, br), 7.85 (2H, d), 7.90 (1H, br), 7.95 (1H, d), 8.62 (1H, br), 8.70 (1H, t), 9.17 (1H, br), 9.28 (2H, br), 9.36 (2H, br)

EXAMPLE 3

Synthesis of ethyl 3-[4-amidino-2-(2-(4-(1-(1-acetimidoyl)-4-piperidyloxy)benzoylamino)ethoxy) phenyl]propionate bistrifluoroacetate 1.2 g (1.60 mmol) of ethyl 3-[4-amidino-2-(2-(4-(1-(1-acetimidoyl)-4-piperidyloxy)benzoylamino)ethoxy)phenyl] acrylate bistrifluoroacetate was dissolved in 50 ml of methanol. 100 mg of palladium/carbon was added to the obtained solution, and they were stirred in the presence of hydrogen overnight. The solvent was evaporated and the obtained crude product was treated in the same manner as that in step 9 in Example 1 to obtain the title compound.

Yield: 1.1 g (1.46 mmol) (91%)

MS (ESI, m/z) 524 (MH+)

H-NMR (DMSO-d6) δ 1.16 (3H, t), 1.67–1.76 (2H, m), 2.00–2.25 (2H, m), 2.29 (3H, s), 2.58 (2H, t), 2.90 (2H, t), 3.46–3.58 (2H, m), 3.63–3.84 (4H, m) 3.98 (2H, q), 4.23 (2H, t), 4.74–4.87 (1H, m), 7.08 (1H, d), 7.36 (1H, br), 7.38 (2H, d), 7.84 (2H, d), 8.61 (2H, br), 9.11 (2H, br), 9.16 (1H, br), 9.24 (2H, br)

EXAMPLE 4

Synthesis of 3-[4-amidino-2-(2-(4-(1-(1-acetimidoyl)-4-piperidyloxy)benzoylamino)ethoxy) phenyl]propionic acid bistrifluoroacetate 600 mg (0.799 mmol) of ethyl 3-[4-amidino-2-(2-(4-(1-(1-acetimidoyl)-4-piperidyloxy)benzoylamino)ethoxy) phenyl]propionate bistrifluoroacetate was dissolved in 10 ml of concentrated hydrochloric acid, and the obtained solution was stirred at 50° C. for 4 hours. The solvent was evaporated and the obtained crude product was treated in the same manner as that in step 9 in Example 1 to obtain the title compound.

Yield: 480 mg (0.663 mol) (77%)

MS (ESI, m/z) 496 (MH+)

H-NMR (DMSO-d6) δ 166–1.87 (2H, m), 2.02–2.17 (2H, m), 2.29 (3H, s), 2.52 (2H, t), 2.78 (2H, t), 3.44–3.62 (2H, m), 3.64–3.75 (4H, m), 4.42 (2H, t), 4.74–4.86 (1H, m), 7.06 (2H, d), 7.37 (1H, br), 7.39 (2H, d), 7.85 (2H, d). 8.64 (2H, br), 9.19 (1H, d), 9.23 (2H, br), 9.25 (2H, br)

EXAMPLE 5

Synthesis of ethyl 3-[4-amidino-2-(2-((1-(pyridine-4-yl)piperidine-4-carbonyl)amino)ethoxy)phenyl] propionate bistrifluoroacetate Step 1 Synthesis of ethyl 1-(4-pyridyl)-4-piperidinecarboxylate 4.0 g (26.6 mmol) of 4-chloropyridine hydrochloride, 4.2 g (26.6 mmol) of ethyl piperidine-4-carboxylate and 7.4 ml (53.2 mmol) of triethylamine were stirred in 100 ml of xylene at 130° C. for 24 hours. After the treatment with dichloromethane as the extraction solvent in an ordinary manner, the obtained crude product was purified by the silica gel column chromatography to obtain the title compound.

Yield: 2.95 g (12.6 mmol) (47%)

H-NMR (CDCl3) δ 1.25 (3H, t), 1.71–1.85 (2H, m), 2.00 (2H, d), 2.50–2.60 (1H, m), 2.90 (2H, t), 3.81 (2H, d), 4.20 (2H, q), 6.66 (2H, d), 8.26 (2H, d)

Step 2: Synthesis of 1-(4-pyridyl)-4-piperidinecarboxylic acid hydrochloride 2.95 g (12.6 mmol) of ethyl 1-(4-pyridyl)-4-piperidinecarboxylate was stirred in 100 ml of dioxane. 50 ml of 1 N hydrochloric acid was added to the obtained mixture, and they were stirred at 95° C. for 20 hours. The solvent was evaporated to obtain the crude title compound.

Yield: 3.21 g (11.5 mmol) (91%)

H-NMR (DMSO-d6) δ 1.54 (2H, t), 1.90 (2H, t), 2.60–2.70 (1H, m), 3.30 (2H, t), 4.10 (2H, d), 7.19 (2H, d), 8.20 (2H, d)

Step 3: Synthesis of ethyl 3-[4-cyano-2-(2-((1-(pyridine-4-yl)piperidine-4-carbonyl)amino)ethoxy)phenyl]acrylate 3.0 g (8.33 mmol) of ethyl 3-[2-(2-(t-butoxycarbonylamino)ethoxy)-4-cyanophenyl]acrylate was dissolved in a mixture of 20 ml of 4 N solution of hydrogen chloride in dioxane and 10 ml of dioxane. The obtained solution was stirred at room temperature for 4 hours. The solvent was evaporated and the residue was dissolved in 50 ml of DMF. 2.22 g (9.17 mmol) of 1-(4-pyridyl)-4-piperidinecarboxyic acid hydrochloride, 4.27 g (9.17 mmol) of bromotripyrrolidinophosphonium hexafluorophosphate and 3.48 ml (25.0 mmol) of triethylamine were added to the obtained solution, and they were stirred at room temperature for 3 days. The solvent was evaporated, and the obtained crude product was purified by the silica gel column chromatography to obtain the title compound.

Yield: 2.3 g (5.13 mmol) (62%)

H-NMR (DMSO-d6) δ 1.26 (3H, t); 1.50–1.68 (2H, m), 1.68–1.73 (2H, m), 2.62–2.68 (1H, m), 2.94–3.06 (2H, m), 3.40–3.53 (2H, m), 3.95–4.25 (6H, m),6.76 (1H, dd), 6.94 (2H, d), 7.44 (1H, dd), 7.62 (1H, br), 7.83 (1H, dd), 7.90 (1H, d), 9.01 (1H, t), 8.15 (2H, d)

Step 4: Synthesis of ethyl 3-[4-amidino-2-(2-((1-(pyridine-4-yl)piperidine-4-carbonyl)amino)ethoxy)phenyl]propionate bistrifluoroacetate 2.3 g (5.13 mmol) of ethyl 3-[4-cyano-2-(2-((1-(pyridine-4-yl)piperidine-4-carbonyl)amino)ethoxy)phenyl]acrylate was dissolved in a mixture of 20 ml of 4 N solution of hydrogen chloride in dioxane and 4 ml of ethanol. The obtained solution was stirred at room temperature for 4 days. The solvent was evaporated and the residue was dissolved in 30 ml of ethanol. 872 mg of ammonium carbonate was added to the obtained solution, and they were stirred at room temperature overnight. The solvent was evaporated, and the residue was dissolved in 30 ml of methanol. 200 mg of palladium/carbon was added to the resultant solution, and they were stirred in the presence of hydrogen overnight. The solvent was evaporated, and the obtained crude product was treated in the same manner as that in step 9 in Example 1 to obtain the title compound.

Yield: 1.5 g (2.16 mmol) (42%)

MS (ESI, m/z) 468 (MH+)

H-NMR (DMSO-d6) δ 1.15 (3H, t), 1.50–1.67 (2H, m), 1.76–1.81 (2H, m), 2.52–2.60 (1H, m), 2.62 (2H, dd), 2.89 (2H, dd), 3.15–3.28 (2H, m), 3.49 (2H, dt), 4.03 (2H, q), 4.12 (2H, t), 4.20 (2H, d), 7.19 (2H, d), 7.37 (3H, br), 8.18 (1H, d), 8.21 (2H, d), 9.23 (2H, br), 9.25 (2H, br)

EXAMPLE 6

Synthesis of 3-[4-amidino-2-(2-((1-pyridine-4-yl)piperidine-4-carbonyl)amino)ethoxy)phenyl]propionic acid bistrifluoroacetate 250 mg (0.359 mmol) of ethyl 3-[4-amidino-2-(2-((1-pyridine-4-yl)piperidine-4-carbonyl)amino)ethoxy]phenyl]propionate bistrifluoroacetate was dissolved in 10 ml of concentrated hydrochloric acid, and the obtained solution was stirred at 50° C. for 4 hours. The solvent was evaporated and the obtained crude product was treated in the same manner as that in step 9 in Example 1 to obtain the title compound.

Yield: 480 mg (0.330 mol) (92%)

MS (ESI, m/z) 440 (MH+)

H-NMR (DMSO-d6) δ 1.50–1.67 (2H, m), 1.76–1.92 (2H, m), 2.54 (2H, dd), 2.55–2.67 (1H, m), 2.88 (2H, dd), 3.12–3.29 (2H, m), 3.49 (2H, dt), 4.12 (2H, t), 4.20 (2H, d), 7.18 (2H, d), 7.36 (2H, br), 7.37 (1H, d), 8.18 (1H, d), 8.20 (2H, d), 9.14 (2H, br), 9.24 (2H, br)

EXAMPLE 7

Synthesis of ethyl (3R)-3-[4-amidino-2-(3-ethoxycarbonyl-2-(4-(1-(1-acetimidoyl)-4-piperidyloxy)benzoylamino)propoxy]phenyl]acrylate bistrifluoroacetate Step 1: Synthesis of benzyl (3R)-3-t-butoxycarbonylamino-4-hydroxybutanoate 15.0 g (46.4 mmol) of β-benzyl N-t-butoxycarbonyl-D-aspartate and 6.47 ml (46.4 mmol) of triethylamine were dissolved in 230 ml of tetrahydrofuran. 4.4 ml (46.4 mmol) of ethyl chloroformate was added to the obtained solution under cooling with ice, and they were stirred for 15 minutes. Precipitates thus formed were removed by the filtration under suction. 5 g of ice and 1.8 g (46.6 mmol) of sodium borohydride were added to the filtrate under cooling with ice, and they were stirred for 1.5 hours. Then 200 ml of 1 N aqueous hydrogen chloride solution was added to the reaction mixture, and they were further stirred at room temperature for one hour. After the treatment with ethyl acetate as the extraction solvent in an ordinary manner, the obtained crude product was purified by the silica gel column chromatography to obtain the title compound.

Yield: 10.2 g (32.8 mmol) (71%)

H-NMR (CDCl3) d 1.42 (9H, s), 2.66 (2H, d), 3.65 (2H, dd), 4.00 (1H, ddt), 5.14 (2H, s), 7.35–7.40 (5H, m)

Step 2: Synthesis of benzyl (3R)-3-t-butoxycarbonylamino-4-(5-cyano-2-iodophenoxy)butanoate 10.16 g (32.8 mmol) of benzyl (3R)-3-t-butoxycarbonylamino-4-hydroxybutanoate was dissolved in 100 ml of toluene. 10.5 g (42.7 mmol) of 3-hydroxy-4-iodobenzonitrile, 11.2 g (42.7 mmol) of triphenylphosphine and 7.4 g (42.7 mmol) of N,N,N',N'-tetramethylazodicarboxamide were added to the obtained solution under cooling with ice, and they were stirred at room temperature overnight.

The solvent was evaporated, and the residue was purified by the silica gel column chromatography to obtain the title compound.

Yield: 11.9 g (22.1 mmol) (67%)

H-NMR (CDCl3) d 1.47 (9H, s), 2.90 (2H, t), 4.03 (1H, dd), 4.15 (1H, dd),4.40–4.50 (1H, m), 5.19 (2H, s), 7.01 (1H, d), 7.30 (1H, s), 7.35–7.40 (5H, m), 7.92 (1H, d)

Step 3: Synthesis of ethyl (3R)-3-[2-(3-benzyloxycarbonyl-2-t-butoxycarbonylamino-propoxy)-4-cyanophenyl]acrylate 20.0 g (37.3 mmol) of benzyl (3R)-3-t-butoxycarbonylamino-4-(5-cyano-2-iodophenoxy)butanoate was dissolved in 150 ml of DMF. 10.1 ml (93.3 mmol) of ethyl acrylate, 13 ml (93.3 mmol) of triethylamine and 167 mg (0.567 mmol) of palladium acetate were added to the obtained solution, and they were stirred at 100° C. overnight. After the treatment with ethyl acetate as the extraction solvent in an ordinary manner, the obtained crude product was purified by the silica gel column chromatography to obtain the title compound.

Yield: 13 g (25.6 mmol) (69%)

H-NMR (CDCl3) δ 1.36 (3H, t), 1.44 (9H, s), 2.77–2.84 (2H, m), 4.03–4.22(2H, m), 4.24 (2H, q), 4.37–4.50 (1H, m), 5.16 (2H, s), 6.50 (1H, d), 7.19 (1H, d), 7.23–7.36 (6H, m), 7.61 (1H, d), 7.93 (1H, d)

Step 4: Synthesis of ethyl (3R)-3-[2-(2-amino-3-benzyloxycarbonyl-propoxy)-4-cyanophenyl]acrylate monohydrochloride 13 g (25.6 mmol) of ethyl (3R)-3-[2-(3-benzyloxycarbonyl-2-t-butoxycarbonylamino-propoxy)-4-cyanophenyl]acrylate was dissolved in a mixture of 20 ml of dioxane and 20 ml of 4 N solution of hydrogen chloride in dioxane, and the obtained solution was stirred at room temperature overnight. The solvent was evaporated under reduced pressure to obtain the crude product.

Yield: 7.8 g (17.6 mmol) (69%)

Step 5: Synthesis of ethyl (3R)-3-[2-(3-benzyloxycarbonyl-2-(4-(1-t-butoxycarbonyl-4-piperidyloxy)benzoylamino)propoxy)-4-cyanophenyl]acrylate 3.5 g (7.87 mmol) of ethyl (3R)-3-[2-(2-amino-3-benzyloxycarbonyl-propoxy)-4-cyanophenyl]acrylate monohydrochloride was dissolved in 50 ml of DMF. 2.8 g (8.65 mmol) of 4-(1-t-butoxycarbonyl-4-piperidyloxy) benzoic acid, 1.65 g (8.65 mmol) of 1-(3-dimethylaminopropyl)-3-ethylcarbodiimide hydrochloride, 1.17 g (8.65 mmol) of 1-hydroxybenzotriazole and 3.28 ml (23.6 mmol) of triethylamine were added to the obtained solution, and they were stirred at room temperature overnight. After the treatment with ethyl acetate as the extraction solvent in an ordinary manner, the obtained crude product was purified by the silica gel column chromatography to obtain the title compound.

Yield: 3.2 g (4.50 mmol) (57%)

H-NMR (CDCl3) δ 1.32 (3H, t), 1.47 (9H, s), 1.66–1.83 (3H, m), 1.88–2.02 (2H, m), 2.83–3.07 (2H, m), 3.30–3.42 (2H, m), 3.63–3.78 (2H, m), 4.04–4.25 (2H, m), 4.27 (2H, q), 4.50–4.60 (2H, m), 4.84–4.97 (1H, m), 5.30 (2H, s), 6.52 (1H, d), 6.91 (1H, d), 7.11 (1H, br), 7.29 (7H, br), 7.57 (1H, d), 7.73 (2H, d), 7.92 (1H, d)

Step 6: Synthesis of ethyl (3R)-3-[4-amidino-2-(3-ethoxycarbonyl-2-(4-(1-(1-acetimidoyl)-4-piperidyloxy) benzoylamino)propoxy)phenyl]acrylate bistrifluoroacetate 3.2 g (4.50 mmol) of ethyl (3R)-3-[2-(3-benzyloxycarbonyl-2-(4-(1-t-butoxycarbonyl-4-piperidyloxy)benzoylamino)propoxy)-4-cyanophenyl] acrylate was dissolved in a mixture of 25 ml of 4 N solution of hydrogen chloride in dioxane and 5 ml of ethanol. The obtained solution was stirred at room temperature for 4 days. The solvent was evaporated, and the residue was dissolved in 20 ml of ethanol. 760 mg of ammonium carbonate was added to the obtained solution, and they were stirred at room temperature overnight. The solvent was evaporated, and the obtained residue was dissolved in 50 ml of ethanol. 3.0 g (26.7 mmol) of ethyl acetimidate and 5 ml (35.6 mmol) of triethylamine were added to the obtained solution, and they were stirred at room temperature overnight. The solvent was evaporated, and the obtained crude product was treated in the same manner as that in step 9 in Example 1 to obtain the title compound.

Yield: 550 mg (0.659 mmol) (17%)

MS (ESI, m/z) 608 (MH+)

H-NMR (DMSO-d6) δ 1.14 (3H, t), 1.22 (3H, t), 1.68–1.76 (2H, m), 2.00–2.16 (2H, m), 2.29 (3H, s), 2.80 (2H, d), 3.47–3.60 (2H, m), 3.70–3.85 (2H, m), 4.05 (2H, q), 4.14 (2H, q), 4.23–4.35 (2H, m), 4.70–4.88 (2H, m), 6.77 (1H, d), 7.06 (2H, d), 7.43 (1H, d), 7.56 (1H, br), 7.82 (2H, d), 7.87 (1H, d), 7.97 (1H, d), 8.50 (1H, d), 8.60 (1H, br), 9.15 (1H, br), 9.23 (2H, br), 9.35 (2H, br)

EXAMPLE 8

Synthesis of (3R)-3-[4-amidino-2-(3-ethoxycarbonyl-2-(4-(1-(1-acetimidoyl)-4-piperidyloxy)benzoylamino)propoxy)phenyl]acrylic acid bistrifluoroacetate 200 mg (0.240 mmol) of ethyl (3R)-3-[4-amidino-2-(3-ethoxycarbonyl-2-(4-(1-(l1-acetimidoyl)-4-piperidyloxy) benzoylamino)propoxy)phenyl]acrylate bistrifluoroacetate was dissolved in 5 ml of concentrated hydrochloric acid, and the obtained solution was stirred at 50° C. for 2 hours. The solvent was evaporated, and the obtained crude product was treated in the same manner as that in step 9 in Example 1 to obtain the title compound.

Yield: 120 mg (0.154 mmol) (64%)

MS (ESI, m/z) 552 (MH+)

H-NMR (DMSO-d6) δ 1.70–1.85 (2H, m), 2.00–2.14 (2H, m), 2.29 (3H, s), 2.78 (2H, d), 3.71–3.84 (2H, m), 4.22–4.34 (2H, m), 4.29 (2H, d), 4.62–4.73 (1H, m), 4.77–4.86 (1H, m), 6.68 (1H, d), 7.06 (2H, d), 7.43 (1H, d), 7.56 (1H, br), 7.82 (2H, d), 7.86 (1H, d), 7.94 (1H, d), 8.50 (1H, d), 8.62 (1H, br), 9.17 (1H, br), 9.31 (2H, br), 9.32 (2H, br)

EXAMPLE 9

Synthesis of ethyl (3R)-4-[5-amidino-2-(2-ethoxycarbonylethyl)phenoxy]-3-[4-(1-(1-acetimidoyl)-4-piperidyloxy)benzoylamino] butanoate bistrifluoroacetate 3.2 g (4.50 mmol) of ethyl (3R)-3-[2-(3-benzyloxycarbonyl-2-(4-(1-t-butoxycarbonyl-4-piperidyloxy)benzoylamino)propoxy)-4-cyanophenyl] acrylate was dissolved in a mixture of 25 ml of 4 N solution of hydrogen chloride in dioxane and 5 ml of ethanol. The obtained solution was stirred at room temperature for 4 days. The solvent was evaporated, and the residue was dissolved in 20 ml of ethanol. 765 mg of ammonium carbonate was added to the obtained solution, and they were stirred at room temperature overnight. The solvent was evaporated, and the obtained residue was dissolved in 50 ml of ethanol. 2.77 g (26.7 mmol) of ethyl acetimidate and 5 ml (35.6 mmol) of triethylamine were added to the obtained solution, and they were stirred at room temperature overnight. The solvent was evaporated, and the obtained crude product was dissolved in 50 ml of water containing 0.1% (v/v) of trifluoroacetic acid and then purified by the reversed phase medium-pressure preparative chromatography with silica gel packing material (LiChroprep RP-18 37×440 mm) chemically bonded to octadodecyl group, followed by the elution with a mixed solvent of water and acetonitrile containing 0.1% (v/v) of trifluoroacetic acid. The obtained purified product was dissolved in 50 ml of methanol. 600 mg of palladium/carbon was added to the obtained solution, and they were stirred in the presence of hydrogen overnight. The solvent was evaporated and the obtained crude product was treated in the same manner as that in step 9 in Example 1 to obtain the title compound.

Yield: 920 mg (1.10 mmol) (24%)

MS (ESI, m/z) 608 (MH+)

H-NMR (DMSO-d6) δ 1.13 (3H, t), 1.15 (3H, t), 1.67–1.86 (2H, m), 2.00–2.16 (2H, m), 2.29 (3H, s), 2.56 (2H, dd), 2.82 (2H, dd), 2.83–2.98 (2H, m), 3.47–3.62 (2H, m), 3.64–3.92 (2H, m), 3.98 (2H, q), 4.06 (2H, q), 4.18 (2H, d), 4.67–4.88 (2H, m), 7.06 (2H, d), 7.37 (1H, br), 7.38 (2H, d), 7.82 (2H, d), 8.45 (1H, d), 8.62 (1H, br), 9.11 (2H, br), 9.16 (1H, br), 9.23 (2H, br)

EXAMPLE 10

Synthesis of (3R)-4-[5-amidino-2-(2-carboxyethyl) phenoxy]-3-[4-(1-(1-acetimidoyl)-4-piperidyloxy) benzoylamino]butanoic acid bistrifluoroacetate 500 mg (0.600 mmol) of ethyl (3R)-4-[5-amidino-2-(2-ethoxycarbonylethyl)phenoxy]-3-[4-(1-(1-acetimidoyl)-4-piperidyloxy)benzoylamino]butanoate bistrifluoroacetate was dissolved in 5 ml of concentrated hydrochloric acid, and the obtained solution was stirred at 50° C. for 2 hours. The solvent was evaporated, and the obtained crude product was treated in the same manner as that in step 9 in Example 1 to obtain the title compound.

Yield: 340 mg (0.435 mmol) (73%)

MS (ESI, m/z) 554 (MH+)

H-NMR (DMSO-d6) δ 1.68–1.86 (2H, m), 2.00–2.17 (2H, m), 2.29 (3H, s), 2.52 (2H, d), 2.76 (2H, dd), 2.83–2.96 (2H, m), 3.48–3.52 (2H, m), 3.69–3.76 (2H, m), 4.12–4.24 (2H, m), 4.63–4.73 (1H, m), 4.75–4.86 (1H, m), 7.06 (2H, d), 7.37 (1H, br), 7.39 (2H, d), 7.83 (2H, d), 8.44 (1H, d), 8.61 (1H, br), 9.09 (2H, br), 9.15 (1H, br), 9.22 (2H, br)

EXAMPLE 11

Synthesis of 3-[4-amidino-2-(2-(4-(1-acetimidoyl-4-piperidyloxy)benzoylamino)ethoxy)phenyl] acrylamide bistrifluoroacetate Step 1: Synthesis of 3-[4-cyano-2-(2-(4-(1-t-butoxycarbonyl-4-piperidyloxy)benzoylamino)ethoxy) phenyl]acrylamide 3.0 g (5.33 mmol) of ethyl 3-[4-cyano-2-(2-(4-(1-t-butoxycarbonyl-4-piperidyloxy)benzoylamino)ethoxy)

phenyl]acrylate was dissolved in 100 ml of ethanol. 15 ml of 1 N aqueous sodium hydroxide solution was added to the obtained solution, and they were stirred at room temperature overnight. The solvent was evaporated under reduced pressure. 1 N aqueous hydrochloric acid/ice solution was added to the obtained crude product, and they were treated with ethyl acetate as the extraction solvent in an ordinary manner to obtain the crude product. 30 ml of N,N-dimethylformamide, 0.75 g (5.55 mmol) of 1-hydroxybenzotriazole (hydrous), 1.40 g (25.2 mmol) of ammonium carbamate, 2 ml (0.015 mmol) of triethylamine and 2.12 g (11.09 mmol) of 1-(3-dimethylaminopropyl)-3-ethylcarbodiimide hydrochloride were added to the crude product, and they were stirred overnight. After the evaporation of the solvent followed by the treatment with ethyl acetate as the extraction solvent in an ordinary manner, the solvent was evaporated, and the obtained crude product was purified by the silica gel column chromatography to obtain the title compound.

Yield: 1.89 g (3.54 mmol) (66%)

H-NMR (CDCl3) δ 1.45 (9H, s), 1.60–2.00 (4H, m), 3.28–3.73 (4H, m), 4.02–4.23 (4H, m), 4.51 (1H, br), 5.60 (1H, br), 6.89 (2H, d), 7.00–7.68 (5H, m), 7.75 (2H, d)

Step 2: Synthesis of 3-[4-amidino-2-(2-(4-(1-acetamidoyl-benzoylamino)-4-piperidyloxy)ethoxy)phenyl]acrylamide bistrifluoroacetate 1.89 g (3.54 mmol) of 3-[4-cyano-2-(2-(4-(1-t-butoxycarbonyl-4-piperidyloxy)benzoylamino)ethoxy) phenyl]acrylamide was dissolved in a mixture of 40 ml of 4 N solution of hydrogen chloride in dioxane and 4 ml of ethanol, and they were stirred at room temperature overnight. The solvent was evaporated under reduced pressure, and the residue was dissolved in 60 ml of ethanol. 0.97 g (17.15 mmol) of ammonium carbamate was added to the obtained solution, and they were stirred at room temperature overnight. The solvent was evaporated, and the obtained crude product was treated in the same manner as that in step 9 in Example 1 to obtain the purified product. 1.86 g (3.37 mmol) of the purified product was dissolved in 30 ml of ethanol. 1.27 g (10.29 mmol) of ethyl acetimide hydrochloride and 2.4 ml (17.15 mmol) of triethylamine were added to the obtained solution, and they were stirred overnight. The solvent was evaporated, and the obtained crude product was treated in the same manner as that in step 9 in Example 1 to obtain the title compound.

Yield: 1.10 g (1.53 mmol) (43%)

MS (ESI,m/z) 493 (MH+)

H-NMR (DMSO) δ 1.68–2.18 (4H, m), 2.29 (3H, s), 3.45–3.90 (6H, m), 4.30 (2H, t), 4.80 (1H, br), 6.92 (1H, d), 7.10 (2H, d), 7.23 (1H, br), 7.45 (1H, d), 7.52 (1H, s), 7.62 (1H, d), 7.64 (1H, br), 7.74 (1H, d), 7.85 (2H, d), 8.62 (1H, br), 8.74 (1H, t), 9.16 (1H, br), 9.22–9.42 (4H, m)

EXAMPLE 12

Synthesis of 3-[4-amidino-2-(2-(4-(1-acetamidoyl)-4-piperidyloxy)benzoylamino)ethoxy)phenyl] propionamide bistrifluoroacetate 1.10 g (1.53 mmol) of 3-[4-amidino-2-(2-(4-(1-acetimidoyl)benzoylamino)ethoxy)phenyl]acrylamide bistrifluoroacetate was dissolved in 100 ml of ethanol. 220 mg of 10% palladium/carbon (50% hydrous) was added to the obtained solution, and they were stirred in the presence of hydrogen overnight. The reaction solution was filtered through Celite. The solvent was evaporated, and the obtained crude product was treated in the same manner as that in step 9 in Example 1 to obtain the title compound.

Yield: 0.82 g (1.13 mmol) (74%)

MS (ESI,m/z) 495 (MH+)

H-NMR (DMSO) δ 1.68–2.17 (4H, m), 2.28 (3H, s), 2.35 (2H, t), 2.85 (2H, t), 3.47–3.85 (6H, m), 4.20 (2H, t), 4.80 (1H, br), 6.80 (1H, br), 7.06 (2H, d), 7.30 (1H, br), 7.33–7.42 (3H, m), 7.85 (2H, d), 8.56–8.70 (2H, m), 9.07–9.28 (5H, m)

EXAMPLE 13

Synthesis of (3R)-4-[5-amidino-2-(2-carboxyethyl) phenoxy]-3-[(1-(pyridine-4-yl)piperidine-4-carbonyl)amino]butanoic acid bistrifluoroacetate Step 1: Synthesis of ethyl (3R)-3-[2-(3-benzyloxycarbonyl-2-((1-(pyridine-4-yl)piperidine-4-carbonyl)amino) propoxy)-4-cyanophenyl]acrylate 7.50 g (14.7 mmol) of ethyl (3R)-3-[2-(t-butoxycarbonylamino)-3-benzyloxycarbonyl-propoxy]-4-cyanophenyl]acrylate was dissolved in a mixture of 14.7 ml of dioxane and 22.1 ml of 4 N solution of hydrogen chloride in dioxane, and the obtained solution was stirred at room temperature for 4 hours. The solvent was evaporated. 6.73 g (of 7.08 g in total) of the crude product obtained by evaporating the solvent was dissolved in 70 ml of DMF. 3.74 g (15.4 mmol) of 1-(4-pyridyl)-4-piperidinecarboxylic acid hydrochloride, 3.08 g (18.2 mmol) of 2-chloro-1,3-dimethylimidazonium chloride and 8.6 ml (61.6 mmol) of triethylamine were added to the obtained solution at 10° C., and they were stirred for 16 hours.

After the treatment with ethyl acetate as the extraction solvent in an ordinary manner, the obtained crude product was purified by the silica gel column chromatography to obtain the title compound.

MS (HRFABH+) 597.27 (MH+)

Yield: 7.83 g (13.1 mmol) (94%)

H-NMR (DMSO) δ 1.23 (3H, t), 1.50–1.64 (2H, m), 1.69–1.83 (2H, m), 2.42–2.51 (1H, m), 2.62–2.77 (2H, m), 3.03–3.41 (2H, m), 4.06–4.38 (6H, m), 4.49–4.61 (1H, m). 5.10 (2H, s), 6.74 (1H, d), 7.08 (2H, d), 7.36 (5H, br), 7.45 (1H, d), 7.62 (1H, br), 7.83 (1H, d), 7.92 (1H, d), 8.18 (3H,brd), Step 2: Synthesis of (3R)-4-[5-amidino-2-(2-carboxyethyl) phenoxy]-3-[(1-(pyridine-4-yl)piperidine-4-carbonyl) amino]butanoic acid bistrifluoroacetate 5.37 g (9.0 mmol) of ethyl (3R)-3-[2-(3-benzyloxycarbonyl-2-((1-pyridine-4-yl)piperidine-4-carbonyl)amino)propoxy]-4-cyanophenyl]acrylate was dissolved in a mixture of 45 ml of 4 N solution of hydrogen chloride in dioxane and 9 ml of ethanol, and the obtained solution was stirred at room temperature overnight. The solvent was evaporated under reduced pressure, and the residue was dissolved in 36 ml of ethanol. 1.56 g (16.2 mmol) of ammonium carbonate was added to the obtained solution, and they were stirred at room temperature overnight. The solvent was evaporated. 5.48 g (of 6.09 g in total) of the crude product obtained by the evaporation of the solvent was dissolved in 54 ml of methanol. 548 mg of 10% palladium/carbon was added to the obtained solution, and they were stirred in the presence of hydrogen overnight. The reaction solution was filtered through Celite. The solvent was evaporated, and 3.11 g (of 4.44 g in total) of the crude product obtained by the evaporation of the solvent was dissolved in 28 ml of 6 N aqueous hydrochloric acid solution. After stirring the obtained solution at 60° C. for 2 hours, the solvent was evaporated. 60% of the crude product obtained by the evaporation of the solvent was treated in the same manner as that in step 9 in Example 1 to obtain the title compound.

MS (ESI, m/z) 498 (MH+)

MS (HRFABH+) 498.24(MH+)

Yield: 1.34 g (1.85 mmol) (33%)

H-NMR (DMSO) δ 1.52–1.64 (2H, m), 1.78–1.88 (2H, m), 2.50–2.639 (5H, m), 2.81–2.96 (2H, m), 3.17–3.24 (2H, m), 4.07–4.23 (4H, m), 4.40–4.51 (1H, m). 7.19 (2H, d), 7.38 (3H, br), 8.17 (1H, d), 8.23 (2H, d), 9.26 (2H, br), 9.43 (2H, br)

EXAMPLE 14

Synthesis of N-[2-(5-amidino-2-hydroxyphenoxy)ethyl]-4-(1-acetimidoyl-4-piperidyloxy)benzamide bistrifluoroacetate Step 1: Synthesis of 4-benzyloxy-3-hydroxybenzonitrile 1.0 g (7.41 mmol) of 3,4-dihydroxybenzonitrile was dissolved in 10 ml of N,N-dimethylformamide. 1.12 g (8.15 mmol) of potassium carbonate and 0.88 ml (7.41 mmol) of benzyl bromide were added to the obtained solution, and they were stirred at 50° C. for 2 hours. After the treatment with ethyl acetate as the extraction solvent in an ordinary manner, the solvent was evaporated, and the obtained residue was purified by the silica gel column chromatography to obtain the title compound.

Yield: 1.06 g (4.71 mmol) (64%)

H-NMR (CDCl3) δ 5.17 (2H, s), 6.95 (1H, d), 7.18 (1H, d), 7.20 (1H, d), 7.41 (5H, br)

Step 2: Synthesis of 4-benzyloxy-3-[2-(t-butoxycarbonylamino)ethoxy]benzonitrile 8.0 g (35.7 mmol) of t-butyl (2-bromoethyl)carbamate was dissolved in 20 ml of DMF. 4.0 g (17.7 mmol) of 4-benzyloxy-3-hydroxybenzonitrile and 7.4 g (41.3 mmol) of potassium carbonate were added to the obtained solution, and they were stirred at 100° C. for 3 hours. After the treatment with ethyl acetate as the extraction solvent in an ordinary manner, the solvent was evaporated, and the obtained residue was purified by the silica gel column chromatography to obtain the title compound.

Yield: 3.4 g (9.2 mmol) (52%)

H-NMR (CDCl3) δ 1.46 (9H, s), 3.74 (2H, dt), 4.11 (2H, t), 5.15 (2H, d), 7.18 (1H, d), 7.20 (1H, d), 7.41 (5H, br)

Step 3: Synthesis of 3-(2-aminoethoxy)-4-benzyloxybenzonitrile 3.4 g (9.2 mmol) of 4-benzyloxy-3-[2-(t-butoxycarbonylamino)ethoxy]benzonitrile was dissolved in 40 ml of 4 N solution of hydrogen chloride in dioxane, and the obtained solution was stirred overnight. The solvent was evaporated to obtain hydrochloride of the crude title compound.

Yield: 3.0 g

Step 4: Synthesis of N-[2-(5-cyano-2-benzyloxyphenoxy)ethyl]-4-(1-t-butoxycarbonyl-4-piperidyloxy)benzamide 1.06 g (3.50 mmol) of 3-(2-aminoethoxy)-4-benzyloxybenzonitrile hydrochloride was dissolved in 15 ml of DMF. 1.23 g (3.84 mmol) of 4-(1-t-butoxycarbonyl-4-piperidyloxy)benzoic acid, 710 mg (4.2 mmol)) of 2-chloro-1,3-dimethylimidazonium chloride and 1.45 ml (5.19 mmol) of triethylamine were added to the obtained solution, and they were stirred overnight. After the treatment with dichloromethane as the extraction solvent in an ordinary manner, the solvent was evaporated, and the obtained residue was purified by the silica gel column chromatography to obtain the title compound.

Yield: 510 mg (0.89 mmol) (26%)

H-NMR (CDCl3) δ 1.47 (9H, s), 1.66–1.80 (2H, m), 1.83–1.97 (2H, m), 3.25–3.41 (2H, m), 3.61–3.73 (2H, m), 3.84 (2H, dt), 4.20 (2H, t), 4.44–4.53 (1H, m), 5.16 (2H, d), 6.62 (1H, t), 6.84 (2H, d), 6.95 (1H, d), 7.15 (1H, d), 7.24 (1H, d), 7.28–7.42 (5H, m), 7.65 (2H, d)

Step 5: Synthesis of N-[2-(5-amidino-2-hydroxyphenoxy)ethyl]-4-(4-piperidyloxy)benzamide bistrifluoroacetate 510 mg (0.89 mmol) of N-[2-(5-cyano-2-benzyloxyphenoxy)ethyl]-4-(1-t-butoxycarbonyl-4-piperidyloxy)benzamide was dissolved in a mixture of 5 ml of 4 N solution of hydrogen chloride in dioxane and 1 ml of ethanol, and the obtained solution was stirred for 3 days. The solvent was evaporated, and the obtained crude product was dissolved in 10 ml of ethanol. 500 mg of ammonium carbonate was added to the obtained solution, and they were stirred overnight. The solvent was evaporated, and the obtained crude product was dissolved in 10 ml of ethanol. 50 mg of 10% palladium/carbon was added to the obtained solution, and they were stirred in the presence of hydrogen overnight. The reaction solution was filtered through Celite. The solvent was evaporated, and the obtained crude product was treated in the same manner as that in step 9 in Example 1 to obtain the title compound.

Yield: 300 mg (0.479 mmol) (54%)

MS (ESI,m/z) 399 (MH+)

H-NMR (DMSO) δ 1.68–1.87 (2H, m), 2.03–2.17 (2H, m), 3.02–3.16 (2H, m), 3.19–3.30 (2H, m), 3.65 (2H, dt), 4.14 (2H, t), 4.46–4.78 (1H, m), 6.95 (1H, d), 7.05 (2H, d), 7.36 (1H, d), 7.42 (1H, br), 7.82 (2H, d), 8.57 (1H, br), 8.84 (2H, br), 9.02 (2H, br)

Step 6: Synthesis of N-[2-(5-amidino-2-hydroxyphenoxy)ethyl]-4-(1-acetimidoyl-4-piperidyloxy)benzamide bistrifluoroacetate 300 mg (0.479 mmol) of N-[2-(5-amidino-2-hydroxyphenoxy)ethyl]-4-(4-piperidyloxy)benzamide bistrifluoroacetate was dissolved in 10 ml of ethanol. 500 mg (5.3 mmol) of ethyl acetimidate and 0.5 ml (3.5 mmol) of triethylamine were added to the obtained solution, and they were stirred at room temperature overnight. The solvent was evaporated, and the obtained crude product was treated in the same manner as that in step 9 in Example 1 to obtain the title compound.

Yield: 220 mg (0.33 mmol) (69%)

MS (ESI,m/z) 440 (MH+)

H-NMR (DMSO) δ 1.63–1.84 (2H, m), 1.99–2.10 (2H, m), 2.27 (1H, s), 3.40–3.56 (4H, m), 3.65 (2H, dt), 3.66–3.81 (2H, m), 4.14 (2H, t), 4.66–4.87 (1H, m), 6.96 (1H, d), 7.06 (2H, d), 7.37 (1H, d), 7.42 (1H, br), 7.82 (2H, d), 8.58 (1H, t), 8.62 (1H, br), 8.94 (2H, br), 9.03 (2H, br), 9.16 (1H, br)

EXAMPLE 15

Synthesis of N-[2-(5-amidino-2-hydroxyphenoxy)ethyl]-1-(4-pyridyl)-4-piperidine-4-carboxamide bistrifluoroacetate 1.00 g (3.30 mmol) of 3-(2-aminoethoxy)-4-benzyloxybenzonitrile hydrochloride was dissolved in 15 ml of DMF. 876 mg (3.62 mmol) of 1-(4-pyridyl)-4-piperidinecarboxylic acid hydrochloride, 837 mg (4.95 mmol) of 2-chloro-1,3-dimethylimidazonium chloride and 1.4 ml (9.9 mmol) of triethylamine were added to the obtained solution, and they were stirred overnight. After the treatment with dichloromethane as the extraction solvent in an ordinary manner, the solvent was evaporated, and the obtained residue was dissolved in a mixture of 10 ml of 4 N solution of hydrogen chloride in dioxane and 2 ml of ethanol. The obtained solution was stirred for 3 days. The solvent was evaporated, and the obtained crude product was dissolved in 10 ml of ethanol. 500 mg of ammonium carbonate was added to the solution, and they were stirred overnight. The solvent was evaporated, and the obtained crude product was dissolved in 10 ml of ethanol. 50 mg of 10% palladium/carbon was added to the obtained solution, and they were stirred in the presence of hydrogen overnight. The reaction solution was filtered through Celite. The solvent was evaporated and the residue was treated in the same manner as that in step 9 in Example 1 to obtain the title compound.

Yield: 50 mg (0.082 mmol) (3%)

MS (ESI,m/z) 383 (MH+)

H-NMR (DMSO) δ 1.46–1.64 (2H, m), 1.75–1.91 (2H, m), 2.48–2.55 (2H, m), 3.04–3.26 (2H, m), 3.46 (2H, dt), 4.04 (2H, t), 4.17–4.29 (1H, m), 6.96 (1H, d), 7.12 (1H, d), 7.18 (2H, d), 7.27 (1H, br), 8.19 (1H, t), 8.20 (2H, d), 8.95 (1H, br), 8.98 (1H, br), 9.03 (1H, br), 9.05 (1H, br)

EXAMPLE 16

Synthesis of 3-[4-amidino-2-(3-((1-(pyridine-4-yl) piperidine-4-carbonyl)amino)propoxy)phenyl] propionic acid bistrifluoroacetate Step 1: Synthesis of t-butyl (3-bromopropyl)carbamate The title compound was obtained from 18.4 g (84.2 mmol) of 3-bromopropylamine hydrobromide and 13.1 g (60 mmol) of di-t-butyl dicarbonate in the same manner as that in step 5 in Example 1 to obtain the title compound.

Yield: 11.8 g (50.0 mmol) (83%)

H-NMR (CDCl3) δ 1.42 (9H, s), 2.05 (2H, tt), 3.25 (2H, dt), 3.45 (2H, t), 4.70 (1H, br)

Step 2: Synthesis of 3-[3-(t-butoxycarbonylamino) propoxy]-4-iodobenzonitrile 10.0 g (42 mmol) of t-butyl (3-bromopropyl))carbamate was dissolved in 100 ml of DMF. 5.1 g (21 mmol) of 3-hydroxy-4-iodobenzonitrile and 8.7 g (41.3 mmol) of potassium carbonate were added to the obtained solution, and they were stirred at 100° C. for 2 hours. After the treatment with ethyl acetate as the extraction solvent in an ordinary manner, the obtained crude product was purified by the silica gel column chromatography to obtain the title compound.

Yield: 8.2 g (20.4 mmol) (98%)

H-NMR (CDCl3) δ 1.46 (9H, s), 2.04 (2H, tt), 3.39 (2H, t), 4.12 (2H, t), 6.98 (2H, br), 7.88 (1H, d).

Step 3: Synthesis of ethyl 3-[2-(3-(t-butoxycarbonylamino) propoxy)-4-cyanophenyl]acrylate 4.5 g (11.2 mmol) of 3-[3-(t-butoxycarbonylamino) propoxy]-4-iodobenzonitrile was dissolved in 20 ml of DMF. 6.0 ml (56 mmol) of ethyl acrylate, 6.2 ml (56 mmol) of triethylamine and 56 mg (0.22 mmol) of palladium acetate were added to the obtained solution, and they were stirred at 100° C. overnight. After the treatment with ethyl acetate as the extraction solvent in an ordinary manner, the obtained crude product was purified by the silica gel column chromatography to obtain the title compound.

Yield: 3.8 g (10.2 mmol) (91%)

H-NMR (CDCl3) δ 1.33 (3H, t), 1.43 (9H, s), 2.08 (2H, tt), 3.37 (2H, dt), 4.11 (2H, t), 4.26 (2H, q), 6.54 (1H, d), 7.14 (1H, br), 7.24 (1H, d), 7.56 (1H, d), 7.91 (1H, d)

Step 4: Synthesis of ethyl 3-[2-(3-aminopropoxy)-4-cyanophenyl]propionate 3.8 g (10.2 mmol) of ethyl 3-[2-(3-(t-butoxycarbonylamino)propoxy)-4-cyanophenyl]acrylate was dissolved in 100 ml of ethyl acetate. 700 mg of 10% palladium/carbon (50% hydrous) was added to the obtained solution, and they were stirred in the presence of hydrogen for 3 hours. The reaction solution was filtered through Celite. The solvent was evaporated, and the obtained crude product was dissolved in 50 ml of 4 N solution of hydrogen chloride in dioxane. The obtained solution was stirred overnight. The solvent was evaporated to obtain hydrochloride of the crude title compound.

Yield: 2.4 g (7.5 mmol) (74%)

Step 5: Synthesis of 3-[4-cyano-2-(3-((1-(pyridine-4-yl) piperidine-4-carbonyl)amino)propoxy)phenyl]propionic acid bistrifluoroacetate 1.06 g (3.33 mmol) of ethyl 3-[2-(3-aminopropoxy)-4-cyanophenyl]propionate hydrochloride was dissolved in 10 ml of DMF. 887 mg (3.6 mmol) of 1-(4-pyridyl)-4-piperidinecarboxylic acid hydrochloride, 844 mg (5.0 mmol) of 2-chloro-1,3-dimethylimidazonium chloride and 1.4 ml (9.9 mmol) of triethylamine were added to the obtained solution, and they were stirred overnight. The solvent was evaporated, and the obtained crude product was dissolved in a mixture of 20 ml of 4 N solution of hydrogen chloride in dioxane and 4 ml of ethanol, and they were stirred for 3 days. The solvent was distilled off, and the obtained crude product was dissolved in 20 ml of ethanol. 1000 mg of ammonium carbonate was added to the obtained solution, and they were stirred overnight. The solvent was evaporated, and the obtained crude product was dissolved in 10 ml of 6 N aqueous hydrochloric acid solution, and the obtained solution was stirred at 50° C. for 2 hours. The solvent was evaporated, and the obtained crude product was treated in the same manner as that in step 9 in Example 1 to obtain the title compound.

Yield: 660 mg (0.97 mmol) (29%)

MS (ESI,m/z) 454 (MH+)

H-NMR (DMSO-d6) δ 1.46–1.66 (2H, m), 1.46–1.98 (4H, m), 2.48 (2H, br), 2.52 (2H, t), 2.85 (2H, t), 3.18–3.27 (4H, m), 4.08 (2H, t), 4.20 (1H, br), 7.17 (1H, d), 7.32 (2H, d), 7.36 (1H, d), 8.00 (1H, t), 8.19 (2H, d), 9.20 (2H, br) 9.24 (2H, br)

EXAMPLE 17

Synthesis of 3-[4-amidino-2-(2-((1-(2,3,5,6-tetrafluoropyridine-4-yl)piperidine-4-carbonyl) amino)ethoxy)phenyl]propionic acid bistrifluoroacetate:

Step 1: Synthesis of ethyl 1-(2,3,5,6-tetrafluoropyridyl-4-yl)-4-piperidinecarboxylate 1.1 g (6.5 mmol) of pentafluoropyridine, 1.1 g (6.5 mmol) of ethyl piperidine-4-carboxylate and 2.27 ml (13.7 mmol) of diisopropylethylamine were stirred in 5 ml of ethanol at room temperature for 24 hours. After the treatment with ethyl acetate as the extraction solvent in an ordinary manner, the obtained crude product was purified by the silica gel column chromatography to obtain the title compound.

Yield: 2.0 g (6.5 mmol) (100%)

H-NMR (CDCl3) δ 1.25 (3H, t), 1.78–1.93 (2H, m), 1.98–2.09 (2H, m), 2.46–2.60 (1H, m) 3.25 (2H, t), 3.69 (2H, d), 4.17 (2H, q)

Step 2: Synthesis of 1-(2,3,5,6-tetrafluoropyridyl-4-yl)-4-piperidinecarboxylic acid hydrochloride 2.0 g (6.5 mmol) of ethyl 1-(2,3,5,6-tetrafluoropyridyl-4-yl)-4-piperidinecarboxylate was stirred in 5 ml of dioxane. 5 ml of 2 N hydrochloric acid was added to the obtained mixture, and they were stirred at 95° C. for 2 hours. The solvent was evaporated to obtain the crude title compound.

Yield: 1.5 g (4.7 mmol) (73%)

Step 3: Synthesis of 3-[4-amidino-2-(2-((1-(2,3,5,6-tetrafluoropyridine-4-yl)piperidine-4-carbonyl)amino) ethoxy)phenyl]propionic acid bistrifluoroacetate 600 mg (2.15 mmol) of ethyl 3-[2-(2-aminoethoxy)-4-cyanophenyl]propionate hydrochloride was dissolved in 10 ml of DMF. 812 mg (2.6 mmol) of 1-(2,3,5,6-tetrafluoropyridyl-4-yl)-4-piperidinecarboxylic acid hydrochloride, 560 mg (3.3 mmol) of 2-chloro-1,3-dimethylimidazonium chloride and 0.9 ml (6.5 mmol) of triethylamine were added to the obtained solution, and they were stirred overnight. The solvent was evaporated, and the obtained crude product was dissolved in a mixture of 5 ml of 4 N solution of hydrogen chloride in dioxane and 1 ml of ethanol, and they were stirred for 3 days. The solvent was distilled off, and the obtained crude product was dissolved in 20 ml of ethanol. 500 mg of ammonium carbonate was added to the obtained solution, and they were stirred overnight. The solvent was evaporated, and the obtained crude product was dissolved in 10 ml of 6 N aqueous hydrochloric acid solution, and the obtained solution was stirred at 50° C. for 2 hours. The solvent was evaporated, and the obtained crude product was treated in the same manner as that in step 9 in Example 1 to obtain the title compound.

Yield: 100 mg (0.14 mmol) (5%)

MS (ESI,m/z) 512 (MH+)

H-NMR (DMSO-d6) δ 1.58–1.81 (4H, m), 2.33–2.41 (1H, m), 2.54 (2H, t), 2.86 (2H, t), 3.12–3.23 (2H, m), 3.47 (2H, t), 3.66 (2H, d), 4.11 (2H, t), 7.31–7.38 (3H, d), 8.13 (1H, t), 9.00 (2H, br), 9.22 (2H, br)

EXAMPLE 18

Synthesis of 3-[4-amidino-2-(2-((1-(pyridine-4-ylmethyl)piperidine-4-carbonyl)amino)ethoxy) phenyl]propionic acid bistrifluoroacetate Step 1: Synthesis of ethyl 1-(pyridyl-4-ylmethyl)-4-piperidinecarboxylate 1.15 g (7.0 mmol) of picolyl chloride hydrochloride, 1.0 g (6.4 mmol) of ethyl piperidine-4-carboxylate and 1.3 ml (9.6 mmol) of triethylamine were stirred in 10 ml of DMF at room temperature for 4 hours. After the treatment with ethyl acetate as the extraction solvent in an ordinary manner, the obtained crude product was purified by the silica gel column chromatography to obtain the title compound.

Yield: 1.0 g (3.51 mmol) (55%)

H-NMR (CDCl3) δ 1.25 (3H, t), 1.64–1.96 (4H, m), 2.02–2.17 (2H, m), 2.22–2.40 (1H, m) 2.80 (2H, d), 3.49 (2H, s), 4.13 (2H, q)

Step 2: Synthesis of 3-[4-amidino-2-(2-((1-(pyridine-4-ylmethyl)piperidine-4-carbonyl)amino)ethoxy)phenyl] propionic acid bistrifluoroacetate 1.0 g (3.51 mmol) of ethyl 1-(pyridyl-4-ylmethyl)-4-piperidinecarboxylate was stirred in 10 ml of dioxane. 10 ml of 2 N hydrochloric acid was added to the obtained mixture, and they were stirred at 95° C. for 4 hours. The solvent was evaporated, and the obtained crude product was dissolved in 10 ml of DMF. 812 mg (2.9 mmol) of ethyl 3-[2-(2-aminoethoxy)-4-cyanophenyl]propionate hydrochloride, 735 mg (4.35 mmol) of 2-chloro-1,3-dimethylimidazonium chloride and 1.2 ml (8.7 mmol) of triethylamine were added to the obtained solution, and they were stirred overnight. The solvent was evaporated, and the obtained crude product was dissolved in a mixture of 5 ml of 4 N solution of hydrogen chloride in dioxane and 1 ml of ethanol, and the obtained solution was stirred for 3 days. The solvent was evaporated, and the obtained crude product was dissolved in 20 ml of ethanol. 500 mg of ammonium carbonate was added to the obtained solution, and they were stirred overnight. The solvent was evaporated, then the obtained crude product was dissolved in 10 ml of 6 N aqueous hydrochloric acid solution, and the obtained solution was stirred at 50° C. for 2 hours. The solvent was evaporated, and the obtained crude product was treated in the same manner as that in step 9 in Example 1 to obtain the title compound.

Yield: 70 mg (0.10 mmol) (3%)

MS (ESI,m/z) 454(MH+)

H-NMR (DMSO-d6) δ 1.65–1.96 (4H, m), 2.27–2.58 (3H, m), 2.73–3.10 (4H, m), 3.29–3.56 (4H, m), 4.09 (2H, t), 4.35 (2H, br), 7.35 (3H, br), 7.56 (2H, d), 8.25 (1H, t), 8.70 (2H, d), 9.16 (2H, br), 9.22 (2H, br)

EXAMPLE 19

Synthesis of 3-[4-amidino-2-(2-((1-(pyridine-4-carbonyl)piperidine-4-carbonyl)amino)ethoxy) phenyl]propionic acid bistrifluoroacetate Step 1: Synthesis of ethyl 1-(pyridyl-4-carbonyl)-4-piperidinecarboxylate 1.25 g (7.0 mmol) of isonicotinoyl chloride hydrochloride, 1.0 g (6.4 mmol) of ethyl piperidine-4-carboxylate and 1.3 ml (9.6 mmol) of triethylamine were stirred in 10 ml of DMF at room temperature for 4 hours. After the treatment with ethyl acetate as the extraction solvent in an ordinary manner, the obtained crude product was purified by the silica gel column chromatography to obtain the title compound.

Yield: 850 mg (2.84 mmol) (44%)

H-NMR (CDCl3) δ 1.27 (3H, t), 1.60–2.09 (4H, m), 2.02–2.17 (2H, m), 2.50–2.68 (1H, m) 3.06 (2H, d), 3.60 (1H, d), 4.18 (2H, q), 4.50 (2H, d),

Step 2: Synthesis of 3-[4-amidino-2-(2-((1-(pyridine-4-carbonyl)piperidine-4-carbonyl)amino)ethoxy)phenyl] propionic acid bistrifluoroacetate 850 mg (2.84 mmol) of ethyl 1-(pyridyl-4-carbonyl)-4-piperidinecarboxylate was stirred in 10 ml of dioxane. 10 ml of 2 N hydrochloric acid was added to the obtained mixture, and they were stirred at 95° C. for 4 hours. The solvent was evaporated, and the obtained crude product was dissolved in 10 ml of DMF. 700 mg (2.5 mmol) of ethyl 3-[2-(2-aminoethoxy)-4-cyanophenyl]propionate hydrochloride, 634 mg (3.75 mmol) of 2-chloro-1,3-dimethylimidazonium chloride and 1.74 ml (7.5 mmol) of triethylamine were added to the obtained solution, and they were stirred overnight. The solvent was evaporated, and the obtained crude product was dissolved in a mixture of 5 ml of 4 N solution of hydrogen chloride in dioxane and 1 ml of ethanol, and they were stirred for 3 days. The solvent was evaporated, and the obtained crude product was dissolved in 20 ml of ethanol. 500 mg of ammonium carbonate was added to the obtained solution, and they were stirred overnight. The solvent was evaporated, and the obtained crude product was dissolved in 10 ml of 6 N aqueous hydrochloric acid solution, and the obtained solution was stirred at 50° C. for 2 hours. The solvent was evaporated, and the obtained crude product was treated in the same manner as that in step 9 in Example 1 to obtain the title compound.

Yield: 100 mg (0.15 mmol) (5%)

MS (ESI,m/z) 454(MH+)

H-NMR (DMSO-d6) δ 1.37–1.84 (4H, m), 2.27–2.56 (3H, m), 2.73–3.13 (4H, m), 3.29–3.56 (3H, m), 4.09 (2H, t), 4.42 (1H, d), 7.21–7.33 (5H, m), 8.10 (1H, t), 8.67 (2H, d), 8.94 (2H, br), 9.21 (2H, br)

EXAMPLE 20

Synthesis of 3-[4-amidino-2-(2-((1-(3,5-dichloropyridine-4-yl)piperidine-4-carbonyl)amino) ethoxy)phenyl]propionic acid bistrifluoroacetate Step 1: Synthesis of ethyl 1-(3,5-dichloropyridine-4-yl)-4-piperidinecarboxylate 2.0 g (11 mmol) of 3,4,5-trichloropyridine, 1.7 g (11 mmol) of ethyl piperidine-4-carboxylate and 4.6 ml (33 mmol) of triethylamine were stirred in 20 ml of xylene under heating under reflux for 10 hours. After the treatment with ethyl acetate as the extraction solvent in an ordinary manner, the obtained crude product was purified by the silica gel column chromatography to obtain the title compound.

Yield: 800 mg (2.6 mmol) (24%)

H-NMR (CDCl3) δ 1.28 (3H, t), 1.80–2.03 (4H, m), 2.44–2.58 (1H, m), 3.23–3.44 (4H, m), 4.17 (2H, q), 8.32 (2H, s)

Step 2: Synthesis of ethyl 3-[4-cyano-2-(2-((1-(3,5-dichloropyridine-4-yl)piperidine-4-carbonyl)amino)ethoxy)phenyl]propionate 2.0 g (6.5 mmol) of ethyl 1-(3,5-dichloropyridine-4-yl)-4-piperidinecarboxylate was stirred in 5 ml of dioxane. 5 ml of 2 N hydrochloric acid was added to the obtained mixture, and they were stirred at 95° C. for 4 hours. The solvent was evaporated, and the obtained crude product was dissolved in 10 ml of DMF. 612 mg (2.27 mmol) of ethyl 3-[2-(2-aminoethoxy)-4-cyanophenyl]propionate hydrochloride, 575 mg (3.40 mmol) of 2-chloro-1,3-dimethylimidazonium chloride and 0.9 ml (6.8 mmol) of triethylamine were added to the obtained solution, and they were stirred overnight. After the treatment with ethyl acetate as the extraction solvent in an ordinary manner, the obtained crude product was purified by the silica gel column chromatography to obtain the title compound.

Yield: 1.0 g (1.9 mmol) (73%)

H-NMR (CDCl3) δ 1.21 (3H, t), 1.83–2.06 (4H, m), 2.31–2.43 (2H, m), 2.46–2.60 (1H, m), 2.62 (2H, t), 3.00 (2H, t), 3.22–3.41 (4H, m), 3.73 (2H, dt), 4.03–4.11 (4H, m), 7.04 (1H, br), 7.22 (2H, d), 8.32 (2H, s)

Step 3: Synthesis of 3-[4-amidino-2-(2-((1-(3,5-dichloropyridine-4-yl)piperidine-4-carbonyl)amino)ethoxy)phenyl]propionic acid bistrifluoroacetate 1.0 g (1.9 mmol) of ethyl 3-[4-cyano-2-(2-((1-(3,5-dichloropyridine-4-yl)piperidine-4-carbonyl)amino)ethoxy)phenyl]propionate was dissolved in a mixture of 10 ml of 4 N solution of hydrogen chloride in dioxane and 2 ml of ethanol, and they were stirred for 3 days. The solvent was evaporated, and the obtained crude product was dissolved in 20 ml of ethanol. 500 mg of ammonium carbonate was added to the obtained solution, and they were stirred overnight. The solvent was evaporated, and the obtained crude product was dissolved in 10 ml of 6 N aqueous hydrochloric acid solution, and the obtained solution was stirred at 50° C. for 2 hours. The solvent was evaporated, and the obtained crude product was treated in the same manner as that in step 9 in Example 1 to obtain the title compound.

Yield: 280 mg (0.38 mmol) (20%)

MS (ESI,m/z) 508 (MH+)

H-NMR (DMSO-d6) δ 1.62–1.78 (4H, m), 2.16–2.22 (1H, m), 2.52 (2H, t), 2.87 (2H, t), 3.18–3.27 (4H, m), 3.46 (2H, t), 4.12 (2H, t), 7.30–7.41 (3H, m), 8.12 (1H, t), 8.41 (2H, s), 8.98 (2H, br), 9.22 (2H, br)

EXAMPLE 21

Synthesis of 3-[4-amidino-2-(2-((4-methyl-2-pyridyl-4-ylthiazole-5-carbonyl)amino) ethoxy)phenyl]propionic acid bistrifluoroacetate Step 1: Synthesis of ethyl 4-methyl-2-(4-pyridyl)thiazole-5-carboxylate 2.76 g (20 mmol) of thioisonicotinamide and 3.6 g (22 mmol) of ethyl 2-chloroacetacetate were heated under reflux in 30 ml of ethanol for 20 hours. After the treatment with ethyl acetate as the extraction solvent in an ordinary manner, the obtained crude product was purified by the silica gel column chromatography to obtain the title compound.

Yield: 2.0 g (8.1 mmol) (40%)

H-NMR (CDCl3) δ 1.40 (3H, t), 2.81 (3H, s), 4.38 (2H, q), 7.81 (2H, d), 8.73 (2H, d)

Step 2: Synthesis of ethyl 3-[4-cyano-2-(2-((4-methyl-2-pyridyl-4-yl-thiazole-5-carbonyl)amino)ethoxy)phenyl]propionate 1.58 g (6.37 mmol) of ethyl 4-methyl-2-(4-pyridyl)thiazole-5-carboxylate was stirred in 5 ml of ethanol. 5 ml of 1 N sodium hydroxide was added to the obtained mixture, and they were stirred at room temperature for 4 hours. 5 ml of 1 N hydrochloric acid was added to the reaction mixture. A portion (700 mg) of the obtained crystals was dissolved in 10 ml of DMF. 590 mg (2.12 mmol) of ethyl 3-[2-(2-aminoethoxy)-4-cyanophenyl]propionate hydrochloride, 539 mg (3.19 mmol) of 2-chloro-1,3-dimethylimidazonium chloride and 1.3 ml (9.57 mmol) of triethylamine were added to the obtained solution, and they were stirred overnight. After the treatment with ethyl acetate as the extraction solvent in an ordinary manner, the obtained crude product was purified by the silica gel column chromatography to obtain the title compound.

Yield: 600 mg (1.29 mmol)

H-NMR (CDCl3) δ 1.15 (3H, t), 2.61 (2H, t), 3.01 (2H, t), 3.92 (2H, dt), 4.03 (2H, q), 4.20 (2H, t), 7.07 (1H, br), 7.25 (2H, d), 7.80 (2H, d), 8.73 (2H, d)

Step 3: Synthesis of 3-[4-amidino-2-(2-((4-methyl-2-pyridyl-4-ylthiazole-5-carbonyl)amino)ethoxy)phenyl]propionic acid bistrifluoroacetate 600 mg (1.29 mmol) of ethyl 3-[4-cyano-2-(2-((4-methyl-2-pyridyl-4-yl-thiazole-5-carbonyl) amino)ethoxy)phenyl]propionate was dissolved in a mixture of 10 ml of 4 N hydrogen chloride in dioxane and 2 ml of ethanol, and they were stirred for 3 days. The solvent was evaporated, and the obtained crude product was dissolved in 20 ml of ethanol. 500 mg of ammonium carbonate was added to the obtained solution, and they were stirred overnight. The solvent was evaporated, and the obtained crude product was dissolved in 10 ml of 6 N aqueous hydrochloric acid solution, and the obtained solution was stirred at 50° C. for 2 hours. The solvent was evaporated, and the obtained crude product was treated in the same manner as that in step 9 in Example 1 to obtain the title compound.

Yield: 300 mg (0.44 mmol) (34%)

MS (ESI,m/z) 454(MH+)

H-NMR (DMSO-d6) δ 2.53 (2H, t), 2.63 (3H, s), 2.88 (2H, t), 3.68 (2H, dt), 4.23 (2H, t), 7.32–7.41 (3H, m), 7.88 (2H, d), 8.66 (1H, t), 8.73 (2H, d), 9.05 (2H, br), 9.23 (2H, br)

EXAMPLE 22

Synthesis of 3-[4-amidino-2-(2-((1-(6-chloropyridazine-3-yl)piperidine-4-carbonyl)amino) ethoxy)phenyl]propionic acid bistrifluoroacetate Step 1: Synthesis of ethyl 1-(6-chloropyridazine-3-yl)-4-piperidinecarboxylate 2.0 g (13.4 mmol) of 3,6-dichloropyridazine, 2.3 g (14.8 mmol) of ethyl piperidine-4-carboxylate and 4.6 ml (33 mmol) of triethylamine were stirred in 20 ml of DMF at 50° C. for 4 hours. After the treatment with ethyl acetate as the extraction solvent in an ordinary manner, the obtained crude product was purified by the silica gel column chromatography to obtain the title compound.

Yield: 1.58 g (5.86 mmol) (44%)

H-NMR (CDCl3) δ 1.26 (3H, t), 1.71–1.88 (2H, m), 1.97–2.06 (2H, m), 2.50–2.64 (1H, m), 3.03–3.17 (2H, m), 4.16 (2H, q), 4.23 (2H, dt), 6.91 (1H, d), 7.18 (1H, d)

Step 2: Synthesis of 3-[4-amidino-2-(2-((1-(6-chloropyridazine-3-yl)piperidine-4-carbonyl)amino)ethoxy)phenyl]propionic acid bistrifluoroacetate 600 mg (2.22 mmol) of ethyl 1-(6-chloropyridazine-3-yl)-4-piperidinecarboxylate was stirred in 5 ml of dioxane. 5 ml of 2 N hydrochloric acid was added to the obtained mixture, and they were stirred at 95° C. for 4 hours. The solvent was evaporated, and the obtained crude product was dissolved in 10 ml of DMF. 514 mg (1.85 mmol) of ethyl 3-[2-(2-aminoethoxy)-4-cyanophenyl]propionate hydrochloride, 470 mg (2.78 mmol) of 2-chloro-1,3-dimethylimidazonium chloride and 0.77 ml (5.58 mmol) of triethylamine were added to the obtained solution, and they were stirred overnight. After the treatment with ethyl acetate as the extraction solvent in an ordinary manner, the obtained crude product was dissolved in a mixture of 10 ml of 4 N solution of hydrogen chloride in dioxane and 2 ml of ethanol, and they were stirred for 3 days. The solvent was evaporated, and the obtained crude product was dissolved in 20 ml of ethanol. 500 mg of ammonium carbonate was added to the obtained solution, and they were stirred overnight. The solvent was evaporated, then the obtained crude product was dissolved in 10 ml of 6 N aqueous hydrochloric acid solution, and the obtained solution was stirred at 50° C. for 2 hours. The solvent was evaporated, and the obtained crude product was treated in the same manner as that in step 9 in Example 1 to obtain the title compound.

Yield: 280 mg (0.40 mmol) (18%)

MS (ESI,m/z) 475 (MH+)

H-NMR (DMSO-d6) δ 1.43–1.62 (2H, m), 1.70–1.82 (2H, m), 2.37–2.60 (3H, m), 2.77–3.01 (4H, m), 3.47 (2H, dt), 4.27 (2H, t), 4.32 (2H, d), 7.23–7.42 (4H, m), 7.49 (1H, d), 8.14 (1H, t), 8.99 (2H, br), 9.24 (2H, br)

EXAMPLE 23

Synthesis of 3-[4-amidino-2-(2-((1-pyridazine-3-yl)piperidine-4-carboxyl)amino)ethoxy)phenyl] propionamide bistrifluoroacetate 150 mg (0.21 mmol) of 3-[4-amidino-2-(2-((1-(6-chloropyridazine-3-yl)piperizine-4-carbonyl)amino)ethoxy)phenyl]propionic acid bistrifluoroacetate was dissolved in 10 ml of ethanol. 10 mg of Pd-C was added to the obtained solution, and they were stirred in the presence of hydrogen at room temperature for 4 hours. The reaction solution was filtered through Celite, and the obtained crude product was treated in the same manner as that in step 9 in Example 1 to obtain the title compound.

Yield: 50 mg (0.075 mmol) (36%)

MS (ESI,m/z) 441 (MH+)

H-NMR (DMSO-d6) δ 1.50–1.63 (2H, m), 1.77–1.91 (2H, m), 2.51 (2H, t), 2.84 (2H, t), 3.00–3.19 (2H, m), 3.39–3.58 (1H, m), 3.46 (2H, dt), 4.08 (2H, t), 4.27 (2H, d), 7.32 (1H, d), 7.34 (1H, d), 7.75 (1H, br), 8.15 (1H, t), 8.61 (1H, d), 9.05 (2H, br), 9.22 (2H, br)

EXAMPLE 24

Synthesis of 3-[4-amidino-2-(2-((1-(2-chloropyrimidine-4-yl)piperidine-4-carbonyl)amino)ethoxy)phenyl]propionic acid bistrifluoroacetate Step 1: Synthesis of ethyl 1-(2-chloropyrimidine-4-yl)-4-piperidinecarboxylate 2.0 g (13.4 mmol) of 2,4-dichloropyrimidine, 2.32 g (14.7 mmol) of ethyl piperidine-4-carboxylate and 4.6 ml (33 mmol) of triethylamine were stirred in 20 ml of DMF at 50° C. for 4 hours. After the treatment with ethyl acetate as the extraction solvent in an ordinary manner, the obtained crude product was purified by the silica gel column chromatography to obtain the title compound.

Yield: 700 mg (2.60 mmol) (19%)

H-NMR (CDCl3) δ 1.26 (3H, t), 1.63–1.80 (2H, m), 1.92–2.09 (2H, m), 2.52–2.66 (1H, m), 3.03–3.19 (2H, m), 4.11–4.37 (4H, m), 6.39 (1H, d), 8.02 (1H, d)

Step 2: Synthesis of ethyl 3-[4-cyano-2-(2-((1-(2-chloropyrimidine-4-yl)piperidine-4-carbonyl) amino) ethoxy)phenyl]propionate 700 mg (2.60 mmol) of ethyl 1-(2-chloropyridine-4-yl)-4-piperidinecarboxylate was stirred in 5 ml of dioxane. 5 ml of 2 N hydrochloric acid was added to the obtained mixture, and they were stirred at 95° C. for 4 hours. The solvent was evaporated, and the obtained crude product was dissolved in 10 ml of DMF. 600 mg (2.16 mmol) of ethyl 3-[2-(2-aminoethoxy)-4-cyanophenyl]propionate hydrochloride, 548 mg (3.24 mmol) of 2-chloro-1,3-dimethylimidazonium chloride and 0.9 ml (6.48 mmol) of triethylamine were added to the obtained solution, and they were stirred overnight. After the treatment with ethyl acetate as the extraction solvent in an ordinary manner, the obtained crude product was purified by the silica gel column chromatography to obtain the title compound.

Yield: 320 mg (0.66 mmol) (31%)

H-NMR (CDCl3) δ 1.25 (3H, t), 1.63–2.05 (4H, m), 2.60 (2H, t), 2.99 (2H, t), 3.00–3.21 (3H, m), 3.68 (2H, dt), 4.07 (2H, t), 4.15 (2H, q), 4.18–4.41 (2H, m), 6.38 (1H, d), 7.02 (1H, bs), 7.23 (1H, bs), 8.00 (2H, br)

Step 3: Synthesis of 3-[4-amidino-2-(2-((1-(2-chloropyrimidine-4-yl)piperidine-4-carbonyl)amino) ethoxy]phenyl]propionic acid bistrifluoroacetate 320 mg (0.66 mmol) of ethyl 3-[4-cyano-2-(2-((1-(2-chloropyrimidine-4-yl)piperidine-4-carbonyl)amino) ethoxy)phenyl]propionate was dissolved in a mixture of 10 ml of 4 N solution of hydrogen chloride in dioxane and 2 ml of ethanol, and they were stirred for 3 days. The solvent was evaporated, and the obtained crude product was dissolved in 20 ml of ethanol. 500 mg of ammonium carbonate was added to the obtained solution, and they were stirred overnight. The solvent was evaporated, and the obtained crude product was dissolved in 10 ml of 6 N aqueous hydrochloric acid solution, and the obtained solution was stirred at 50° C. for 2 hours. The solvent was evaporated, and the obtained crude product was treated in the same manner as that in step 9 in Example 1 to obtain the title compound.

Yield: 50 mg (0.071 mmol) (11%)

MS (ESI,m/z) 475 (MH+)

H-NMR (DMSO-d6) δ 1.37–1.58 (2H, m), 1.63–2.01 (2H, m), 2.54 (2H, t), 2.86 (2H, t), 2.94–3.24 (3H, m), 3.46 (2H, dt), 4.08 (2H, t), 4.20 (2H, br), 6.81 (1H, d), 7.32 (1H, d), 7.34 (2H, d), 8.03 (1H, d), 8.13 (1H, t), 8.98 (2H, br), 9.21 (2H, br)

EXAMPLE 25

Synthesis of 3-[4-amidino-2-(2-((1-(pyrimidine-4-yl)piperidine-4-carbonyl)amino)ethoxy)phenyl] propionic acid bistrifluoroacetate 50 mg (0.071 mmol) of 3-[4-amidino-2-(2-((1-(2-chloropyrimidine-4yl)piperizine-4-carbonyl)amino)ethoxy) phenyl]propionic acid bistrifluoroacetate was dissolved in 5 ml of ethanol. 10 mg of palladium/carbon was added to the obtained solution, and they were stirred in the presence of hydrogen at room temperature for 4 hours. The reaction solution was filtered through Celite, the solvent was evaporated and the obtained crude product was treated in the same manner as that in step 9 in Example 1 to obtain the title compound.

Yield: 18 mg (0.027 mmol) (38%)

MS (ESI,m/z) 441 (MH+)

H-NMR (DMSO-d6) δ 1.42–1.61 (2H, m), 1.70–1.91 (2H, m), 2.54 (2H, t), 2.85 (2H, t), 3.03–3.24 (3H, m), 3.46 (2H, dt), 4.08 (2H, t), 4.46 (2H, br), 7.17 (1H, dd), 7.34 (2H, d), 7.38 (1H, dd), 8.18 (3H, br), 9.18 (2H, br), 9.22 (2H, br)

EXAMPLE 26

Synthesis of 3-[4-amidino-(2R)-2-((1-(pyridine-4-yl)piperidine-4-carbonyl)pyrrolidine-2-ylmethoxy) phenyl]propionic acid bistrifluoroacetate Step 1: Synthesis of 1-t-butoxycarbonyl-(2R)-2-(p-tolylmethanesulfonyloxymethyl)pyrrolidine 1 g of D-prolinol was dissolved in 24 ml of dioxane. 2.4 g (10.5 mmol) of di-t-butyl carbonate and 5.3 ml of 2 M aqueous sodium hydroxide solution were added to the obtained solution under cooling with ice. They were stirred for 15 minutes and then at room temperature for additional 2 hours. The solvent was evaporated, and the residue was treated with ethyl acetate as the extraction solvent in an ordinary manner to obtain the crude product. The crude product was dissolved in 15 ml of dichloromethane. 2.23 g (10.8 mmol) of tosyl chloride and 1.5 ml (10.5 mmol) of triethylamine were added to the obtained solution, and they were stirred at room temperature overnight. After the treatment in an ordinary manner, the obtained crude product was purified by the silica gel column chromatography to obtain the title compound.

Yield: 2.55 g (7.17 mmol), (72%)

H-NMR (CDCl3) δ 1.38 (9H,br), 1.70–2.00 (4H,m), 2.45 (3H,s), 3.30 (2H,br), 3.90 (1H, br), 4.10 (2H,br), 7.32 (2H,d), 7.78 (2H,d).

Step 2: Synthesis of 4-iodo-3-[(2R)-(1-t-butoxycarbonyl-pyrrolidine-2-ylmethoxy)]benzonitrile 2.0 g (8.16 mmol) of 3-hydroxy-4-iodobenzonitrile was dissolved in 20 ml of DMF. 5.8 g (16.3 mmol) of 1-t-butoxycarbonyl-(2R)-2-(p-tolylmethanesulfonyloxymethyl)pyrrolidine and 3.37 g (24.4 mmol) of potassium carbonate were added to the obtained solution, and they were stirred at 50° C. for 16 hours. 1.5 g (4.2 mmol) of 1-t-butoxycarbonyl-(2R)-2-(p-tolylmethanesulfonyloxymethyl)pyrrolidine was added to the obtained mixture, and they were stirred at 50° C. for 4 hours. After the treatment with ethyl acetate as the extraction solvent in an ordinary manner, the obtained crude product was purified by the silica gel column chromatography to obtain the title compound.

Yield: 3.7 g (8.6 mmol)

H-NMR (CDCl3) δ 1.47 (9H, s), 1.78–2.19 (4H, m), 3.22–3.34 (2H, m), 3.83–4.04 (1H, m), 4.06–4.23 (2H, m), 3.03–3.41 (2H, m), 6.96 (1H, br), 7.08 (1H, br), 7.88 (1H, br)

Step 3: Synthesis of ethyl 3-[4-cyano-(2R)-2-(1-t-butoxycarbonylpyrrolidine-2-ylmethoxy)phenyl]acrylate 3.7 g (8.6 mmol) of 4-iodo-3-[(2R)-(1-t-butoxycarbonyl-pyrrolidine-2-ylmethoxy)]benzonitrile was dissolved in 40 ml of DMF. 4.68 ml (43 mmol) of ethyl acrylate , 6.1 ml (43 mmol) of triethylamine and 194 mg (0.85 mmol) of palladium acetate were added to the obtained solution, and they were stirred at 100° C. overnight. After the treatment with ethyl acetate as the extraction solvent in an ordinary manner, the obtained crude product was treated with ethyl acetate as the extraction solvent in an ordinary manner to obtain the crude product, which was purified by the silica gel column chromatography to obtain the title compound.

Yield: 3.0 g (7.5 mmol) (87%)

H-NMR (CDCl3) δ 1.34 (3H, t), 1.46 (9H, s), 1.90–2.17 (4H, m), 3.31–3.55 (2H, m), 4.02–4.39 (3H, m), 4.27 (2H, q), 6.53 (1H, d), 7.13–7.28 (2H, m), 7.46–7.62 (1H, m), 7.93 (1H, d)

Step 4: Synthesis of ethyl 3-[4-cyano-(2R)-2-(pyrrolidine-2-ylmethoxy)phenyl]propionate 3.0 g (7.5 mmol) of ethyl 3-[4-cyano-(2R)-2-(1-t-butoxycarbonyl-pyrrolidine-2-ylmethoxy)phenyl]acrylate was dissolved in 20 ml of ethanol. 600 mg of 10% palladium/carbon (50% aqueous) was added to the obtained solution, and they were stirred in the presence of hydrogen overnight. The reaction solution was filtered through Celite, and the solvent was evaporated. The obtained crude product was dissolved in 10 ml of 4 N solution of hydrogen chloride in dioxane, and the obtained solution was stirred at room temperature for 3 hours. The solvent was evaporated to obtain hydrochloride of the title compound.

Yield: 1.8 g (6.0 mmol) (79%)

Step 5: Synthesis of ethyl 3-[4-cyano-(2R)-2-((1-(pyridine-4-yl)piperidine-4-carbonyl)pyrrolidine-2-ylmethoxy) phenyl]propionate 570 mg (1.89 mmol) of ethyl 3-[4-cyano-(2R)-2-(pyrrolidine-2-ylmethoxy)phenyl]propionate was dissolved in 10 ml of DMF. 504 mg (2.1 mmol) of 1-(4-pyridyl)-4-piperidinecarboxylic acid hydrochloride, 479 mg (2.8 mmol) of 2-chloro-1,3-dimethylimidazonium chloride and 0.78 ml (5.7 mmol) of triethylamine were added to the obtained solution, and they were stirred overnight.

Yield: 600 mg (1.22 mmol) (65%)

H-NMR (DMSO-d6) δ 1.24 (3H, t), 1.48–1.75 (2H, m), 1.78–1.94 (2H, m), 1.95–2.20 (4H, m), 2.52–2.64 (3H, m), 2.80–3.03 (3H, m), 3.50–3.66 (2H, m), 3.82–4.00 (2H, m), 4.03–4.22 (4H, m), 4.40–4.52 (2H, m), 6.66 (2H, d), 7.11 (1H, br), 7.18–7.25 (2H, m), 8.24 (2H, d)

Step 6: Synthesis of 3-[4-amidino-(2R)-2-((1-(pyridine-4-yl)piperidine-4-carbonyl)pyrrolidine-2-ylmethoxy)phenyl] propionic acid bistrifluoroacetate 600 g (1.22 mmol) of ethyl 3-[4-cyano-(2R)-2-((1-(pyridine-4-yl)piperidine-4-carbonyl)pyrrolidine-2-ylmethoxy)phenyl]propionate was dissolved in a mixture of 5 ml of 4 N solution of hydrogen chloride in dioxane and 1 ml of ethanol, and they were stirred for 3 days. The solvent was evaporated, and the obtained crude product was dissolved in 20 ml of ethanol. 500 mg of ammonium carbonate was added to the obtained solution, and they were stirred overnight. The solvent was evaporated, and the obtained crude product was dissolved in 10 ml of 6 N aqueous hydrochloric acid solution. The obtained solution was stirred at 50° C. for 2 hours. The solvent was evaporated, and the obtained crude product was treated in the same manner as that in step 9 in Example 1 to obtain the title compound.

Yield: 190 mg (0.27 mmol) (22%)

MS (ESI,m/z) 480 (MH+)

H-NMR (DMSO-d6) δ 1.28–1.60 (2H, m), 1.77–2.16 (6H, m), 2.50 (2H, t), 2.77–3.00 (3H, m), 3.16–3.30 (2H, m), 3.52–3.78 (2H, m), 4.06–4.29 (5H, m), 7.17 (2H, d), 7.34 (2H, d), 7.36 (1H, d), 8.19 (2H, t), 9.18 (2H, br), 9.21 (2H, br)

EXAMPLE 27

Synthesis of 3-[4-amidino-(2R)-2-((1-(2-naphthalenesulfonyl)pyrrolidine-2-ylmethoxy) phenyl]propionic acid mono-trifluoroacetate 240 mg (0.79 mmol) of ethyl 3-[4-cyano-(2R)-2-(pyrrolidine-2-ylmethoxy)phenyl]propionate hydrochloride was dissolved in 10 ml of DMF. 271 mg (1.2 mmol) of 2-naphthalenesulfonyl chloride and 0.22 ml (1.58 mmol) of triethylamine were added to the obtained solution, and they were stirred overnight. The solvent was evaporated, and the obtained crude product was dissolved in a mixture of 5 ml of 4 N solution of hydrogen chloride in dioxane and 1 ml of ethanol, and the obtained solution was stirred for 3 days. the solvent was evaporated, and the obtained crude product was dissolved in 20 ml of ethanol. 200 mg of ammonium carbonate was added to the obtained solution, and they were stirred overnight. The solvent was evaporated, and the obtained crude product was dissolved in 10 ml of 6 N aqueous hydrochloric acid solution. The obtained solution was stirred at 50° C. for 2 hours. The solvent was evaporated, and the obtained crude product was treated in the same manner as that in step 9 in Example 1 to obtain the title compound.

Yield: 8 mg (0.013 mmol) (2%)

MS (ESI,m/z) 482 (MH+)

H-NMR (DMSO-d6) δ 1.41–1.77 (2H, m), 1.81–1.94 (2H, m), 2.50 (2H, t), 2.80 (2H, t), 3.17–3.44 (3H, m), 4.03–4.36 (2H, m), 7.34 (1H, s), 7.36 (2H, d), 7.69 (2H, dd), 7.88 (1H, d), 8.12 (2H, dd), 8.52 (1H, s), 8.96 (2H, br), 9.26 (2H, br)

EXAMPLE 28

Synthesis of (3R)-4-(5-amidino-2-hydroxyphenoxy)-3-[4-(1-acetimidoyl-4-piperidyloxy)benzoylamino]butanoic acid bistrifluoroacetate Step 1: Synthesis of benzyl (3R)-3-t-butoxycarbonylamino-4-(5-cyano-2-benzyloxyphenoxy)butanoate 4.8 g (15.5 mmol) of benzyl (3R)-3-t-butoxycarbonylamino-4-hydroxybutanoate was dissolved in 100 ml of tetrahydrofuran. 2.9 g (12.9 mmol) of 4-benzyloxy-3-hydroxybenzonitrile, 4.1 g (15.5 mmol) of triphenylphosphine and 6.7 g (15.5 mmol) of diethyl azodicarboxylate were added to the obtained solution under cooling with ice, and they were stirred at room temperature overnight. After the treatment with ethyl acetate as the extraction solvent in an ordinary manner, the obtained crude product was purified by the silica gel column chromatography to obtain the title compound.

Yield: 3.7 g (7.2 mmol) (56%)

H-NMR (CDCl3) δ 1.43 (9H, s), 2.64–2.83 (2H, m), 3.98–4.42 (3H, m), 5.12 (2H, d), 5.14 (2H, s), 6.97 (1H, d), 7.18 (1H, s), 7.28–7.40 (6H, m)

Step 2: Synthesis of (3R)-4-(5-amidino-2-hydroxyphenoxy)-3-[4-(1-acetimidoyl-4-piperidyloxy)benzoylamino]butanoic acid bistrifluoroacetate 2.0 g (3.88 mmol) of benzyl (3R)-3-t-butoxycarbonylamino-4-(5-cyano-2-benzyloxyphenoxy)butanoate was dissolved in 20 ml of 4 N solution of hydrogen chloride in dioxane, and the obtained solution was stirred at room temperature for 4 hours. The solvent was evaporated and the obtained crude product was dissolved in 20 ml of DMF. 1.36 g (4.26 mmol) of 4-(1-t-butoxycarbonyl-4-piperidyloxy)benzoic acid, 980 mg (5.82 mmol) of 2-chloro-1,3-dimethylimidazonium chloride and 1.6 ml (11.6 mmol) of triethylamine were added to the obtained solution, and they were stirred for 16 hours. After the treatment with ethyl acetate as the extraction solvent in an ordinary manner, the obtained crude product was dissolved in a mixture of 20 ml of 4 N solution of hydrogen chloride in dioxane and 5 ml of ethanol, and they were stirred for 3 days. The solvent was evaporated, and the obtained crude product was dissolved in 10 ml of ethanol. 500 mg of ammonium carbonate was added to the obtained solution, and they were stirred overnight. The solvent was evaporated, and the residue was dissolved in 20 ml of ethanol. 2.0 g of ethyl acetimidate and 2 ml of triethylamine were added to the obtained solution, and they were stirred at room temperature overnight. The solvent was evaporated, and the obtained crude product was dissolved in 10 ml of ethanol. 50 mg of 10% palladium/carbon was added to the obtained solution, and they were stirred in the presence of hydrogen overnight. The reaction liquid was filtered through Celite, and the solvent was evaporated. The obtained crude product was dissolved in 10 ml of 6 N aqueous hydrogen chloride solution, and the obtained solution was stirred at 6° C. for 2 hours. The solvent was evaporated, and the obtained crude product was treated in the same manner as that in step 9 in Example 1 to obtain the title compound.

Yield: 7.6 g (0.01 mmol) (0.3%)

MS (ESI,m/z) 498 (MH+)

H-NMR (DMSO) δ 1.62–1.85 (2H, m), 1.99–2.16 (2H, m), 2.27 (3H, s), 2.62–2.88 (2H, m), 3.40–3.58 (2H, m), 3.63–3.81 (2H, m), 3.94–4.05 (1H, m), 4.60–4.82 (2H, m), 6.96 (1H, d), 7.06 (2H, d), 7.17–7.24 (1H, m), 7.28–7.42 (1H, m), 7.79 (2H, d), 8.33 (1H, d), 8.60 (1H, br), 8.86 (2H, br), 9.01 (2H, br), 9.14 (1H, br)

EXAMPLE 29

Synthesis of (3R)-4-(5-amidino-2-hydroxyphenoxy)-3-[(1-(pyridine-4-yl)piperidine-4-carbonyl)amino]butanoic acid bistrifluoroacetate Step 1: Synthesis of benzyl (3R)-4-(5-cyano-2-benzyloxyphenoxy)-3-[(1-(pyridine-4-yl)piperidine-4-carbonyl)amino]butanoate 2.1 g (4.07 mmol) of benzyl (3R)-3-t-butoxycarbonylamino-4-(5-cyano-2-benzyloxyphenoxy)butanoate was dissolved in 20 ml of 4 N solution of hydrogen chloride in dioxane, and they were stirred at room temperature for 4 hours. The solvent was evaporated and the obtained crude product was dissolved in 20 ml of DMF. 1.08 g (1.03 mmol) of 1-(4-pyridyl)-4-piperidinecarboxylate hydrochloride, 1.03 g (6.11 mmol) of 2-chloro-1,3-dimethylimidazonium chloride and 1.7 ml (61.6 mmol) of triethylamine were added to the obtained solution, and they were stirred for 16 hours. After the treatment with ethyl acetate as the extraction solvent in an ordinary manner, the obtained crude product was purified by the silica gel column chromatography. 1.0 g (1.66 mmol) (of 2.0 g in total) of the obtained product was dissolved in a mixture of 20 ml of 4 N solution of hydrogen chloride in dioxane and 4 ml of ethanol, and the obtained solution was stirred at room temperature for 3 days. The solvent was evaporated under reduced pressure, and the obtained crude product was dissolved in 20 ml of ethanol. 1.0 g of ammonium carbonate was added to the obtained solution, and they were stirred at room temperature overnight. The solvent was evaporated, and the obtained crude product was dissolved in 10 ml of ethanol. 100 mg of 10% palladium/carbon was added to the obtained solution, and they were stirred in the presence of hydrogen overnight. The reaction liquid was filtered through Celite, and the solvent was evaporated. The obtained crude product was dissolved in 28 ml of 6 N aqueous hydrogen chloride solution, and the obtained solution was stirred at 60° C. for 2 hours. The solvent was evaporated, and the obtained crude product was treated in the same manner as that in step 9 in Example 1 to obtain the title compound.

Yield: 350 mg (0.52 mmol) (26%)

MS (ESI, m/z) 442 (MH+)

H-NMR (DMSO) δ 1.42–1.64 (2H, m), 1.76–1.84 (2H, m), 2.44–2.81 (3H, m), 3.17–3.28 (2H, m), 3.82–3.98 (1H, m), 4.02–4.22 (3H, m), 4.37–4.59 (1H, m), 6.98 (1H, d), 7.19 (2H, d), 7.38 (2H, d), 8.07 (1H, d), 8.22 (2H, d), 8.87 (2H, br), 9.03 (2H, br)

EXAMPLE 30

Synthesis of ethyl 3-[4-N-hydroxyamidino-2-(2-((1-(pyridine-4-yl)piperidine-4-carbonyl)amino)ethoxy)phenyl]propionate bistrifluoroacetate 225 mg (0.50 mmol) of ethyl 3-[4-cyano-2-(2-((1-(pyridine-4-yl)piperidine-4-carbonyl)amino)ethoxy)phenyl]propionate was dissolved in 2.5 ml of ethanol. 0.10 ml (0.75 mmol) of triethylamine and 52 mg (0.52 mmol) of hydroxylamine hydrochloride were added to the obtained solution, and they were stirred at 80° C. for 5 hours and then at room temperature for 16 hours. The solvent was evaporated, and the obtained crude product was treated in the same manner as that in step 9 in Example 1 to obtain the title compound.

Yield: 170 mg (0.24 mmol) (50%)

MS (ESI, m/z) 484(MH+)

H-NMR (DMSO) δ 1.13 (2H, m), 1.44–1.66 (2H, m), 1.72–1.91 (2H, m), 2.48–2.56 (1H, m), 2.57 (2H, t), 2.85 (2H, t), 3.06–3.30 (2H, m), 3.45 (2H, dt), 4.01 (2H, q), 4.05 (2H, t), 4.11–4.25 (2H, m), 7.16 (2H, d), 7.18 (2H, br), 7.32 (1H, d), 8.18 (1H, d), 8.19 (2H, d)

EXAMPLE 31

Synthesis of ethyl (2S)-3-[4-amidino-2-[4-ethoxycarbonyl-2-[(1-(1-pyridine-4-yl)piperidine-4-carbonyl)amino]butoxy]phenyl]acrylate bistrifluoroacetate Step 1: Synthesis of benzyl (4S)-4-t-butoxycarbonylamino-5-hydroxypentanoate 15 g (44.5 mmol) of γ-benzyl N-t-butoxycarbonyl-D-glutamate and 6.2 ml (44.5 mmol) of triethylamine were dissolved in 200 ml of tetrahydrofuran. 4.26 ml (44.5 mmol) of ethyl chloroformate was added to the obtained solution under cooling with ice, and they were stirred for 20 minutes. The precipitates thus formed were removed by the suction filtration. 5 g of ice and 1.69 g (44.5 mmol) of sodium borohydride were added to the filtrate under cooling with ice, and they were stirred for 2 hours. 100 ml of 1 N aqueous hydrochloric acid solution was added to the reaction mixture, and they were stirred at room temperature for one hour. After the treatment with ethyl acetate as the extraction solvent in an ordinary manner, the obtained crude product was purified by the silica gel column chromatography to obtain the title compound.

Yield: 9.2 g (28.5 mmol) (64%)

H-NMR (CDCl3) δ 1.44 (9H,s), 1.70–2.00 (2H,m), 2.28–2.58 (2H,m), 3.50–3.72 (2H,m), 4.80 (1H, br), 5.13 (2H,s), 7.35 (5H,s).

Step 2: Synthesis of benzyl (4S)-4-t-butoxycarbonylamino-5-(5-cyano-2-iodophenoxy)pentanoate 7.5 g (23.2 mmol) of benzyl (4S)-4-t-butoxycarbonylamino-5-hydroxypentanoate, 8.53 g (34.8 mmol) of iodocyanophenol and 9.13 g (34.8 mmol) of triphenylphosphine were dissolved in 120 ml of toluene. 5.99 g (34.8 mmol)) of diamide diazene dicarboxylic acid bis(N,N-dimethylamide) was added to the obtained solution under cooling with ice, and they were stirred at room temperature. The solvent was evaporated. After the treatment with ethyl acetate as the extraction solvent in an ordinary manner, the obtained crude product was purified by the silica gel column chromatography to obtain the title compound.

Yield: 3.44 g (6.25 mmol) (27%)

H-NMR (CDCl3) δ 1.44 (9H,s), 2.00–2.20 (2H,m), 2.58 (2H,t), 4.05 (2H,br), 4.85 (1H, br), 5.13 (2H,s), 6.90–7.10 (2H,m), 7.36 (5H,s), 7.87 (1H,d).

Step 3: Synthesis of ethyl 3-[(2S)-2-(2-t-butoxycarbonylamino-4-benzoxycarbonyl-butoxy)-4-cyanophenyl]acrylate 1.64 g (2.98 mmol) of benzyl (4S)-4-t-butoxycarbonylamino-5-(5-cyano-2-iodophenoxy)pentanoate was dissolved in 30 ml of N,N-dimethylformamide (dehydrated). 0.65 ml (5.96 mmol) of ethyl acrylate, 2.1 ml (14.9 mmol) of triethylamine and 14 mg (0.06 mmol) of palladium acetate were added to the obtained solution, and they were stirred at 100° C. overnight. After the treatment with ethyl acetate as the extraction solvent in an ordinary manner, the obtained crude product was purified by the silica gel column chromatography to obtain the title compound.

Yield: 1.42 g (2.71 mmol) (91%)

H-NMR (CDCl3) δ 1.31(3H,t), 1.43 (9H,s), 2.04 (2H,br), 2.54 (2H,t), 4.07 (2H, br), 4.26 (2H,q), 5.13 (2H,s), 6.50 (1H,d), 7.18 (1H,s), 7.27(1H,br), 7.35(5H,s), 7.57(1H,d), 7.97(1H,d).

Step 4: Synthesis of ethyl (2S)-3-[4-amidino-2-[4-ethoxycarbonyl-2-[(1-(1-pyridine-4-yl)piperidine-4-carbonyl)amino]butoxy]phenyl]acrylate bistrifluoroacetate 1.42 g (2.71 mmol) of ethyl 3-[(2S)-2-(2-t-butoxycarbonylamino-4-benzoxycarbonyl-butoxy)-4-cyanophenyl]acrylate was dissolved in a mixture of 15 ml of dioxane and 15 ml of 4 N solution of hydrogen chloride in dioxane, and the obtained solution was stirred at room temperature for 3 hours. The solvent was evaporated under reduced pressure, and the obtained crude product was dissolved in 10 ml of N,N-dimethylformamide. 0.72 g (2.98 mmol) of 1-(4-pyridyl)piperidine-4-carboxylic acid hydrochloride and 0.55 g (3.25 mmol) of 2-chloro-1,3-dimethylimidazolinium chloride were added to the obtained solution and then 2.3 ml (16.3 mmol) of triethylamine was added to the obtained mixture under cooling with ice, and they were stirred at room temperature overnight. The solvent was evaporated, and the residue was dissolved in a mixture of 35 ml of 4 N solution of hydrogen chloride in dioxane and 3.5 ml of ethanol, and they were stirred at room temperature for 3 days. The solvent was evaporated, and the residue was dissolved in 50 ml of ethanol. 1.6 g (28.7 mmol) of ammonium carbonate was added to the obtained solution, and they were stirred at room temperature overnight. The solvent was evaporated, and the obtained crude product was treated in the same manner as that in step 9 in Example 1 to obtain the title compound.

Yield: 387.6 mg (0.488 mmol) (36%)

MS (ESI, m/z) 566 (MH+)

H-NMR (DMSO-d6) δ 1.17 (3H,t), 1.23 (3H,t), 1.50–2.00 (4H,m), 2.30–2.65 (4H,m), 3.22 (2H,br), 4.00–4.30 (8H, m), 6.78 (1H,d), 7.18 (2H,d), 7.44 (1H, d), 7,52 (1H, s), 7.86 (1H, d), 7.98 (1H, d), 8.22 (2H, d), 9.13 (1H,br), 9.32 (1H,br), 9.35(1H,br).

EXAMPLE 32

Synthesis of (2S)-3-[4-amidino-2-[4-carbonyl-2-[(1-(1-pyridine-4-yl)piperidine-4-carbonyl)amino]butoxy]phenyl]acrylic acid bistrifluoroacetate 2.5 g of crude ethyl (2S)-3-[4-amidino-2-[4-ethoxycarbonyl-2-[(1-(1-pyridine-4-yl)piperidine-4-carbonyl)amino]butoxy]phenyl]acrylate bistrifluoroacetate was dissolved in 25 ml of 6 N aqueous hydrochloric acid solution, and the obtained solution was stirred at 80° C. for 3 hours. The solvent was evaporated, and the obtained crude product was treated in the same manner as that in step 9 in Example 1 to obtain the title compound.

Yield: 131.54 mg (0.18 mmol) (14%)

MS (ESI, m/z) 510(MH+)

H-NMR (DMSO-d6) δ 1.52–1.96 (4H,m), 2.30 (2H,br), 2.60(2H,br), 3.22(2H,br), 4.00–4.28(4H,m), 6.68(1H,d), 7.18(2H,d), 7.44(1H,d), 7.52(1H,s), 7.81(1H,d), 7.94(1H,d), 8.02(1H,d), 8.22(2H,d), 9.22(1H,br), 9.28(1H,br), 9.34(1H, br).

EXAMPLE 33

Synthesis of (4S)-5-[5-amidino-2-[4-carboxy-ethyl] phenoxy]-4-[(1-(1-pyridine-4-yl)piperidine-4-carbonyl) amino]pentanoic acid bistrifluoroacetate 365 mg (0.46 mmol) of (2S)-3-[4-amidino-2-[4-carbonyl-2-[(1-(1-pyridine-4-yl)piperidine-4-carbonyl)amino] butoxy]phenyl]acrylate bistrifluoroacetate was dissolved in a mixture of 10 ml of ethanol and 0.1 ml of N,N-dimethylformamide. 15 mg of 10% palladium/carbon (50% hydrous) was added to the obtained solution, and they were stirred in the presence of hydrogen overnight. The solvent was evaporated, and the obtained product was filtered through Celite and then treated in the same manner as that in step 9 in Example 1 to obtain the title compound.

Yield: 34.2 mg (0.046 mmol) (10%)

MS (ESI, m/z) 612 (MH+)

H-NMR (DMSO-d6) δ 1.50–2.00(4H,m), 2.30(2H,br), 2.50–2.70(2H,m), 2.85(2H,br), 3.20(2H,br), 3.95–4.30(6H, m), 7.20(2H,d), 7.38(3H,m), 8.00(1H,d), 8.30(2H,d), 9.14 (2H,m), 9.23(1H,br).

EXAMPLE 34

Synthesis of methyl 4-amidino-2-[2-[(1-(1-pyridine-4-yl)piperidine-4-carbonyl)amino]ethoxy]benzoate bistrifluoroacetate Step 1: Synthesis of methyl 2-(2-(t-butoxycarbonylamino) ethoxy)-4-cyanobenzoate 5 g (12.88 mmol) of 3-(2-(t-butoxycarbonylamino) ethoxy)-4-iodobenzonitrile was dissolved in 60 ml of N,N-dimethylformamide (dehydrated). 3.6 ml (25.8 mmol) of triethylamine, 10 ml (25.8 mmol) of methanol and 145 mg (0.644 mmol) of palladium acetate were added to the obtained solution, and they were stirred in the presence of carbon monoxide at 90° C. for 6 hours. The solvent was evaporated. After the treatment with ethyl acetate as the extraction solvent in an ordinary manner, the obtained crude product was purified by the silica gel column chromatography to obtain the title compound.

Yield: 4.11 g (12.82 mmol) (99.5%)

H-NMR (CDCl3) δ 1.44(9H,s), 3.61(2H,q), 3.94(3H,s), 4.12(2H,m), 5.38(1H,br), 7.21(1H, s), 7.38(1H,m), 7.87(1H, d).

Step 2: Synthesis of methyl 4-amidino-2-[2-[(1-(1-pyridine-4-yl)piperidine-4-carbonyl)amino]ethoxy]benzoate bistrifluoroacetate 1.5 g (4.68 mmol) of methyl 2-(2-(t-butoxycarbonylamino)ethoxy-4-cyanobenzoate was dissolved in a mixture of 15 ml of dioxane and 15 ml of 4 N solution of hydrogen chloride in dioxane, and the obtained solution was stirred at room temperature for 3 hours. The obtained crude product was dissolved in 6 ml of N,N-dimethylformamide (dehydrated). 0.32 g (1.29 mmol) of 1-(4-pyridyl)piperidine-4-carboxylic acid hydrochloride and 0.24 g (1.40 mmol) of 2-chloro-1,3-dimethylimidazolinium chloride were added to the obtained solution and then 1 ml (7.02 mmol) of triethylamine was added to the obtained mixture under cooling with ice, and they were stirred at room temperature overnight. After the treatment with chloroform as the extraction solvent in an ordinary manner, the obtained crude product was dissolved in a mixture of 2 ml of 4 N solution of hydrogen chloride in dioxane and 0.2 ml of ethanol, and they were stirred at room temperature for 3 days. The solvent was evaporated, and the residue was dissolved in 50 ml of ethanol. 0.14 g (2.45 mmol) of ammonium carbonate was added to the obtained solution, and they were stirred at room temperature overnight. The solvent was evaporated, and the obtained crude product was treated in the same manner as that in step 9 in Example 1 to obtain the title compound.

Yield: 92 mg (0.14 mmol) (12%)

MS (ESI, m/z) 426(MH+)

H-NMR (DMSO-d6) δ 1.50–1.90(4H,m), 2.60(2H,m), 3.23(2H,m), 3.45(2H,q), 3.85(3H,s), 4.18(3H,m), 7.20(2H, d), 7.44(1H,d), 7.53(1H,s), 7.80(1H,d), 8.09(1H,t), 8.22(2H, d), 9.40(2H,m), 9.43(1H,br).

EXAMPLE 35

Synthesis of ethyl 4-amidino-2-[2-[(1-(1-pyridine-4-yl)piperidine-4-carbonyl)amino]ethoxy]benzoate bistrifluoroacetate The title compound was obtained as a by-product in step 2 in Example 34.

Yield: 26 mg (0.039 mmol) (3%)

MS (ESI, m/z) 440(MH+)

H-NMR (DMSO-d6) δ 1.30(3H,t), 1.50–1.90(4H,m), 2.53–2.65(2H,m), 3.23(2H,t), 3.48(2H,q), 4.10–4.35(4H,m), 7.20(2H,d), 7.45(1H,d), 7.53(1H,s), 7.79(1H,d), 8.10(1H,t), 8.23(2H,d), 9.40(2H,br), 9.43(1H,br).

EXAMPLE 36

Synthesis of 4-amidino-2-[2-[(1-(1-pyridine-4-yl) piperidine-4-carbonyl)amino]ethoxy]benzoic acid bistrifluoroacetate 50 mg (0.077 mmol) of methyl 4-amidino-2-[2-[(1-(1-pyridine-4-yl)piperidine-4-carbonyl)amino]ethoxy] benzoate bistrifluoroacetate obtained in Step 2 in Example 34 was dissolved in 1 ml of 6 N aqueous hydrochloric acid solution, and the obtained solution was stirred at 90° C. for 3 hours. The solvent was evaporated, and the obtained crude product was treated in the same manner as that in step 9 in Example 1 to obtain the title compound.

Yield: 45.3 mg (0.071 mmol) (92%)

MS (ESI, m/z) 412 (MH+)

H-NMR (DMSO-d6) δ 1.50–1.67 (2H,m), 1.79–2.02 (2H, m), 2.53–2.74 (2H,m), 3.16–3.37 (2H,m), 3.47 (2H,q), 4.06–4,26 (3H,m), 7.20 (2H,d), 7.44 (1H,d), 7.53 (1H,br), 7.77 (1H,d), 8.09 (1H,t), 8.22 (2H,d), 9.42 (1H,br), 9.53 (2H,br).

EXAMPLE 37

Synthesis of N-[2-(5-amidino-2-hydroxymethylphenoxy)ethyl]-1-(1-(1-pyridine-4-yl) piperidine)carboxamide bistrifluoroacetate Step 1: Synthesis of 3-(2-(t-butoxycarbonylamino)ethoxy)-4-hydroxymethylbenzonitrile 4.15 g (12.95 mmol) of methyl 2-(2-(t-butoxycarbonylamino)ethoxy)-4-cyanobenzoate obtained in the same manner as that in step 1 in Example 34 was dissolved in 60 ml of tetrahydrofuran (dehydrated). 3.2 ml (129.5 mmol) of 2 M Lithium borohydride was added to the obtained solution under cooling with ice, and they were stirred at room temperature overnight.

The solvent was evaporated. After the treatment with ethyl acetate as the extraction solvent in an ordinary manner, the obtained crude product was purified by the silica gel column chromatography to obtain the title compound.

Yield: 2.38 g (8.12 mmol) (63%)

H-NMR (CDCl3) δ 1.41 (9H,s), 3.00 (1H,br), 3.60 (2H, br), 4.10 (2H,t), 4.70 (2H,d), 4.95 (1H,br), 7.07 (1H,s), 7.30 (1H,d), 7.41 (1H,d).

Step 2: Synthesis of N-[2-(5-amidino-2-hydroxymethylphenoxy)ethyl]-1-(1-(1-pyridine-4-yl)piperidine)carboxamide bistrifluoroacetate 2.38 g (8.12 mmol) of 3-(2-(t-butoxycarbonylamino)ethoxy)-4-hydroxymethylbenzonitrile was dissolved in a mixture of 20 ml of dioxane and 20 ml of 4 N solution of hydrogen chloride in dioxane, and the obtained solution was stirred at room temperature for 3 hours. The obtained crude product was dissolved in 10 ml of N,N-dimethylformamide (dehydrated). 1.25 g (5.1 mmol) of 1-(4-pyridyl)piperidine-4-carboxylic acid hydrochloride, 0.95 g (5.6 mmol) of 2-chloro-1,3-dimethylimidazolinium chloride and 4 ml (27.8 mmol) of triethylamine were added to the obtained solution, and then and they were stirred at room temperature overnight. After the treatment with dichloromethane as the extraction solvent in an ordinary manner, the obtained crude product was dissolved in a mixture of 20 ml of 4 N solution of hydrogen chloride in dioxane and 2 ml of ethanol, and they were stirred at room temperature for 3 days. The solvent was evaporated, and the residue was dissolved in 50 ml of ethanol. 1.3 g (23.15 mmol) of ammonium carbonate was added to the obtained solution, and they were stirred at room temperature overnight. The solvent was evaporated, and the obtained crude product was treated in the same manner as that in step 9 in Example 1 to obtain the title compound.

Yield: 275 mg (0.44 mmol) (11%)

MS (ESI, m/z) 398(MH+)

H-NMR (DMSO-d6) δ 1.50 (2H,br), 1.80 (2H,br), 2.60 (2H,br), 3.20 (2H,br), 3.47 (2H,m), 4.18–4.24 (3H,m), 4.58 (2H,s), 7.19 (2H,d), 7.35 (1H,s), 7.45(1H,d), 7.60(1H,d), 8.21(2H,d), 9.25(3H,m).

EXAMPLE 38

Synthesis of methyl 4-amidino-2-[2-(4-[1-(1-acetimidoyl)-4-piperidyloxy]benzoylamino)ethoxy]benzoate bistrifluoroacetate Step 1: Synthesis of methyl 4-amidino-2-[2-(4-[1-(1-acetimidoyl)-4-piperidyloxy]benzoylamino)ethoxy]benzoate bistrifluoroacetate 0.586 g (2.35 mmol) of methyl 3-(2-aminoethoxy)-4-cyanobenzoate hydrochloride was dissolved in 10 ml of N,N-dimethylformamide (dehydrated). 0.82 g (2.56 mmol) of 4-(1-t-butoxycarbonyl-4-piperidyloxy)benzoic acid and 0.48 g (2.82 mmol) of 2-chloro-1,3-dimethylimidazolinium chloride were added to the obtained solution, and then 2 ml (14.1 mmol) of triethylamine was added to the obtained mixture under cooling with ice. They were stirred at room temperature overnight. The solvent was evaporated, and the obtained crude product was dissolved in a mixture of 10 ml of dioxane and 10 ml of 4 N solution of hydrogen chloride in dioxane, and the obtained solution was stirred at room temperature for 4 hours. The solvent was evaporated, and the residue was dissolved in 12 ml of ethanol. 0.87 g (7.05 mmol) of ethyl acetimidate hydrochloride and 1.64 ml (11.75 mmol) of triethylamine were added to the obtained solution, and they were stirred at room temperature overnight. The solvent was evaporated, and the residue was dissolved in a mixture of 20 ml of 4 N solution of hydrogen chloride in dioxane and 3 ml of ethanol, and the obtained solution was stirred at room temperature for 3 days. The solvent was evaporated, and the obtained crude product was dissolved in 10 ml of ethanol. 0.67 g (11.75 mmol) of ammonium carbonate was added to the obtained solution, and they were stirred at room temperature overnight. The solvent was evaporated, and the obtained crude product was treated in the same manner as that in step 9 in Example 1 to obtain the title compound.

Yield: 484.5 mg (0.68 mmol) (29%)

MS (ESI, m/z) 480(MH−)

H-NMR (DMSO-d6) δ 1.77(2H,br), 2.08(2H,br), 2.50 (3H,s), 3.48–3.70(6H,m), 3.79(3H,s), 4.28(2H,br), 4.80(1H, br), 7.07(2H,d), 7.44(1H,d), 7.58(1H,s), 7.75–7.89(3H,m), 8.52(1H,br), 8.62(1H,br), 9.17(1H,br), 9.37 (1H,br), 9.42 (1H,br).

EXAMPLE 39

Synthesis of ethyl 4-amidino-2-[2-(4-[1-(1-acetimidoyl)-4-piperidyloxy]benzoylamino)ethoxy]benzoate bistrifluoroacetate The title compound was obtained as a by-product in step 2 in Example 38.

Yield: 165.6 mg (0.23 mmol) (10%)

MS (ESI, m/z) 494(MH−)

H-NMR (DMSO-d6) δ 1.25 (3H,t), 1.77(2H,br), 2.08(2H, br), 2.29(3H,s), 3.48–3.85(6H,m), 4.20–4.35 (4H,m), 4.80 (1H,br), 7.07(2H,d), 7.44 (1H,d), 7.58(1H,br), 7.77(1H,br), 7.84 (2H,d), 8.52(1H,br), 8.63(1H,br), 9.17(1H,br), 9.37 (1H,br), 9.42 (1H,br).

EXAMPLE 40

Synthesis of 4-amidino-2-[2-(4-[1-(1-acetimidoyl)-4-piperidyloxy]benzoylamino)ethoxy]benzoic acid bistrifluoroacetate 0.3 g (0.423 mmol) of ethyl 4-amidino-2-[2-(4-[1-(1-acetimidoyl)-4-piperidyloxy]benzoylamino)ethoxy]benzoate bistrifluoroacetate obtained in Example 39 was dissolved in 10 ml of concentrated hydrochloric acid solution, and the obtained solution was stirred at 80° C. for 3 hours. The solvent was evaporated, and the obtained crude product was treated in the same manner as that in step 9 in Example 1 to obtain the title compound.

Yield: 231.6 mg (0.333 mmol) (79%)

MS (ESI, m/z) 468 (MH+)

H-NMR (DMSO-d6) δ 1.77(2H,br), 2.08(2H,br), 2.29 (3H,s), 3.48–3.85(6H,m), 4.28(2H,t), 4.80(1H,br), 7.07(2H, d), 7.42(1H,d), 7.58(1H,br), 7.78(1H,d), 7.84(2H,d), 8.50 (1H,t), 8.63(1H,br), 9.17 (1H,br), 9.38(2H,br).

EXAMPLE 41

Synthesis of 2-[4-amidino-2-[2-[(1-(1-pyridine-4-yl)piperidine-4-carbonyl)amino]ethoxy]phenyl]vinylsulfonic acid bistrifluoroacetate Step 1: Synthesis of 3-(2-(t-butoxycarbonylamino)ethoxy)-4-formylbenzonitrile 0.3 g (1.03 mmol) of 3-(2-(t-butoxycarbonylamino)ethoxy)-4-hydroxymethylbenzonitrile obtained in the same manner as that in step 1 in Example 37 was dissolved in 3 ml of dichloromethane (dehydrated). 0.36 g (4.1 mmol) of activated manganese dioxide was added to the obtained solution in the presence of argon at room temperature, and they were stirred overnight. The reaction liquid was filtered through Celite to obtain the title compound.

Yield: 279 mg (0.962 mmol) (93%)

MS (ESI, m/z) 291 (MH−)

H-NMR (CDCl3) δ 1.53 (9H,s), 3.62 (2H,q), 4.20 (2H,t), 4.95 (1H, br), 7.35(2H,m), 7.93 (1H,d), 10.50 (1H,s).

Step 2: Synthesis of ethyl 3-[2-(2-(t-butoxycarbonylamino)ethoxy)-4-cyanophenyl]ethylenesulfonate 280 mg (1.15 mmol) of diethylphosphorylmethane sulfonate was dissolved in 5 ml of triethylamine (dehydrated). 0.75 ml (1.15 mmol) of 1.54 M solution of n-butyllithium in hexane was added to the obtained solution in the presence of argon at −78°C., and they were stirred for 20 minutes. 279 mg (0.962 mmol) of 3-(2-(t-butoxycarbonylamino)ethoxy)-4-formylbenzonitrile was added to the obtained mixture, and they were stirred at −78° C. for 45 minutes and then at room temperature for 3 hours. The solvent was evaporated. After the treatment with dichloromethane as the extraction solvent in an ordinary manner, the obtained crude product was purified by the silica gel column chromatography to obtain the title compound.

Yield: 197 mg (0.498 mmol) (52%)

MS (ESI, m/z) 367 (MH−)

H-NMR (CDCl3) δ 1.35–1.50 (12H,m), 3.58 (2H,br), 4.10–4.30 (4H,m), 5.00 (1H,br), 7.00 (1H,d), 7.20 (1H,s), 7.28 (1H,d), 7.63 (1H,d), 7.63 (1H,d), 7.78(1H,d).

Step 3: Synthesis of 2-[4-amidino-2-[2-[(1-(1-pyridine-4-yl)piperidine-4-carbonyl)amino]ethoxy]phenyl]vinylsulfonic acid bistrifluoroacetate 197 mg (0.498 mmol) of ethyl 3-[2-(2-(t-butoxycarbonylamino)ethoxy)-4-cyanophenyl)ethylenesulfonate was dissolved in a mixture of 2 ml of dioxane and 2 ml of 4 N solution of hydrogen chloride in dioxane, and the obtained solution was stirred at room temperature for 3 hours. The solvent was evaporated, and the obtained crude product was dissolved in 3 ml of N,N-dimethylformamide (dehydrated). 134 mg (0.548 mmol) of 1-(4-pyridyl)-piperidine-4-carboxylic acid hydrochloride, 101 mg (0.598 mmol) of 2-chloro-1,3-dimethylimidazolium chloride and 0.4 ml (3 mmol) of triethylamine were added to the obtained solution, and they were stirred at room temperature for 3 hours. The solvent was evaporated, and the residue was dissolved in a mixture of 2 ml of ethanol and 20 ml of 4 N solution of hydrogen chloride in dioxane, and the obtained solution was stirred at room temperature for 3 days. The solvent was evaporated, and the residue was dissolved in 20 ml of ethanol. 0.41 g (2.5 mmol) of ammonium carbonate was added to the obtained solution, and they were stirred at room temperature overnight. The solvent was evaporated, and the obtained crude product was treated in the same manner as that in step 9 in Example 1 to obtain the title compound.

Yield: 120.8 mg (0.172 mmol) (35%)

MS (ESI, m/z) 476(MH+)

H-NMR (DMSO-d6) δ 1.48–1.70 (2H,m), 1.80–2.00 (2H, m), 2.55–3.05 (3H,m), 3.22 (2H,t), 3.50 (2H,br), 4.22 (2H, br), 7.03–7.08 (1H,d), 7.18–7.50 (5H,m), 7.80 (1H,d), 8.19 (2H,d),9.05 (2H,s), 9.30 (2H,s).

Example 42

Synthesis of 2-[4-amidino-2-[2-[(1-(1-pyridine-4-yl)piperidine-4-carbonyl) amino]ethoxy]phenyl] ethanesulfonic acid bistrifluoroacetate 72.2 mg (0.103 mmol) of 2-(4-amidino-2-[2-[(1-(1-pyridine-4-yl)piperidine-4-carbonyl) amino]ethoxy]phenyl) vinylsulfonic acid bistrifluoroacetate obtained in step 3 in Example 41 was dissolved in 20 ml of ethanol. 30 mg of 10% palladium/carbon (50% hydrous) was added to the obtained solution in the presence of argon, and they were stirred at room temperature in the presence of hydrogen overnight. After the filtration through Celite, the obtained crude product was treated in the same manner as that in step 9 in Example 1 to obtain the title compound.

Yield: 10.5 mg (0.015 mmol) (15%)

MS (ESI, m/z) 474 (MH+)

H-NMR (DMSO-d6) δ 1.48–1.65(2H,m), 1.80–1.95 (2H, m), 2.60–3.05(5H,m), 3.20 (2H,br), 3.53 (2H,br), 4.08 (2H, br), 4.20 (2H,d), 7.14–7.25 (3H,m), 7.34 (1H,s), 7.41 (1H,d), 8.20 (2H,d), 8.48 (1H,br), 8.98 (2H,br), 9.22 (2H,br).

EXAMPLE 43

Synthesis of N-[2-(5-amidino-2-hydroxypropylphenoxy)ethyl]-1-(1-pyridine-4-yl) piperidine)carboxamide bistrifluoroacetate Step 1: Synthesis of 3-(2-(t-butoxycarbonylamino)ethoxy)-4-(3-hydroxypropyl)benzonitrile 1.1 g (3.04 mmol) of ethyl 3-[2-(2-(t-butoxycarbonylamino)ethoxy)-4-cyanophenyl]propionate was dissolved in 15 ml of tetrahydrofuran (dehydrated). 1.5 ml (2.3 mmol) of 2 M Lithium borohydride was added to the obtained solution under cooling with ice, and they were stirred at room temperature overnight. The solvent was evaporated. After the treatment with ethyl acetate as the extraction solvent in an ordinary manner, the obtained crude product was purified by the silica gel column chromatography to obtain the title compound.

Yield: 524 mg (1.64 mmol) (54%)

H-NMR (CDCl3) δ 1.45 (9H,s), 1.80 (2H,br), 2.80 (2H,t), 3.54–3.69 (4H,m), 4.02 (2H,t), 5.30 (1H,br), 7.03 (1H,s), 7.23–7.26 (2H,m).

Step 2: Synthesis of N-[2-(5-amidino-2-hydroxypropylphenoxy)ethyl]-1-(1-pyridine-4-yl) piperidine)carboxamide bistrifluoroacetate:

524 mg (1.64 mmol) of 3-(2-(t-butoxycarbonylamino)ethoxy)-4-(3-hydroxypropyl)benzonitrile was dissolved in a mixture of 4 ml of dioxane and 4 ml of 4 N solution of hydrogen chloride in dioxane, and the obtained solution was stirred at room temperature for 2 hours. The solvent was evaporated and the obtained crude product was dissolved in 5 ml of N,N-dimethylformamide (dehydrated). 440 mg (1.80 mmol) of 1-(4-pyridyl)piperidine-4-carboxylic acid hydrochloride, 330 mg (1.97 mmol) of 2-chloro-1,3-dimethylimidazolinium chloride and 1.4 ml (9.84 mmol) of triethylamine were added to the obtained solution, and they were stirred at room temperature overnight. The solvent was evaporated, and the obtained crude product was treated with dichloromethane as the extraction solvent in an ordinary manner, and the obtained crude product was dissolved in a mixture of 10 ml of 4 N solution of hydrogen chloride in dioxane and 1 ml of ethanol, and they were stirred at room temperature for 3 days. The solvent was evaporated, and the residue was dissolved in 10 ml of ethanol. 0.46 g (8.2 mmol) of ammonium carbonate was added to the obtained solution, and they were stirred at room temperature overnight. The solvent was evaporated, and the obtained crude product was treated in the same manner as that in step 9 in Example 1 to obtain the title compound.

Yield: 178.5 mg (0.273 mmol) (17%)

MS (ESI, m/z) 426 (MH+)

H-NMR (DMSO-d6) δ 1.49–1.95 (6H,m), 2.55–2.75 (4H, m), 3.25 (2H,t), 3.50 (4H,br), 4.09 (2H,t), 4.20 (1H,br), 7.18 (1H,s), 7.35 (1H,d), 8.22(1H,d),9.19 (2H,br), 9.23 (2H,br).

EXAMPLE 44

Synthesis of diethyl 2-(4-amidino-2-[2-[(1-(1-pyridine-4-yl)piperidine-4-carbonyl)amino]ethoxy]phenyl)vinylphosphate bistrifluoroacetate Step 1: Synthesis of diethyl 2-[(2-(2-t-butoxycarbonylamino)ethoxy)-4-cyanophenyl]vinylphosphate 0.54 ml (2.18 mmol) of tetraethylmethylene diphosphonate was dissolved in 10 ml of tetrahydrofuran (dehydrated). 1.5 ml (2.31 mmol) of 1.54 M solution of n-butyllithium in hexane was added to the obtained solution in the presence of argon at −78° C., and they were stirred for 20 minutes. 527 mg (1.82 mmol) of 3-(2-(t-butoxycarbonylamino)ethoxy)-4-formylbenzonitrile obtained in the same manner as that in step 1 in Example 41 was added to the obtained mixture, and they were stirred at −78° C. for 45 minutes and then at room temperature for 3 hours. The solvent was evaporated. After the treatment with dichloromethane as the extraction solvent in an ordinary manner, the obtained crude product was purified by the silica gel column chromatography to obtain the title compound.

Yield: 0.45 g (1.06 mmol) (58%)

H-NMR (CDCl3) δ 1.17–1.42 (6H,m), 1.47 (9H,s), 3.60 (2H,br), 3.96–4.23 (6H,m), 5.00 (1H,br), 6.40 (2H,m), 7.15 (1H,s), 7.27 (1H,d), 7.58 (1H,d). Step 2: Synthesis of diethyl [2-(4-amidino-2-[2-[(1-(1-pyridine-4-yl)piperidine-4-carbonyl)amino]ethoxy]phenyl)vinylphosphate bistrifluoroacetate 0.45 g (1.06 mmol) of diethyl [2-[(2-(2-t-butoxycarbonylamino)ethoxy)-4-cyanophenyl]vinyl]phosphate was dissolved in a mixture of 5 ml of dioxane and 5 ml of 4 N solution of hydrogen chloride in dioxane, and the obtained solution was stirred at room temperature for 3 hours. The solvent was evaporated, and the obtained crude product was dissolved in 10 ml of N,N-dimethylformamide (dehydrated). 0.29 g (1.2 mmol) of 1-(4-pyridyl)-4-piperidinecarboxylic acid hydrochloride, 0.5 g (2.8 mmol) of 2-chloro-1,3-dimethylimidazonium chloride and 1.8 ml (12.8 mmol) of triethylamine were added to the obtained solution, and they were stirred overnight. After the treatment with dichloromethane as the extraction solvent in an ordinary manner, the obtained crude product was dissolved in a mixture of 5 ml of 4 N hydrogen chloride in dioxane and 0.5 ml of ethanol, and the obtained solution was stirred at room temperature for 3 days. The solvent was evaporated, and the residue was dissolved in 5 ml of ethanol. 0.19 g (3.35 mmol) of ammonium carbonate was added to the obtained solution, and they were stirred at room temperature overnight. The solvent was evaporated, and the obtained crude product was treated in the same manner as that in step 9 in Example 1 to obtain the title compound.

Yield: 155 mg (0.204 mmol) (31%)

MS (ESI, m/z) 530 (MH+)

H-NMR (DMSO-d6) δ 1.26 (6H,t), 1.50–1.92 (4H,m), 2.58 (2H,br), 3.22 (2H,t), 3.50 (2H,br), 4.03 (4H,m), 4.20 (3H,br), 6.77 (2H,m), 7.19 (2H,d), 7.40–7.74 (3H,m),7.96 (1H,d), 8.21 (2H,d),9.33(2H,br), 9.36(2H,br).

EXAMPLE 45

Synthesis of monoethyl [2-(4-amidino-2-[2-[(1-(1-pyridine-4-yl)piperidine-4-carbonyl)amino]ethoxy]phenyl)vinyl]phosphate bistrifluoroacetate This compound was a by-product obtained in step 2 in Example 44.

Yield: 63.4 mg (0.087 mmol) (13%)

MS (ESI, m/z) 502 (MH+)

H-NMR (DMSO-d6) δ 1.23 (3H,t), 1.50–1.95 (4H,m), 2.58 (2H,br), 3.22 (2H,t), 3.50 (2H,br), 3.95 (2H,m), 4.22 (3H,br), 6.71 (2H,m), 7.18 (2H,d), 7.38–7.66 (3H,m),7.92 (1H,d), 8.20 (2H,d),9.21(2H,br), 9.34(2H,br).

Example 46

Synthesis of monoethyl [2-(4-amidino-2-[2-[(1-(1-pyridine-4-yl)piperidine-4-carbonyl)amino]ethoxy]phenyl)ethyl]phosphate bistrifluoroacetate 63.4 mg (0.087 mmol) of monoethyl [2-(4-amidino-2-[2-[(1-(1-pyridine-4-yl)piperidine-4-carbonyl)amino]ethoxy]phenyl)vinyl]phosphate bistrifluoroacetate was dissolved in 2 ml of ethanol. 10 mg of 10% palladium/carbon (50% hydrous) was added to the obtained solution in the presence of argon, and they were stirred in the presence of hydrogen at room temperature overnight. 2 ml of water was added to the reaction mixture. The solvent was evaporated, and the obtained crude product was treated in the same manner as that in step 9 in Example 1 to obtain the title compound.

Yield: 43.1 mg (0.059 mmol) (68%)

MS (ESI, m/z) 504 (MH+)

H-NMR (DMSO-d6) δ 1.20 (3H,t), 1.58 (2H,br), 1.80–1.96 (4H,m), 2.62 (2H,br), 2.80 (2H,br), 3.21 (2H,t), 3.49 (2H,q), 3.88–3.98 (2H,m), 4.12 (2H,t) 4.20 (1H,br), 7.18 (2H,d), 7.37–7.42 (3H,m), 8.21 (2H,d), 8.28 (1H,br), 9.18(2H,br), 9.25(2H,br).

EXAMPLE 47

Synthesis of diethyl [2-(4-amidino-2-[2-[(1-(1-pyridine-4-yl)piperidine-4-carbonyl)amino]ethoxy]phenyl)ethyl]phosphate bistrifluoroacetate 155 mg (0.204 mmol) of diethyl [2-(4-amidino-2-[2-[(1-(1-pyridine-4-yl)piperidine-4-carbonyl)amino]ethoxy]phenyl)vinyl]phosphate bistrifluoroacetate was dissolved in 2 ml of ethanol. 20 mg of 10% palladium/carbon (50% hydrous) was added to the obtained solution in the presence of argon, and they were stirred in the presence of hydrogen at room temperature overnight. 2 ml of water was added to the reaction mixture. The solvent was evaporated, and the obtained crude product was treated in the same manner as that in step 9 in Example 1 to obtain the title compound.

Yield: 26.75 mg (0.0352 mmol) (17%)

MS (ESI, m/z) 532 (MH+)

H-NMR (DMSO-d6) δ 1.19 (6H,t), 1.59 (2H,br), 1.80 (2H,br), 2.01 (2H,br), 2.58 (2H,br), 2.82 (2H,br), 3.19 (2H,t), 3.47 (2H,br), 3.91–4.00 (4H,m), 4.09–4.21(3H,m), 7.17 (2H,d), 7.36–7.41 (3H,m),8.19 (3H,br), 9.25(2H,br), 9.27(2H,br).

EXAMPLE 48

Synthesis of 3-[4-N-ethoxycarbonylamidino-2-(2-((1-(pyridine-4-yl)piperidine-4-carbonyl)amino)ethoxy)phenyl]propionic acid bistrifluoroacetate 200 mg (0.299 mmol) of 3-[4-amidino-2-(2-((1-(pyridine-4-yl)piperidine-4-carbonyl)amino)ethoxy)phenyl]propionic acid bistrifluoroacetate was dissolved in 5 ml of DMF. 0.124 ml (0.897 mmol) of triethylamine and 0.028 ml (0.299 mmol) of ethyl chloroformate were added to the obtained solution, and they were stirred at room temperature overnight. The solvent was evaporated, and the obtained crude product was treated in the same manner as that in step 9 in Example 1 to obtain the title compound.

Yield: 36 mg (0.049 mmol) (16%)

MS (ESI, m/z) 512 (MH+)

H-NMR (DMSO) δ 1.24 (3H, t), 1.44–1.62 (2H, m), 1.76–1.91 (2H, m), 2.32 (2H, t), 2.48–2.53 (1H, m), 2.81 (2H, t), 3.10–3.23 (2H, m), 3.46 (2H, dt), 4.08 (2H, t), 4.18 (2H, q), 4.19–4.23 (2H, m), 6.77 (1H br), 7.17 (2H, d), 7.25 (1H, br), 7.42 (2H, d ), 8.15 (1H, d), 8.20 (2H, d)

EXAMPLE 49

Synthesis of 3-[4-N-hydroxyamidino-2-(2-((1-(pyridine-4-yl)piperidine-4-carbonyl)amino)ethoxy)phenyl]propionic acid bistrifluoroacetate 50 mg (0.070 mmol) of ethyl 3-[4-N-hydroxyamidino-2-(2-((1-(pyridine-4-yl)piperidine-4-carbonyl)amino)ethoxy)phenyl]propionate bistrifluoroacetate was dissolved in 10 ml of 6 N aqueous hydrochloric acid solution, and the obtained solution was stirred at 60° C. for 2 hours.

The solvent was evaporated, and the obtained crude product was treated in the same manner as that in step 9 in Example 1 to obtain the title compound.

Yield: 24 mg (0.035 mmol) (50%)
MS (ESI, m/z) 455 (MH+)
H-NMR (DMSO) δ 1.44–1.65 (2H, m), 1.74–1.88 (2H, m), 2.48–2.56 (1H, m), 2.53 (2H,t), 2.84 (2H, t), 3.11–3.24 (2H, m), 3.45 (2H, dt), 4.08 (2H, t), 4.11–4.23 (2H, m), 7.16 (2H, d), 7.24 (2H, br), 7.34 (1H, d), 8.17 (1H, d ), 8.18 (2H, d), 8.92 (2H, br)

Example 50

Synthesis of 3-[4-N-acetoxyamidino-2-(2-((1-(pyridine-4-yl)piperidine-4-carbonyl)amino)ethoxy)phenyl]propionic acid bistrifluoroacetate 24 mg (0.035 mmol) of 3-[4-N-hydroxyamidino-2-(2-((1-(pyridine-4-yl)piperidine-4-carbonyl)amino)ethoxy)phenyl]propionic acid bistrifluoroacetate was dissolved in a mixture of 5 ml of acetic acid and 0.08 ml of acetic anhydride, and the obtained solution was stirred at room temperature for 3 hours. The solvent was evaporated, and the obtained crude product was treated in the same manner as that in step 9 in Example 1 to obtain the title compound.

Yield: 2.6 mg (0.0035 mmol) (10%)
MS (ESI, m/z) 498 (MH+)
H-NMR (DMSO) δ 1.44–1.63 (2H, m), 1.78–1.90 (2H, m), 2.11 (3H, s), 2.48–2.56 (1H, m), 2.53 (2H, t), 2.80 (2H, t), 3.08–3.23 (2H, m), 3.45 (2H, t) 4.04 (2H, t), 4.13–4.25 (2H, m), 6.74 (2H, br), 7.16–7.23 (5H, m), 8.11 (1H, t), 8.18 (2H, d)

EXAMPLE 51

Synthesis of 3-[4-amidino-2-]2-(4-(1-methyl-2-imidazoline-2-yl)benzoylamino)ethoxy)phenyl]-2-oxopropionic acid bistrifluoroacetate Step 1: Synthesis of 4-(1-methyl-2-imidazoline-2-yl)benzoic acid monohydrochloride 1.8 g (10.3 mmol) of ethyl 4-cyanobenzoate was dissolved in a mixture of 20 ml of 4 N solution of hydrogen chloride in dioxane and 5 ml of ethanol, and the obtained solution was stirred at room temperature for 3 days. The solvent was evaporated, and the residue was washed with ethyl acetate. The obtained crude product was dissolved in 20 ml of ethanol. 1.52 g (20.6 mmol) of N-methylethylenediamine was added to the obtained solution, and they were heated under reflux for 6 hours. The solvent was evaporated, and the obtained crude product was treated with dichloromethane as the extraction solvent in an ordinary manner. The obtained crude product was dissolved in 10 ml of concentrated hydrochloric acid, and the obtained solution was stirred at 50° C. overnight. The solvent was evaporated to obtain the crude title compound.

Yield: 1.37 g (5.71 mmol) (55%)

Step 2: Synthesis of 3-hydroxy-4-iodobenzoic acid 30.0 g (217 mmol) of 3-hydroxybenzoic acid was dissolved in 200 ml of acetic acid. 53.0 g (326 mmol) of iodine monochloride was added to the obtained solution at room temperature. After stirring at 45° C. for 15 hours, the solvent was evaporated under reduced pressure, and the obtained residue was washed with 500 ml of 1% aqueous sodium thiosulfate solution twice and then with 500 ml of water twice, and dried to solid at 80° C. under reduced pressure to obtain the title compound.

Yield: 17.2 g (65.2 mmol) (30%)
MS (FAB, m/z) 265 (MH+)
H-NMR (DMSO-d6) δ: 7.13 (1H, dd), 7.43 (1H, d), 7.80 (1H, d)

Step 3 Synthesis of 3-hydroxy-4-iodobenzonitrile 22.3 g (89.7 mmol) of 3-hydroxy-4-iodobenzoic acid was dissolved in 300 ml of tetrahydrofuran. 19.7 ml (206 mmol) of ethyl chloroformate and 28.7 ml (206 mmol) of triethylamine were added to the obtained solution at 0° C. After stirring for 15 minutes, triethylamine hydrochloride thus formed was filtered out. The filtrate was added to 300 ml of a tetrahydrofuran solution, obtained by bubbling with ammonia, at 0° C. After stirring at room temperature for 10 hours, the solvent was evaporated under reduced pressure, and the residue was dissolved in 450 ml of dioxane. 17.4 ml (117 mmol) of anhydrous trifluoroacetic acid and 21.8 ml (269 mmol) of pyridine were added to the obtained solution at 0° C. After stirring at room temperature for 18 hours, the solvent was evaporated under reduced pressure, and the residue was treated with chloroform as the extraction solvent in an ordinary manner to obtain an oily residue. The residue was dissolved in 180 ml of tetrahydrofuran/methanol (1:1). 90 ml (90.0 mmol) of 1 N aqueous sodium hydroxide solution was added to the obtained solution at room temperature. After stirring them for 4 hours, the solvent was evaporated under reduced pressure, and the obtained residue was washed with dichloromethane. The reaction mixture was acidified with 1 N hydrogen chloride and then treated with ethyl acetate as the extraction solvent in an ordinary manner to obtain the crude product, which was purified by the silica gel column chromatography to obtain the title compound.

Yield: 9.29 g (37.9 mmol) (42%)
MS (FAB, m/z) 246 (MH+)
H-NMR (CDCl3) δ:5.63 (1H, br), 6.96 (1H, dd), 7.23 (1H, d), 7.79 (1H, d)

Step 4: Synthesis of t-butyl (2-bromoethyl)carbamate 9.22 g (45 mmol) of 2-bromoethylamine hydrobromide was dissolved in 100 ml of dichloromethane. 7.64 g (35 mmol) of di-t-butyl dicarbonate, 10.0 g (99 mmol) of triethylamine and 100 mg (0.82 mmol) of 4-(dimethylamino)pyridine were added to the obtained solution, and they were stirred overnight. After the treatment with dichloromethane as the extraction solvent in an ordinary manner, the title compound was obtained.

Yield: 5.99 g (26.7 mmol) (76%)
H-NMR (CDCl3) δ:1.45 (9H, s), 3.46 (2H, dt), 3.51 (2H, t), 4.95 (1H, br)

Step 5: Synthesis of 3-[2-(t-butoxycarbonylamino)ethoxy]-4-iodobenzonitrile 18.5 g (82.6 mmol) of t-butyl (2-bromoethyl)carbamate was dissolved in 200 ml of DMF. 10.1 g (41.3 mmol) of 3-hydroxy-4-iodobenzonitrile and 5.7 g (41.3 mmol) of potassium carbonate were added to the obtained solution, and they were stirred at 75° C. for 3 hours. After the treatment with ethyl acetate as the extraction solvent in an ordinary manner, the title compound was obtained.

Yield: 11.0 g (28.4 mmol) (69%)

H-NMR (CDCl3) δ:1.46 (9H, s), 3.62 (2H, dt), 4.12 (2H, t), 7.02 (2H, d),7.88 (2H, d).

Step 6: Synthesis of methyl 2-acetylamino-3-[2-(2-(t-butoxycarbonylamino)ethoxy)-4-cyanophenyl]acrylate 18.0 g (46.4 mmol) of 3-[2-(t-butoxycarbonylamino) ethoxy]-4-iodobenzonitrile was dissolved in 200 ml of DMF. 13.3 g (92.8 mmol) of methyl 2-acetamidoacrylate, 2.82 g (9.28 mmol) of tris(2-methylphenyl)phosphine, 1.04 g (4.64 mmol) of palladium acetate and 12.9 ml (92.8 mmol) of triethylamine were added to the obtained solution, and they were stirred at 115° C. for 4 hours. The solvent was evaporated, and the obtained crude product was purified by the silica gel column chromatography to obtain the title compound.

Yield: 12.2 g (30.3 mmol) (65%)

H-NMR (CDCl3) δ: 1.45 (9H, s), 2.03 (3H, s), 3.58 (2H, dt), 3.89 (3H, s), 4.18 (2H, t), 7.17 (1H, br), 7.23 (1H, d), 7.35–7.42 (2H, m)

Step 7: Synthesis of methyl 2-acetylamino-3-[4-cyano-2-(2-(4-(1-methyl-2-imidazoline-2-yl)benzoylamino)ethoxy) phenyl]acrylate mono-trifluoroacetate 2.09 g (5.19 mmol) of methyl 2-acetylamino-3-[2-(2-(t-butoxycarbonylamino)ethoxy)-4-cyanophenyl]acrylate was dissolved in 10 ml of 4 N solution of hydrogen chloride in dioxane and 10 ml of dioxane, and the obtained solution was stirred at room temperature for 4 hours. The solvent was evaporated, and the residue was dissolved in 10 ml of DMF. 1.37 g (5.71 mmol) of 4-(1-methyl-2-imidazoline-2-yl) benzoic acid monohydrochloride, 1.10 g (5.71 mmol) of 1-(3-dimethylaminopropyl)-3-ethylcarbodiimide hydrochloride, 777 mg (5.71 mmol) of 1-hydroxybenzotriazole and 2.17 ml (15.6 mmol) of triethylamine were added to the obtained solution, and they were stirred at room temperature overnight. The solvent was evaporated, and the obtained crude product was subjected to the reversed phase high-performance liquid chromatography with silica gel chemically bonded with octadodecyl group. After the elution with a mixed solution of water and acetonitrile containing 0.1% (v/v) of trifluoroacetic acid, the intended fraction was freeze-dried to obtain the title compound.

Yield: 2.0 g (3.32 mmol) (64%)

H-NMR (DMSO-d6) δ:1.95 (3H, s), 3.06 (3H, s), 3.65 (3H, s), 3.70 (2H, dt), 3.76–4.13 (4H, m), 4.29 (2H, t), 7.20 (1H, s), 7.44 (1H, d), 7.63 (1H, d), 7.69 (1H, d), 7.79 (2H, d), 8.06 (2H, d), 8.94 (1H, t), 9.69 (1H, br)

Step 8: Synthesis of 3-[4-amidino-2-(2-(4-(1-methyl-2-imidazoline-2-yl)benzoylamino)ethoxy)phenyl]-2-oxopropionic acid bistrifluoroacetate 2.0 g (3.32 mmol) of methyl 2-acetylamino-3-[4-cyano-2-(2-(4-(1-methyl-2-imidazoline-2-yl)benzoylamino) ethoxy)phenyl]acrylate mono-trifluoroacetate was dissolved in a mixture of 25 ml of 4 N solution of hydrogen chloride in dioxane and 5 ml of ethanol, and the obtained solution was stirred at room temperature for 4 days. The solvent was evaporated, and the residue was dissolved in 20 ml of ethanol. 564 mg of ammonium carbonate was added to the obtained solution, and they were stirred at room temperature overnight. The solvent was evaporated, and the residue was dissolved in 10 ml of 6 N hydrochloric acid, and the obtained solution was stirred at 80° C. for 4 hours. The solvent was evaporated, and the obtained crude product was treated in the same manner as that in step 7 in Example 51 to obtain the title compound.

Yield: 430 mg (0.633 mmol) (19%)

MS (ESI, m/z) 452 (MH+)

H-NMR (DMSO-d6) δ:3.05 (3H, s), 3.60–3.80 (2H, m), 3.78–4.40 (6H, m), 4.31 (2H, t), 6.81 (1H, s), 7.37–7.49 (3H, m), 7.73–7.85 (3H, m), 8.03–8.12 (3H, m), 9.05 (1H, t), 9.19–9.37 (5H, m)

EXAMPLE 52

Synthesis of 3-[4-amidino-2-(2-((1-(1-methylpyridinium-4-yl)piperidine-4-carbonyl) amino)ethoxy)phenyl]-2-oxopropionic acid bistrifluoroacetate Step 1: Synthesis of 1-(1-methylpyridinium-4-yl) piperidinecarboxylic acid 2.0 g (8.51 mmol) of ethyl 1-(4-pyridyl)-4-piperidinecarboxylate was dissolved in 10 ml of methyl iodide, and the obtained solution was stirred at 40° C. for 4 hours. The solvent was evaporated, and the obtained crude product was dissolved in 10 ml of concentrated hydrochloric acid, and the obtained solution was stirred at 70° C. overnight. The solvent was evaporated to obtain the title compound.

Yield: 1.2 g (5.48 mmol)

Step 2: Synthesis of methyl 2-acetylamino-3-[4-cyano-2-(2-((1-(1-methylpyridinium-4-yl)piperidine-4-carbonyl) amino)ethoxy)phenyl]acrylate 1.16 g (2.88 mmol) of methyl 2-acetylamino-3-[2-(2-(t-butoxycarbonylamino)ethoxy)-4-cyanophenyl]acrylate was dissolved in a mixture of 5 ml of 4 N solution of hydrogen chloride in dioxane and 5 ml of dioxane, and the obtained solution was stirred at room temperature for-4 hours. The solvent was evaporated, and the residue was dissolved in 10 ml of DMF. 700 mg (3.17 mmol) of 1-(1-methylpyridinium-4-yl)piperidinecarboxylic acid, 1.47 g (3.17 mmol) of bromotripyrrolidinophosphonium hexafluorophosphate and 1.20 ml (8.64 mmol) of triethylamine were added to the obtained solution, and they were stirred at room temperature overnight. The solvent was evaporated, and the obtained crude product was treated in the same manner as that in step 7 in Example 51 to obtain the title compound.

Yield: 710 mg (1.41 mmol) (49%)

H-NMR (DMSO-d6) δ:1.47–1.68 (2H, m), 1.76–1.89 (2H, m), 1.96 (3H, s), 2.53–2.64 (1H, m), 3.13–3.30 (2H, m), 3.44 (2H, dt), 3.70 (3H, s), 3.88 (3H, s), (4H, m), 7.18 (1H, br), 7.22 (2H, d), 7.43 (1H, d), 7.58 (1H, br), 7.69 (1H, d), 8.10 (1H, t), 8.21 (2H, d), 9.69 (1H, br)

Step 3: Synthesis of 3-[4-amidino-2-(2-((1-(1-methylpyridinium-4-yl)piperidine-4-carbonyl)amino) ethoxy)phenyl]-2-oxopropionic acid bistrifluoroacetate 710 mg (1.41 mmol) of methyl 2-acetylamino-3-[4-cyano-2-(2-((1-(1-methylpyridinium-4-yl)piperidine-4-carbonyl)amino)ethoxy)phenyl]acrylate was dissolved in a mixture of 10 ml of 4 N solution of hydrogen chloride in dioxane and 2 ml of ethanol, and the obtained solution was stirred at room temperature for 4 dys. The solvent was evaporated, and the obtained residue was dissolved in 10 ml of ethanol. 239 mg of ammonium carbonate was added to the obtained solution, and they were stirred at room temperature overnight. The solvent was evaporated, and the residue was dissolved in 10 ml of 6 N hydrochloric acid, and the obtained solution was stirred at 80° C. for 4 hours. The solvent was evaporated, and the obtained crude product was treated in the same manner as that in step 7 in Example 51 to obtain the title compound.

Yield: 30 mg (0.043 mmol) (3%)

H-NMR (DMSO-d6) δ:1.48–1.65 (2H, m), 1.76–1.88 (2H, m), 2.54–2.65 (1H, m), 3.13–3.28 (2H, m), 3.33–3.52 (3H, m), 3.89 (3H, s), 3.97–4.27 (3H, m), 6.78 (1H, s), 7.20 (2H, d), 7.34–7.48 (2H, m), 8.13–8.26 (3H, m), 8.32 (1H, d), 9.15 (2H, br), 9.27 (2H, br)

EXAMPLE 53

Synthesis of N-[2-(3-amidinophenoxy)-ethyl]-4-(3,4-dimethoxybenzoyl)benzamide

Step 1: Synthesis of methyl 4-(3,4-dimethoxybenzoyl)benzoate 2.1 g (15.72 mmol) of aluminum chloride, a solution of 2.39 g (12.02 mmol) of monomethyl terephthalate chloride dissolved in 2 ml of dichloromethane and 1.2 ml (9.25 mmol) of 1,2-dimethoxybenzene dissolved in 2 ml of dichloromethane were added to 10 ml of dichloromethane, and they were stirred overnight. The reaction solution was poured into 5 g of 1 N hydrochloric acid/ice. After the treatment with chloromethane as the extraction solvent in an ordinary manner, the solvent was evaporated, and the obtained residue was washed with ethyl acetate and dichloromethane to obtain-the title compound.

Yield: 1.3 g (4.33 mmol) (47%)

H-NMR (DMSO) δ:3.82 (3H, s), 3.87 (3H, s), 3.92 (3H, s), 7.08–7.14 (1H,d), 7.28–7.34 (1H, d), 7.38–7.42 (1H, d), 7.78–7.84 (2H, d), 8.08–8.14 (2H, d).

Step 2 Synthesis of 4-(3,4-dimethoxybenzoyl)benzoic acid 1.3 g (4.33 mmol) of methyl 4-(3,4-dimethoxybenzoyl)benzoate was dissolved in 50 ml of ethanol. 7 ml of 1 N sodium hydroxide solution was added to the obtained solution, and they were stirred overnight. The solvent was evaporated, and the residue was washed with ethyl acetate and then filtered to obtain the title compound.

Yield: 0.9 g (3.14 mmol) (73%)

H-NMR (DMSO) δ:3.82 (3H, s), 3.87 (3H, s), 7.08–7.14 (1H, d), 7.30–7.34(1H, d), 7.39–7.41 (1H, d), 7.76–7.82 (2H, d).8.06–8.12 (2H, d).

Step 3: Synthesis of 3-[2-(t-butoxycarbonylamino)ethoxy]benzonitrile 5.85 g (29 mmol) of t-butyl (2-bromoethyl)carbamate was dissolved in 100 ml of dimethylformamide. 2.38 g (26.4 mmol) of 3-hydroxybenzonitrile, 3.04 g (53 mmol) of potassium carbonate and 4.31 g (53 mmol) of sodium iodide were added to the obtained solution, and they were stirred at 50° C. for 6 hours. After the treatment with ethyl acetate as the extraction solvent in an ordinary manner, the obtained crude product was purified by the silica gel column chromatography to obtain the title compound.

Yield: 3.3 g (13.3 mmol) (51%)

H-NMR (CDCl3) δ:1.44 (1H, s), 3.55 (2H, dt), 4.05 (2H, t), 4.95 (1H, brs), 7.12 (1H, d), 7.14 (1H, s), 7.26 (1H, d), 7.38 (1H, t)

Step 4: Synthesis of 3-(2-aminoethoxy)benzonitrile monohydrochloride 1.41 g of 3-[2-(t-butoxycarbonylamino)ethoxy]benzonitrile was dissolved in 20 ml of 4 N solution of hydrogen chloride in dioxane, and the obtained solution was stirred at room temperature for 2 hours. The solvent was evaporated, and the residue was suspended in dichloromethane. The obtained suspension was filtered to obtain hydrochloride of the title compound.

Yield: 0.89 g (4.48 mmol) (83%)

Step 5: Synthesis of N-[2-(3-cyanophenoxy)ethyl]-4-(3,4-dimethoxybenzoyl)benzamide 0.68 g (3.45 mmol) of 3-(2-aminoethoxy)benzonitrile monohydrochloride was dissolved in 20 ml of N,N-dimethylformamide (dehydrated). 0.9 g (3.14 mmol) of 4-(3,4-dimethoxybenzoyl)benzoic acid, 0.47 g (3.45 mmol) of 1-hydroxybenzotriazole, 0.48 ml (3.45 mmol) of triethylamine and 0.66 g (3.45 mmol) of 1-(3-dimethylaminopropyl)-3-ethylcarbodiimide hydrochloride were added to the obtained solution, and they were stirred overnight. The solvent was evaporated, and the residue was treated with ethyl acetate as the extraction solvent in an ordinary manner to obtain the title compound.

Yield: 1.4 g (3.25 mmol) (94%)

H-NMR (CDCl3) δ:3.89–3.94 (2H, m), 3.94 (3H, s), 3.97 (3H, s), 4.18–4.24 (2H, t), 6.67 (1H, br), 6.87–6.92 (1H, d).7.14–7.19 (2H, m), 7.20–7.44 (3H, m), 7.48–7.50 (1H, d), 7.79–7.83 (2H, d), 7.86–7.92 (2H, d).

Step 6: Synthesis of N-[2-(3-amidinophenoxy)ethyl]-4-(3,4-dimethoxybenzoyl)benzamide 0.5 g (1.16 mmol) of N-[2-(3-cyanophenoxy)ethyl]-4-(3,4-dimethoxybenzoyl)benzamide was dissolved in 10 ml of N,N-dimethylformamide (dehydrated). 0.21 g (2.32 mmol) of sodium hydrogensulfide dihydrate and 0.24 g (1.16 mmol) of magnesium chloride hexahydrate were added to the obtained solution under cooling with ice, and they were stirred at room temperature for 2.5 hours. After the treatment with ethyl acetate as the extraction solvent in an ordinary manner, the solvent was evaporated, and the obtained crude product was dissolved in 20 ml of acetone. 0.56 ml (9.0 mmol) of methyl iodide was added to the solution, and they were refluxed for 3 hours. The solvent was evaporated, and the obtained crude product was washed with ethyl acetate. After the filtration, the obtained crystals were dissolved in 10 ml of methanol. 155 mg (2.0 mmol) of ammonium acetate was added to the obtained solution, and they were stirred for 3 hours. The solvent was evaporated, and the residue was treated in the same manner as that in step 7 in Example 51 to obtain the title compound.

Yield: 160 mg (0.285 mmol) (25%)

MS (ESI,m/z) 448 (MH+)

H-NMR (DMSO) δ:3.68–3.75 (2H,q), 3.82 (3H, s), 3.87 (3H, s), 4.21–4.29 (2H, t), 7.09–7.13 (1H, d), 7.29–7.43 (5H, m), 7.50–7.58 (1H, t), 7.75–7.80 (2H, d), 7.98–8.04 (2H, d), 8.95–9.00 (1H, t), 9.10 (2H, s), 9.30 (2H, s).

EXAMPLE 54

Determination of Activity of Inhibiting the Activated Blood-coagulation Factor X 130 µl of 100 mM tris hydrochloride buffer adjusted to pH 8.4 was added to 10 µl of an aqueous solution of a compound to be tested. Then 10 µl of a 0.5 unit/ml solution of activated human blood coagulation factor X (a product of Enzyme Research Co.) in tris hydrochloride of pH 8.4 was added to the resultant mixture. After the incubation at room temperature for 10 minutes, 50 µl of a solution of N-benzoyl-L-isoleucyl-L-glutamyl-glycyl-L-arginyl-P-nitroanilide hydrochloride (a product of Peptide Institute, Inc.) adjusted to 0.8 mM with tris hydrochloride (pH 8.4) was added thereto. The absorbance was determined and then the initial reaction rate was determined. A control was prepared in the same manner as that described above except that the solution of the compound to be tested was replaced with 10 µl of tris hydrochloride buffer adjusted to pH 8.4. The absorbance was determined with MICROPLATE READER Model 3550-UV (a product of BIO RAD) at a wave length of 405 nm at intervals of 15 seconds for 16 minutes. The negative logarithm (pIC$_{50}$) of a concentration of the test compound which inhibits 50% of the activity (initial rate) of the activated blood coagulation factor X in the absence of the test compound was determined, and employed as the index of the activity of inhibiting activated blood coagulation factor X.

The activities, of inhibiting activated blood coagulation factor X, of representative compounds are shown in Table 1 given below.

EXAMPLE 55

Determination of Thrombin-inhibiting Activity

130 µl of 100 mM tris hydrochloride buffer adjusted to pH 8.4 was added to 10 µl of an aqueous solution of a test compound. Then 10 μl of a solution of human thrombin (a product of SIGMA Co.) adjusted to 2 units/ml with tris hydrochloride buffer of pH 8.4 was added to the resultant mixture. After the incubation at room temperature for 10 minutes, 50 μl of a solution of D-phenylalanyl-L-pipecolyl-L-arginyl-P-nitroanilide dihydrochloride (S-2238; a product of Daiichi Kagaku Yakuhin Co.) adjusted to 0.4 mM with tris hydrochloride buffer of pH 8.4 was added thereto. The absorbance was determined and then the initial reaction rate was determined. A control was prepared in the same manner as that described above except that the solution of the compound to be tested was replaced with 10 μl of tris hydrochloride buffer adjusted to pH 8.4. The absorbance was determined with MICROPLATE READER Model 3550-UV (a product of MIO RAD) at a wave length of 405 nm at intervals of 15 seconds for 16 minutes. The negative logarithm ($pIC_{50}$) of a concentration of the test compound which inhibits 50% of the activity (initial rate) of the thrombin in the absence of the test compound was determined, and employed as the index of the activity of inhibiting thrombin.

The activities, of inhibiting thrombin, of representative compounds are shown in Table 1 given below.

EXAMPLE 56

Determination of Blood Anticoagulating Activity

The blood anticoagulating activity was determined by a prothrombin time (PT) determination method. The PT was determined as follows: The blood was taken from healthy people. 3.8% aqueous trisodium citrate solution was added to the blood in a volume ratio of 1:10. The blood plasma was separated by the centrifugation. 5 μl of DMSO solution containing a test compound was added to 45 μl of the blood plasma. After the incubation at room temperature for 2 minutes, a test tube containing the blood plasma solution was placed in Sysmex CA-3000 fully automatic blood coagulation determination device (a product of Toa Medical Electronics Co., Ltd.), and incubated at 37° C. for 3 minutes. 100 μl of Sysmex PT II (rabbit brain tissue thromboplastin, 13.2 mM calcium chloride; a product of Toa Medical Electronics Co., Ltd.) was fed into the test tube. PT was automatically determined with the device. A sample containing 5 μl of DMSO in place of the solution of the test compound was used as the control. The negative logarithm (PT2) of the concentration of the test compound which elongated PT of the control to the twice as long was determined, and employed as the index of the blood anticoagulating activity.

TABLE 1

|  | Activity of inhibiting activated blood coagulation factor X ($pIC_{50}$) | Thrombin-inhibiting activity ($pIC_{50}$) |
|---|---|---|
| Compd. of Ex. 2 | 7 | <3.0 |
| Compd. of Ex. 4 | 7.5 | <3.0 |
| Compd. of Ex. 5 | 7.2 | 5.2 |
| Compd. of Ex. 6 | 7.4 | <3.0 |
| Compd. of Ex. 8 | 7 | <3.0 |
| Compd. of Ex. 9 | 7 | 5.5 |
| Compd. of Ex. 10 | 7.4 | <3.0 |
| Compd. of Ex. 13 | 7.6 | <3.1 |
| Compd. of Ex. 14 | 7.8 | <4.0 |
| Compd. of Ex. 15 | 8 | <4.0 |
| Compd. of Ex. 26 | 7.8 | <4.0 |
| Compd. of Ex. 28 | 7.8 | <4.0 |
| Compd. of Ex. 29 | 7.9 | <4.0 |

TABLE 1-continued

|  | Activity of inhibiting activated blood coagulation factor X ($pIC_{50}$) | Thrombin-inhibiting activity ($pIC_{50}$) |
|---|---|---|
| Compd. of Ex. 37 | 7.3 | <4.0 |
| Compd. of Ex. 38 | 7 | 3.3 |
| Compd. of Ex. 42 | 7.2 | <3.3 |
| Compd. of Ex. 43 | 7.8 | <4.0 |
| Compd. of Ex. 51 | 8.1 | 4.3 |
| Compd. of Ex. 52 | 7.1 | 4.2 |

It is apparent from the results that the benzamidine derivatives of the present invention have a specifically high activity of inhibiting the activated blood coagulation factor X, and they exhibit a high anticoagulating activity based on this inhibiting activity.

The structural formulae of the compounds of the present invention described in the Examples are given below.

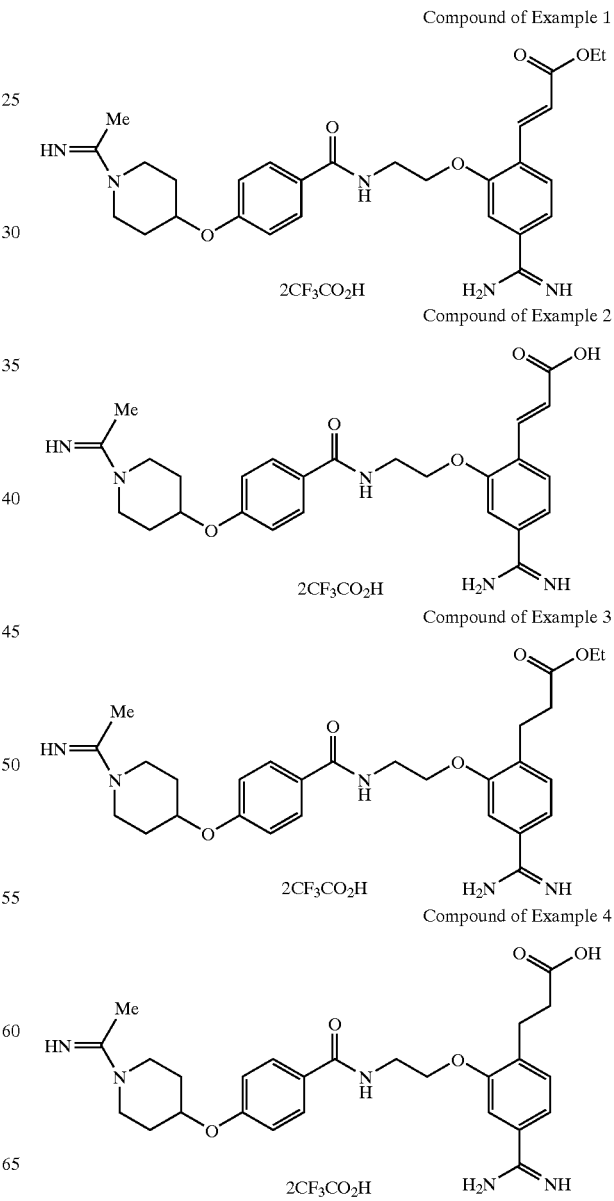

Compound of Example 5
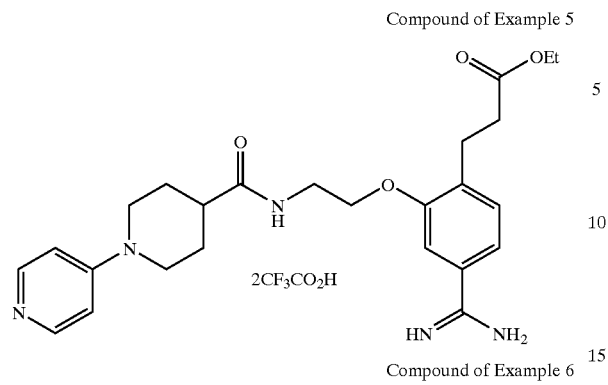
Compound of Example 6
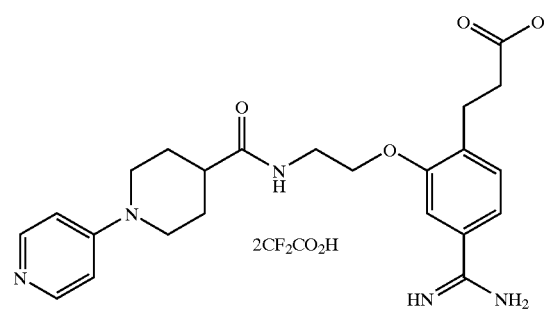
Compound of Example 7
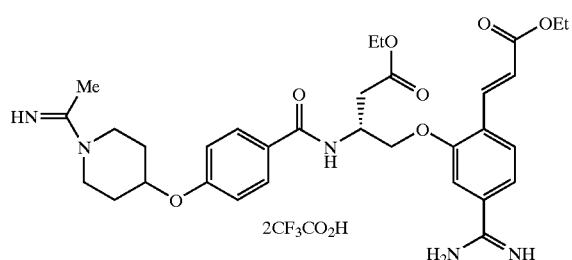
Compound of Example 8
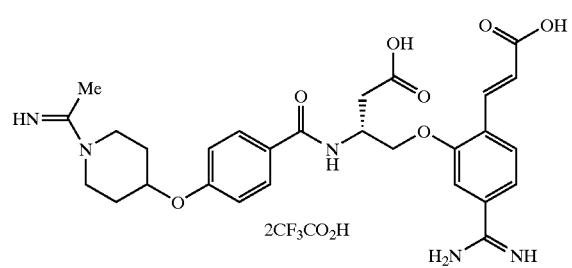
Compound of Example 9
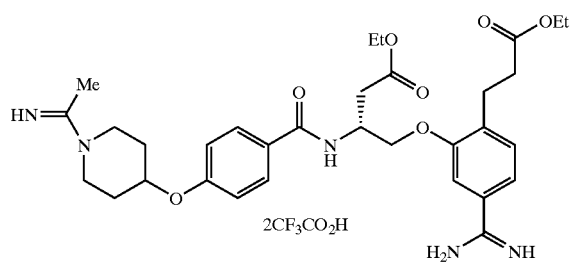
Compound of Example 10
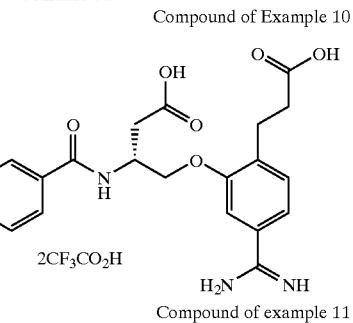
Compound of example 11
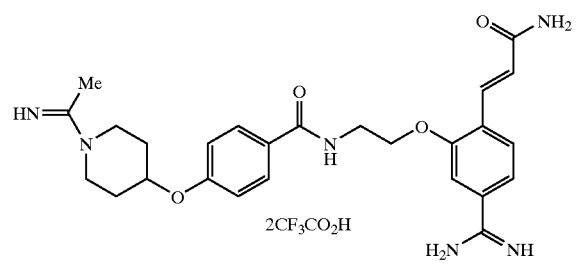
Compound of Example 12
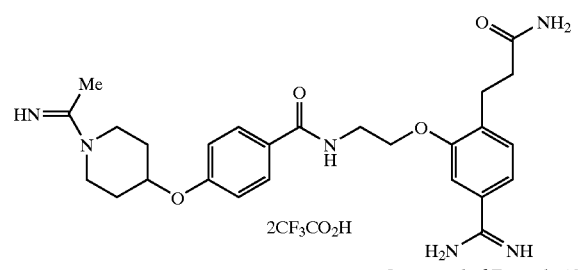
Compound of Example 13
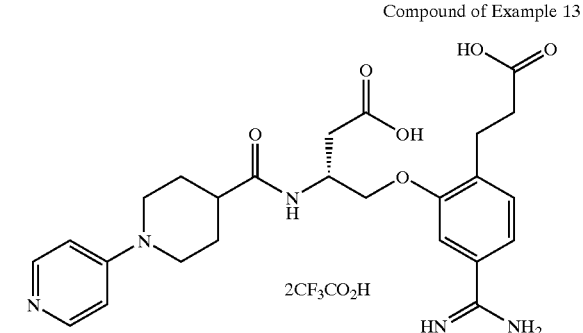
Compound of Example 14
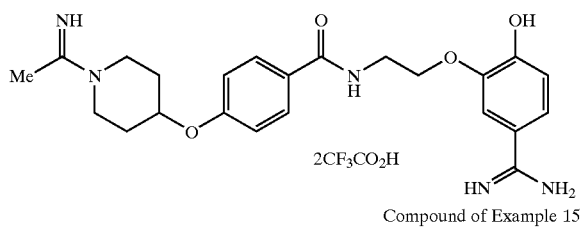
Compound of Example 15
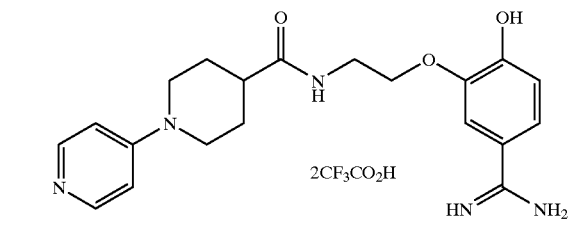

-continued
Compound of Example 16
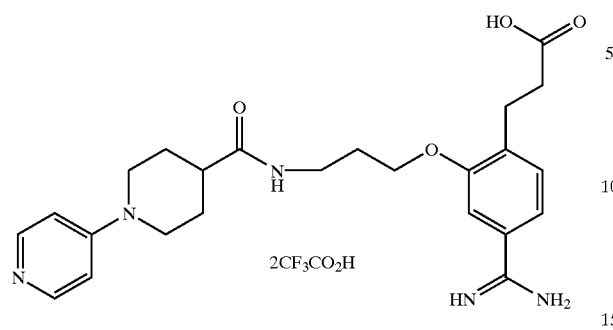
2CF₃CO₂H
Compound of Example 17
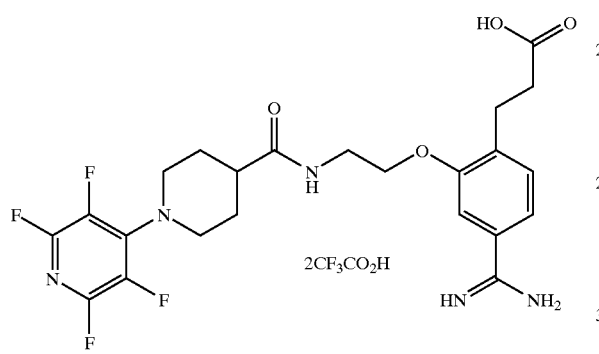
2CF₃CO₂H
Compound of Example 18
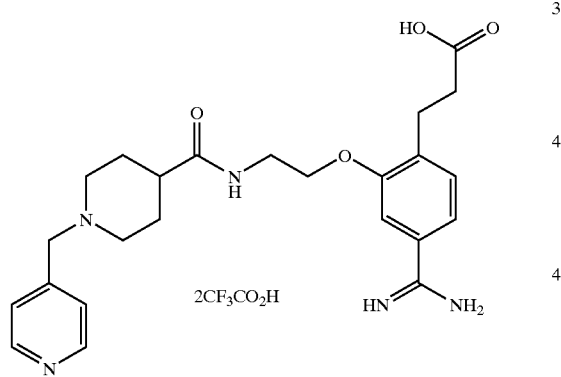
2CF₃CO₂H
Compound of Example 19
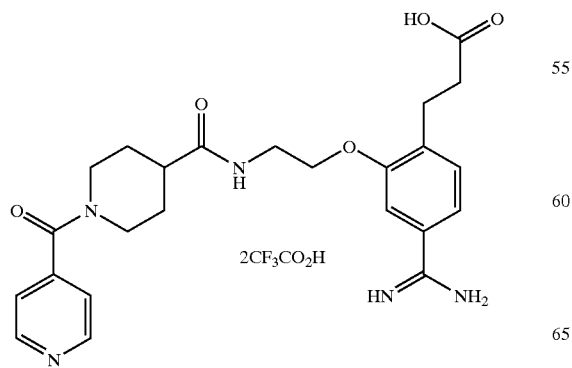
2CF₃CO₂H
-continued
Compound of example 20
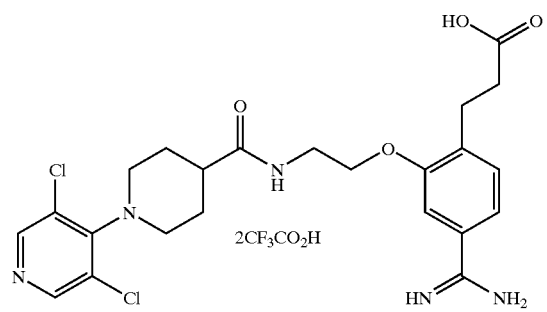
2CF₃CO₂H
Compound of Example 21
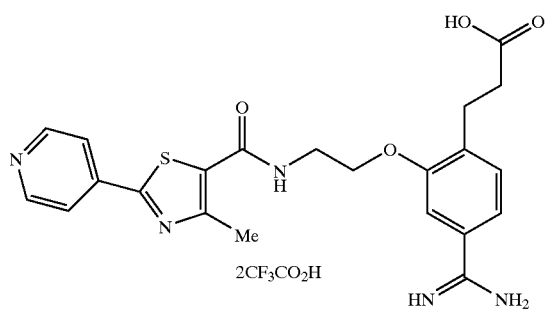
2CF₃CO₂H
Compound of Example 22
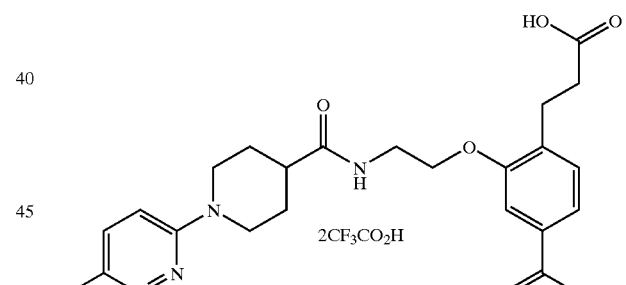
2CF₃CO₂H
Compound of Example 23
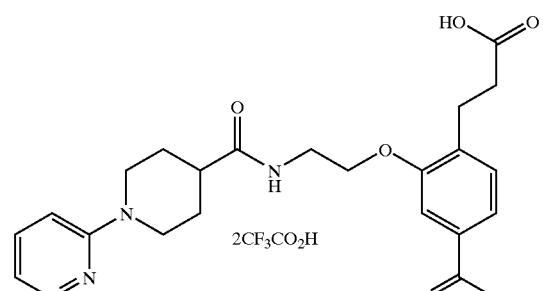
2CF₃CO₂H Compound of example 24
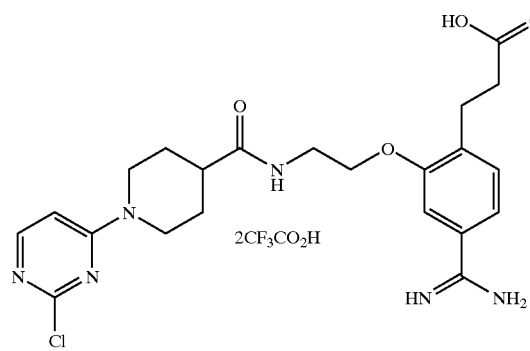
Compound of Example 25
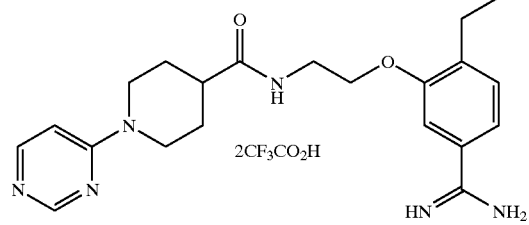
Compound of Example 26
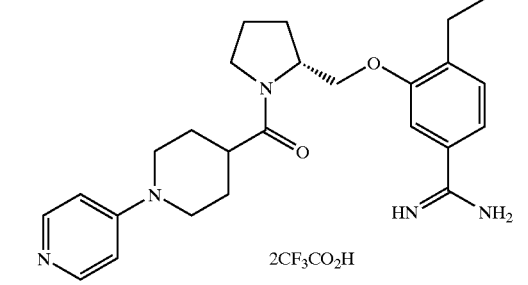
Compound of Example 27
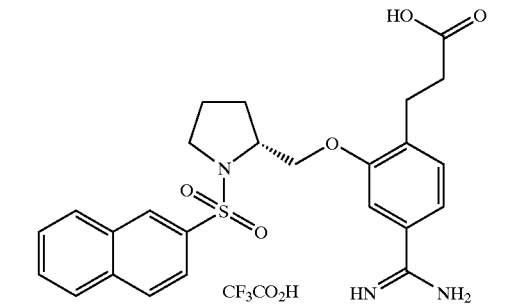
Compound of Example 28
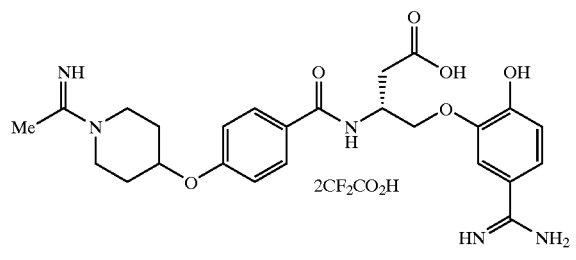
Compound of Example 29
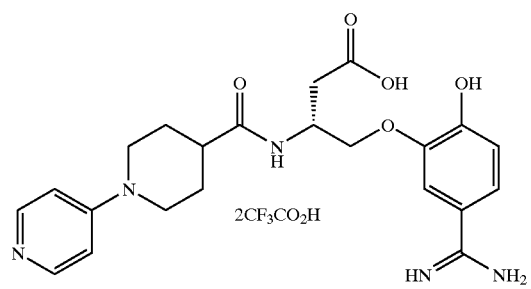
Compound of example 30
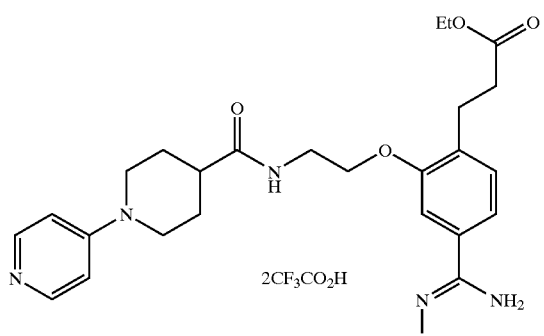
Compound of Example 31
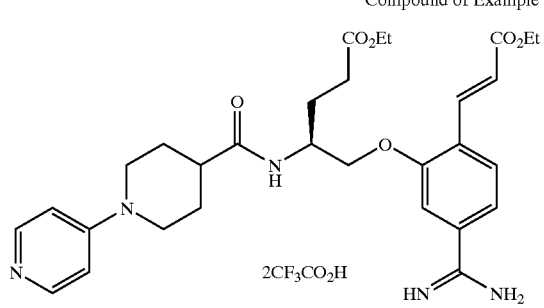
Compound of Example 32
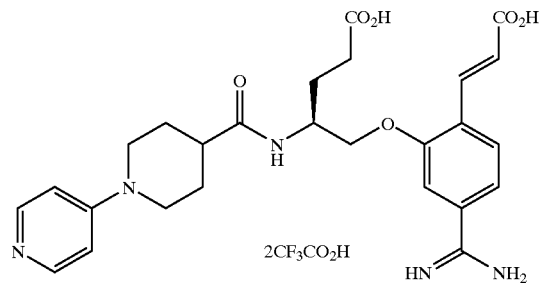

Compound of Example 33
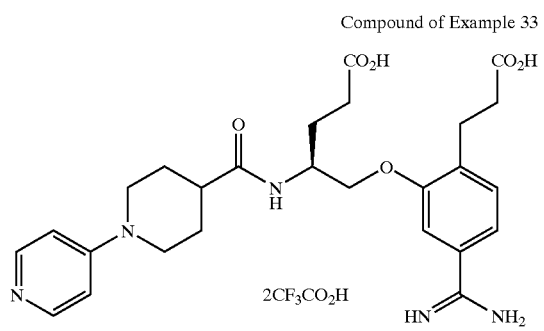
Compound of Example 34
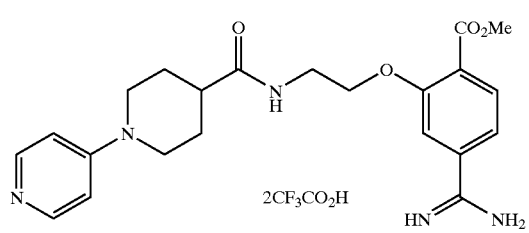
Compound of Example 35
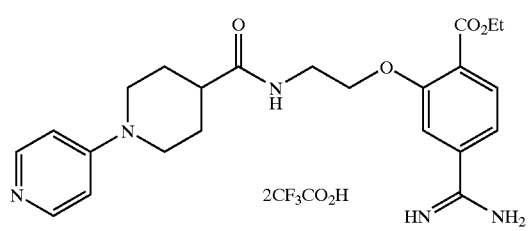
Compound of Example 36
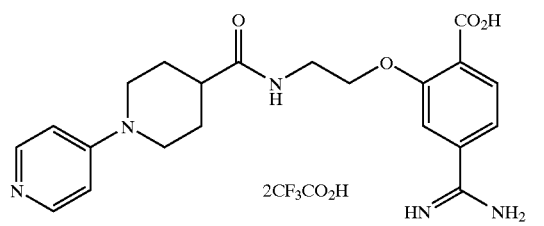
Compound of Example 37
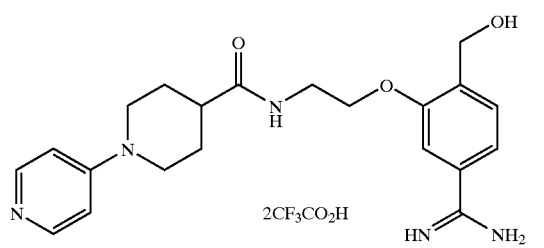
Compound of Example 38
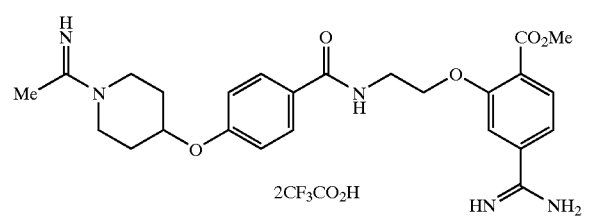
Compound of Example 39
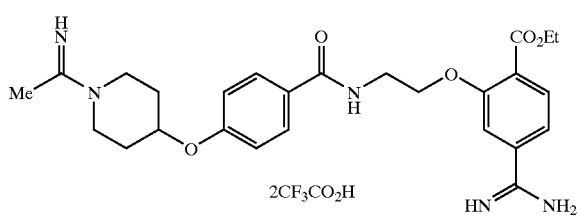
Compound of Example 40
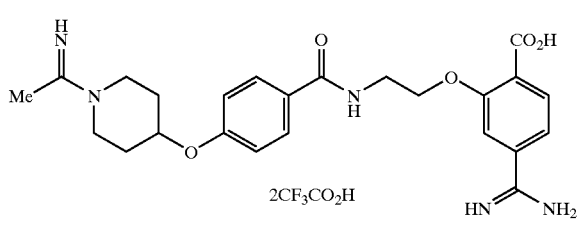
Compound of example 41
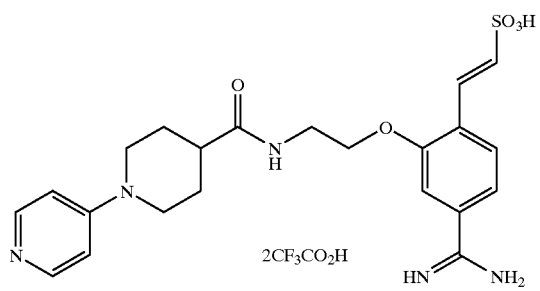
Compound of Example 42
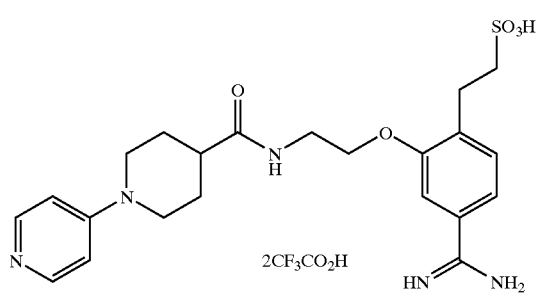
Compound of Example 43
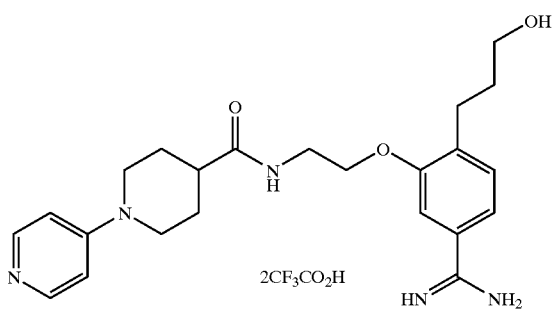

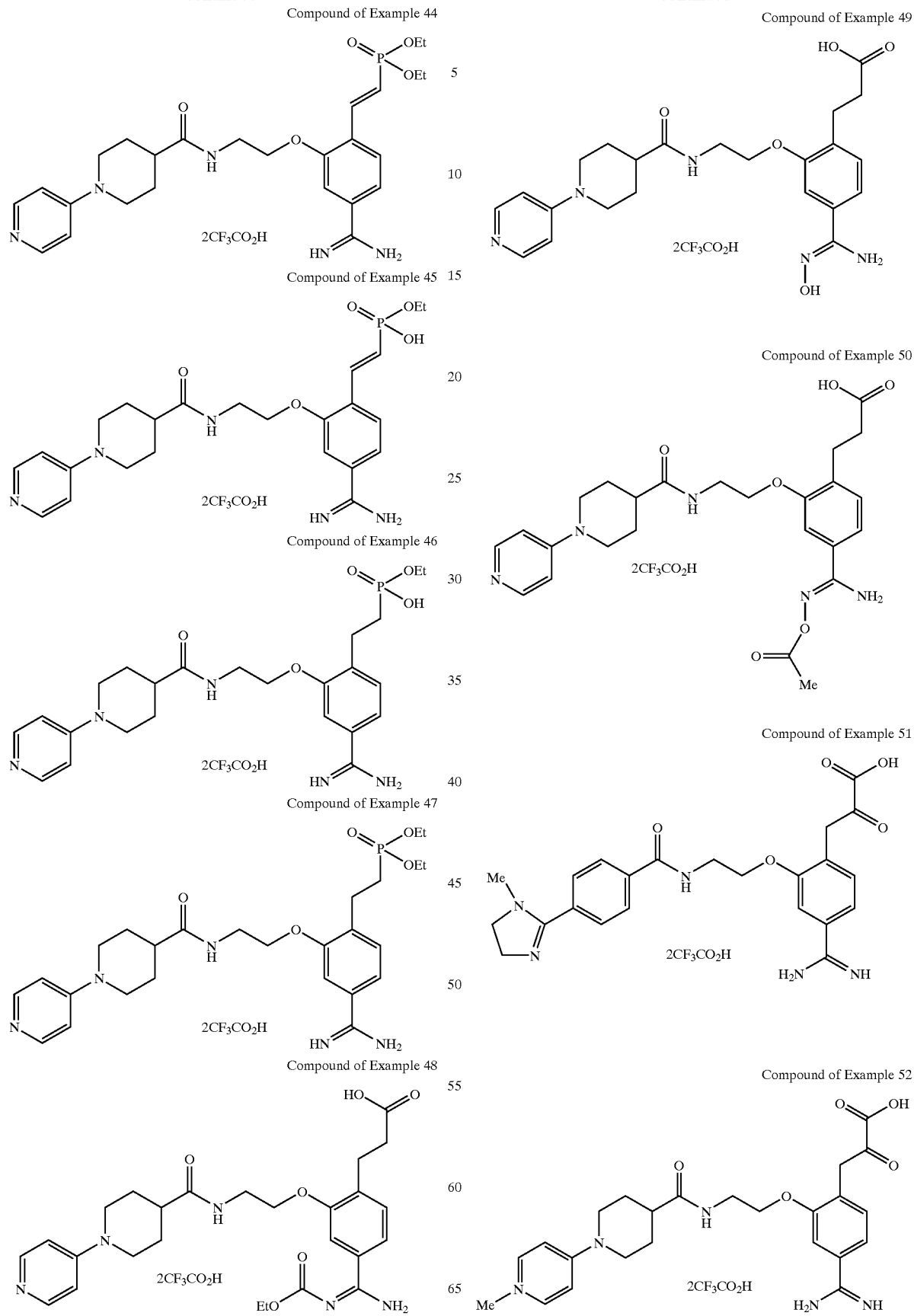

Compound of Example 53

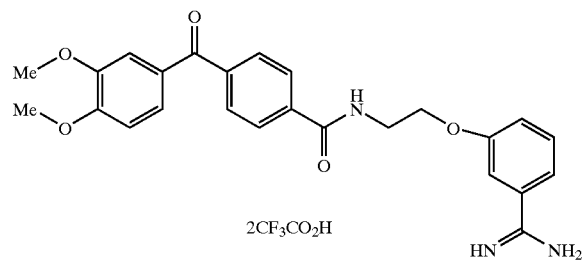

2CF₃CO₂H

Effect of the Invention

The anticoagulant containing a compound of the present invention or a salt thereof as the active ingredient has a blood-coagulation inhibiting effect based on the excellent effect of inhibiting activated blood-coagulation factor X. Therefore, the compounds of the present invention are usable as agents for preventing or treating diseases such as cerebrovascular disorders such as cerebral infarction, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral obliteration; deep vein thrombosis; disseminated intravascular coagulation syndrome; thrombus formation after an artificial blood vessel-forming operation or artificial valve substitution; re-occlusion and re-stenosis after a coronary bypass-forming operation; re-occlusion and re-stenosis after reconstructive operation for the blood circulation such as percutaneous transluminal coronary angioplasty (PTCA) or percutaneous transluminal coronary recanalization (PTCR); and thrombus formation in the course of the extracorporeal circulation.

What is claimed is:

1. A composition comprising:

a) one or more benzamidine compounds of the following formula (1-1) or a pharmaceutically acceptable salt thereof:

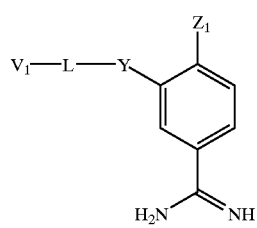
(1-1)

wherein L represents an organic group of any of the following formulae (2) to (5):

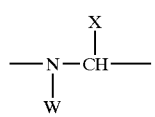
(2)

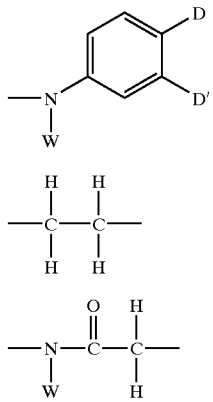

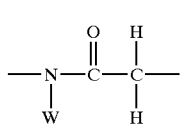

wherein W in formulae (2), (3) and (5) represents a hydrogen atom, an alkyl group having 1 to 6 carbon atoms, an aryl group having 4 to 10 carbon atoms or an aralkyl group having 5 to 12 carbon atoms, one of D and D' in formula (3) represents a bond to Y in general formula (1-1) and the other represents a hydrogen atom, X in formula (2) represents a hydrogen atom, carboxyl group, an alkoxycarbonyl group having 1 to 3 carbon atoms, an alkyl group having 1 to 3 carbon atoms, which optionally has a substituent(s), or a benzyl group which optionally has a substituent(s); wherein the substituent(s) is selected from the group consisting of a carboxyl group, alkoxycarbonyl groups having 2 to 8 carbon atoms, alkylsulfonyloxy groups having 1 to 6 carbon atoms, piperidyloxy group, iminoalkylpiperidyloxy groups having 6 to 10 carbon atoms, alkoxycarbonylpiperidyloxy groups having 7 to 14 carbon atoms, piperidylalkyl groups having 6 to 8 carbon atoms, iminoalkylpiperidylalkyl groups having 7 to 11 carbon atoms, alkoxycarbonylpiperidylalkyl groups having 8 to 15 carbon atoms, pyrrolidinyloxy group, iminoalkylpyrrolidinyloxy groups having 5 to 9 carbon atoms, alkoxycarbonylpyrrolidinyloxy groups having 7 to 13 carbon atoms, amidino group, mono- or dialkylamidino groups having 2 to 7 carbon atoms, hydroxyl group, halogeno groups, indolyl group and alkyl groups having 1 to 3 carbon atoms, X and W in formula (2) may be bonded together to form a ring and, in this case, —W—X— represents an ethylene group, trimethylene group or tetramethylene group, when L is an organic group of any of formulae (2) to (4), $V_1$ represents a hydrogen atom, benzoyl, benzenesulfonyl, 2-naphthalenesulfonyl, piperazinecarbonyl, cinnamoyl, piperidinecarbonyl, 4-methylthiazole-5-carbonyl phenylacetyl, phenylthiocarbonyl or benzimidoyl group, which optionally has a substituent(s), or an alkanesulfonyl group having 1 to 6 carbon atoms, which optionally has a substituent(s), and when L is an organic group of formula (5), $V_1$ represents an aryl group having 4 to 10 carbon atoms, which optionally has a substituent(s), when L is an organic group of any of formulae (2) to (5) and $V_1$ has a substituent(s); wherein the substituent is selected from the group consisting of carboxyl group, alkoxycarbonyl groups having 2 to 7 carbon atoms, carbamoyl group, mono- or dialkylcarbamoyl groups having 2 to 7 carbon atoms, amidino group, mono- or dialkylamidino groups having 2 to 7 carbon atoms, acyl groups having 1 to 8 carbon atoms, halogeno groups, amino group, mono- or dialkylamino groups having 1 to 6 carbon atoms, arylamino groups having 4 to 6 carbon atoms, alkoxycarbonylamino groups having 2 to 7 carbon atoms, aminoalkyl groups having 1 to 3 carbon atoms, mono- or dialkylaminoalkyl groups having 2 to 7 carbon atoms, N-alkyl-N-alkoxycarbonylaminoalkyl groups having 4 to 10 carbon atoms, piperidyloxy group, iminoalkylpiperidyloxy groups having 6 to 10 carbon atoms, alkoxycarbonylpiperidyloxy groups having 8 to 14 carbon atoms, pyrrolidinyloxy group, iminoalkylpyrrolidinyloxy groups having 5 to 9 carbon atoms, alkoxycarbonylpyrrolidinyloxy groups having 7 to 13 carbon atoms, hydroxycarbonylalkyl groups having 2 to 7 carbon atoms, alkoxycarbonylalkyl groups having 3 to 8 carbon atoms, hydroxycarbonylalkenyl groups having 3 to 7 carbon atoms, alkoxycarbonylalkenyl groups having 4 to 8 carbon atoms, aryl groups having 4 to 10 carbon atoms, arylalkenyl groups having 6 to 12 carbon atoms, alkoxyl groups having 1 to 10 carbon atoms, nitro group, trifluoromethyl group, alkyl groups having 3 to 8 carbon atoms, arylsulfonyl groups having 4 to 10 carbon atoms, arylalkyl groups having 5 to 12 carbon atoms, piperazinecarbonyl group, iminoalkylpiperazinecarbonyl groups having 7 to 10 carbon atoms, piperazinesulfonyl group, iminoalkylpiperazinesulfonyl groups having 6 to 9 carbon atoms, piperidylalkyl groups having 6 to 9 carbon atoms, iminoalkylpiperidylalkyl groups having 8 to 12 carbon atoms, piperidylidenealkyl groups having 6 to 9 carbon atoms, iminoalkylpiperidylalkyl groups having 8 to 12 carbon atoms, guanidino group, dialkylguanidino groups having 3 to 5 carbon atoms, phosphono group, dialkoxyphosphoryl groups having 2 to 9 carbon atoms, monoalkoxyhydroxyphosphoryl groups having 1 to 4 carbon atoms, trialkylamidino groups having 4 to 7 carbon atoms, dialkoxybenzoyl groups having 9 to 13 carbon atoms, 1-alkylpyridinio groups having 6 to 9 carbon atoms and groups of the following formulae:

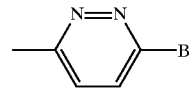

(6)

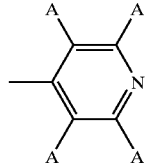

(7)

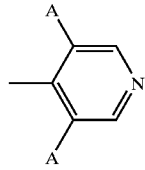

(8)

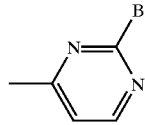

(9)

wherein A in formulae (6) and (7) represents a halogeno group, and B in formulae (8) and (9) represents a hydrogen atom, an alkyl group having 1 to 6 carbon atoms, a halogeno group or amino group, Y represents any of following formulae (10) to (16):

$$\text{—}(CH_2)_n\text{—}O\text{—} \quad (10)$$

$$\text{—}(CH_2)_n\text{—}S\text{—} \quad (11)$$

$$\text{—}CH_2\text{—}CH_2\text{—} \quad (12)$$

$$\text{—}CH\text{=}CH\text{—} \quad (13)$$

$$\text{—}\overset{\overset{O}{\|}}{C}\text{—}\overset{\overset{H}{|}}{N}\text{—} \quad (14)$$

$$\text{—}\overset{\overset{O}{\|}}{C}\text{—}\overset{\overset{H}{|}}{N}\text{—}CH_2\text{—} \quad (15)$$

$$\text{—}CH_2\text{—}\overset{\overset{R^1}{|}}{N}\text{—} \quad (16)$$

wherein n in formulae (10) and (11) represents an integer of 0 to 2, $R^1$ in formula (16) represents a hydrogen atom, a hydroxycarbonylalkyl group having 2 to 7 carbon atoms, an alkoxycarbonylalkyl group having 3 to 8 carbon atoms or a hydroxycarbonylalkenyl group having 3 to 7 carbon atoms, $Z_1$ represents a group of any of following formulae (17) to (24):

$$\text{—}(CH_2)_m\text{—}\overset{\overset{O}{\|}}{C}\text{—}R^2 \quad (17)$$

$$\text{—}CH\text{=}CH\text{—}\overset{\overset{O}{\|}}{C}\text{—}R^2 \quad (18)$$

$$\text{—}(CH_2)_{m+1}\text{—}OR^3 \quad (19)$$

$$\text{—}CH\text{=}CH\text{—}\overset{\overset{O}{\|}}{\underset{\underset{O}{\|}}{S}}\text{—}OR^4 \quad (20)$$

$$\text{—}(CH_2)_m\text{—}\overset{\overset{O}{\|}}{\underset{\underset{O}{\|}}{S}}\text{—}OR^4 \quad (21)$$

$$\text{—}CH\text{=}CH\text{—}\overset{\overset{O}{\|}}{\underset{\underset{OR^5}{|}}{P}}\text{—}OR^4 \quad (22)$$

-continued

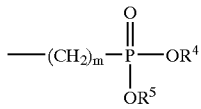
(23)

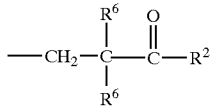
(24)

wherein m in formulae (17), (19), (21) and (23) represents an integer of 0 to 3, $R^2$ in formulae (17), (18) and (24) represents a hydroxyl group, an alkoxyl group having 1 to 5 carbon atoms, trifluoromethyl group, amino group or a mono- or dialkylamino group having 1 to 6 carbon atoms, $R^3$ in formula (19) represents a hydrogen atom, an alkyl group having 1 to 6 carbon atoms or acetyl group, $R^4$ in formulae (20) to (23) represents hydrogen atom or an alkyl group having 1 to 6 carbon atoms, $R^5$ in formulae (22) and (23) represents a hydrogen atom or an alkyl group having 1 to 6 carbon atoms, and $R^6$ in formula (24) represents a halogeno group; and b) a pharmaceutically acceptable carrier.

2. The composition according to claim 1, wherein, in general formula (1-1), L represents an organic group of formula (2), W represents a hydrogen atom and X represents a hydrogen atom, carboxymethyl group or ethoxycarbonylmethyl group.

3. The composition according to claim 1, wherein, in general formula (1-1), Y represents an organic group of general formula (10) and n represents an integer of 1 or 2.

4. The composition according to claim 1, wherein $V_1$ in general formula (1-1) represents 1-acetimidoyl-4-piperidyloxybenzoyl group, 1-(4-pyridyl)piperidine-4-carbonyl group, 1-(2,3,5,6-tetrafluoropyridine-4-yl) piperidine-4-carbonyl group, 1-(3,5-dichloropyridine-4-yl)-piperidine-4-carbonyl group, 1-(6-chloropyridazine-3-yl)-piperidine-4-carbonyl group, 1-(pyridazine-3-yl)piperidine-4-carbonyl group, 1-(2-chloropyrimidine-4-yl)-piperidine-4-carbonyl group, 1-(pyrimidine-4-yl)-piperidine-4-carbonyl group, 1-(4-pyridine-4-ylmethyl)-piperidine-4-carbonyl group, 1-(4-pyridine-4-carbonyl)-piperidine-4-carbonyl group or 4-methyl-2-pyridyl-4-yl-thiazole-5-carbonyl group.

5. The composition according to claim 1, wherein, $Z_1$, in general formula (1-1) represents a carboxyethyl group, ethoxycarbonylethyl group, carboxyvinyl group; ethoxycarbonylvinyl group, carbamoylethyl group, carbamoylvinyl, carboxyl group, ethoxycarbonyl group, methoxycarbonyl group, sulfoethyl group, sulfovinyl group, phosphonovinyl group, diethoxyphosphorylvinyl group, monoethoxyhydroxyphosphorylvinyl group, sulfonoethyl group, diethoxyphosphorylethyl group, monoethoxyhydroxyphosphorylethyl group, hydroxymethyl group, hydroxypropyl group or acetoxymethyl group.

6. The composition according to claim 1, wherein, in general formula (1-1), L represents an organic group of formula (2), Y represents an organic group of formula (10), $V_1$ represents 1-acetimidoyl-4-piperidyloxybenzoyl group or 1-(4-pyridyl)-piperidine-4-carbonyl group, and $Z_1$ represents a carboxyethyl group, ethoxycarbonylethyl group, sulfoethyl group, hydroxymethyl group or hydroxypropyl group.

7. The composition according to claim 1, wherein, in general formula (1-1), L represents an organic group of formulae (2) to (4), and Y represents an organic group of formulae (10) to (13).

8. The composition according to claim 1, wherein, in general formula (1-1), when L represents an organic group of any of formulae (2) to (4), $V_1$ represents a hydrogen atom, benzoyl, benzene sulfonyl, 2-naphthalenesulfonyl, cinnamoyl, piperidinecarbonyl, phenylacetyl, phenylthiocarbonyl or benzimidoyl group which optionally has a substituent(s), or an alkanesulfonyl group, having 1 to 6 carbon atoms, which optionally has a substituent(s); and when L is an organic group of formula (5), $V_1$ represents an aryl group, having 4 to 10 carbon atoms, which optionally has a substituent(s), when L represents an organic group of any of formulae (2) to (5), the substituents of $V_1$ include a carboxyl group, alkoxycarbonyl groups having 2 to 7 carbon atoms, carbamoyl group, mono- or dialkylcarbamoyl groups having 2 to 7 carbon atoms, trialkylamidino groups having 4 to 7 carbon atoms, amidino group, mono- or dialkylamidino groups having 2 to 7 carbon atoms, acyl groups having 1 to 8 carbon atoms, halogeno groups, amino group, mono- or dialkylamino groups having 1 to 6 carbon atoms, arylamino groups having 4 to 6 carbon atoms, alkoxycarbonylamino groups having 2 to 7 carbon atoms, aminoalkyl groups having 1 to 3 carbon atoms, mono- or dialkylaminoalkyl groups having 2 to 7 carbon atoms, N-alkyl-N-alkoxycarbonylaminoalkyl groups having 4 to 10 carbon atoms, piperidyloxy group, iminoalkylpiperidyloxy groups having 6 to 10 carbon atoms, alkoxycarbonylpiperidyloxy groups having 8 to 14 carbon atoms, pyrrolidinyloxy group, iminoalkylpyrrolidinyloxy groups having 5 to 9 carbon atoms, alkoxycarbonylpyrrolidinyloxy groups having 7 to 13 carbon atoms, hydroxycarbonylalkyl groups having 2 to 7 carbon atoms, alkoxycarbonylalkyl groups having 3 to 8 carbon atoms, hydroxycarbonylalkenyl groups having 3 to 7 carbon atoms, alkoxycarbonylalkenyl groups having 4 to 8 carbon atoms, aryl groups having 4 to 10 carbon atoms, arylalkenyl groups having 6 to 12 carbon atoms, alkoxyl groups having 1 to 10 carbon atoms, nitro group, trifluoromethyl group, alkyl groups having 3 to 8 carbon atoms, arylsulfonyl groups having 4 to 10 carbon atoms, arylalkyl groups having 5 to 12 carbon atoms, piperazinecarbonyl group, iminoalkylpiperazinecarbonyl groups having 7 to 10 carbon atoms, piperazinesulfonyl group, iminoalkylpiperazinesulfonyl groups having 6 to 9 carbon atoms, piperidylalkyl groups having 6 to 9 carbon atoms, iminoalkylpiperidylalkyl groups having 8 to 12 carbon atoms, piperidylidenealkyl groups having 6 to 9 carbon atoms, iminoalkylpiperidylidenealkyl groups having 8 to 12 carbon atoms, guanidino group, dialkylguanidino groups having 3 to 5 carbon atoms, phosphono group, dialkoxyphosphoryl groups having 2 to 9 carbon atoms or mono alkoxyhydroxyphosphoryl groups having 1 to 4 carbon atoms, Y represents any of formulae (10) to (16), n in formulae (10) and (11) represents an integer of 1 or 2, and $Z_1$ represents a group of formula (17) or (18) wherein m represents an integer of 1 to 3, and $R^2$ represents hydroxyl group, an alkoxyl group having 1 to 5 carbon atoms, amino group or a mono- or dialkylamino group having 1 to 6 carbon atoms.

9. The composition according to claim 8, wherein, in general formula (1-1), L represents an organic group of formula (2), W represents a hydrogen atom and X represents a hydrogen atom, carboxymethyl group or ethoxycarbonylmethyl group.

10. The composition according to claim 8, wherein, in general formula (1-1), Y represents an organic group of general formula (10) and n represents an integer of 1.

11. The composition according to claim 8, wherein, $V_1$ in general formula (1-1) represents 1-acetimidoyl-4-piperidyloxybenzoyl group or 1-(4-pyridyl)piperidine-4-carbonyl group.

12. The composition according to claim 8, wherein, $Z_1$ in general formula (1-1) represents a carboxyethyl group, etboxycarbonylethyl group, carboxyvinyl group, ethoxycarbonylvinyl group, carbamoylethyl group or carbamoylvinyl group.

13. The composition according to claim 8, wherein, in general formula (1-1), L represents an organic group of formula (2), Y represents an organic group of formula (10), $V_1$ represents 1-acetimidoyl-4-piperidyloxybenzoyl group or 1-(4-pyridyl)-piperidine-4-carbonyl group, and $Z_1$ represents a carboxyethyl group, etboxycarbonylethyl group or carbamoylethyl group.

14. A composition comprising:
a) one or more benzamidine compounds of following formula (1-2) or a pharmaceutically acceptable salt thereof:

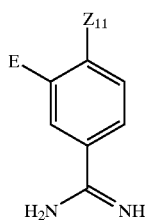

(1-2)

wherein $Z_{11}$ represents carboxyethyl group, ethoxycarbonylethyl group, hydroxymethyl group or hydroxypropyl group, and E represents an oil-soluble organic group; and b) a pharmaceutically acceptable carrier.

15. A composition comprising:
a) one or more benzamidine compounds of the formula: wherein:

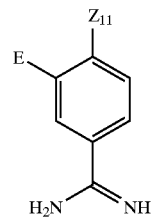

(1-2)

$Z_{11}$ is carboxyethyl, ethoxycarbonylethyl, hydroxymethyl or hydroxypropyl;
E is an oil-soluble organic group of the formula —Y—L—$V_1$—, wherein L is an organic group of the formula (2):

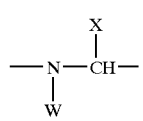

(2)

wherein W is hydrogen, $C_1$–$C_6$ alkyl, $C_4$–$C_{10}$ aryl or $C_5$–$C_{12}$ aralkyl; and X is hydrogen, carboxyl, alkoxycarbonyl having 1 to 3 carbon atoms, alkyl of 1 to 3 carbon atoms which is optionally substituted, benzyl which is optionally substituted, or X and W are bonded together to form a ring, wherein —W—X— is selected from the group consisting of ethylene, trimethylene and tetramethylene;
Y is an organic group of the formula (10):

(10)

wherein n is an integer of 0 to 2; and
$V_2$ is 1-acetamidoyl-4-piperidyloxybenzoyl or 1-(4-pyridyl)piperidine-4-carbonyl; and
b) a pharmaceutically acceptable carrier.

16. The composition according to claim 15, wherein, in general formula (1-2), L represents an organic group of formula (2), W represents a hydrogen atom, X represents a hydrogen atom, $V_2$ represents 4-(3,4-dimethoxybenzoyl)benzoyl group, 1-(1-methylpyridinium-4-yl)piperidine-4-carbonyl group or 4-(1-methyl-2-imidazoline-2-yl)benzoyl group, and $Z_2$ represents a hydrogen atom or 2-carboxy-2-oxoethyl group.

17. The composition according to claim 15, wherein, in general formula (1-2), L represents an organic group of formula (2), W represents a hydrogen atom, X represents a hydrogen atom, $V_2$ represents 4-(1-methyl-2-imidazoline2-yl)benzoyl group, and $Z_4$ represents 2-carboxy-2-oxoethyl group.

* * * * *